(12) United States Patent
Kozikowski et al.

(10) Patent No.: US 8,748,451 B2
(45) Date of Patent: *Jun. 10, 2014

(54) HDAC INHIBITORS AND THERAPEUTIC METHODS OF USING SAME

(71) Applicant: The Board of Trustees of the University of Illinois, Urbana, IL (US)

(72) Inventors: Alan Kozikowski, Chicago, IL (US); Kyle Vincent Butler, Stanford, CA (US); Jay Hans Kalin, Chicago, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,438

(22) Filed: Apr. 22, 2013

(65) Prior Publication Data

US 2013/0281484 A1  Oct. 24, 2013

Related U.S. Application Data

(62) Division of application No. 13/384,724, filed as application No. PCT/US2010/040879 on Jul. 2, 2010, now Pat. No. 8,431,538.

(60) Provisional application No. 61/227,516, filed on Jul. 22, 2009.

(51) Int. Cl.
| | |
|---|---|
| *C07D 209/86* | (2006.01) |
| *C07D 471/04* | (2006.01) |
| *A61K 31/403* | (2006.01) |
| *A61K 31/437* | (2006.01) |

(52) U.S. Cl.
USPC .............................. 514/292; 546/87; 548/444

(58) Field of Classification Search
None
See application file for complete search history.

(56) References Cited

U.S. PATENT DOCUMENTS

| | | | |
|---|---|---|---|
| 7,250,514 B1 | 7/2007 | Xiao | |
| 8,431,538 B2 * | 4/2013 | Kozikowski et al. | 514/20.5 |

FOREIGN PATENT DOCUMENTS

| | | | | |
|---|---|---|---|---|
| WO | WO-2004/113336 A1 | 12/2004 | | |
| WO | WO-2006/101456 A1 | 9/2006 | | |
| WO | WO/2006/117549 | * 11/2006 | ........... | C07D 487/04 |
| WO | WO-2006/117549 A1 | 11/2006 | | |
| WO | WO-2008/122115 A1 | 10/2008 | | |
| WO | WO/2010/015636 | * 2/2010 | ........... | C07D 471/04 |

OTHER PUBLICATIONS

Remiszewski et al., N-Hydroxy-3-phenyl-2-propenamides as Novel Inhibitors of Human Histone Deacetylase with in Vivo Antitumor Activity: Discovery of (2E)-N-Hydroxy-3-[4-[[(2-(1 H-indol-3yl)ethyl]amino]methyl]-phenyl]-2-propenamide (NVP-LAQ824), J. Med. Chem., 46:4609-4624 (2003 (already of record/cited in the IDS of Oct. 11, 2012 & r/t PCT ISR).*

Vadivelan, S., et al., "Pharmacophore Modeling and Virtual Screening Studies to Design Some Potential Histone Deacetylase Inhibitors as New Leads," *Journal of Molecular Graphics and Modeling*. 2008, vol. 26, pp. 935-946.

International Search Report in international application No. PCT/US2010/040879, dated Mar. 31, 2011.

Remiszewskit, et al., N-Hydroxy-3-phenyl-2-propenamides as Novel Inhibitors of Human Histone Deacetylase with in Vivo Antitumor Activity: Discovery of (2E)-N-Hydroxy-3[4[(2-hydroxyethl)[2-(1H-indol-3-yl)ethyl]-amino]methyl)phenyl]-2-propenamide (NVP-LAQ824), *Journal of Medicinal Chemistry*, 2003, vol. 46, pp. 4609-4624.

\* cited by examiner

*Primary Examiner* — Maury Audet
*Assistant Examiner* — Joseph Fischer
(74) *Attorney, Agent, or Firm* — Marshall, Gerstein & Borun LLP

(57) ABSTRACT

Histone deacetylases inhibitors (HDACIs) and compositions containing the same are disclosed. Methods of treating diseases and conditions wherein inhibition of HDAC provides a benefit, like a cancer, a neurodegenerative disorder, a neurological disease, traumatic brain injury, stroke, malaria, an autoimmune disease, autism, and inflammation, also are disclosed.

4 Claims, 4 Drawing Sheets

HDAC INHIBITORS AND THERAPEUTIC METHODS OF USING SAME

CROSS-REFERENCE TO RELATED APPLICATIONS

This is a divisional of U.S. application Ser. No. 13/384,724, filed Jun. 7, 2012, now U.S. Pat. No. 8,431,538, which is the U.S. national phase of International Application No. PCT/US2010/040879, filed Jul. 2, 2010, which claims the benefit of U.S. Provisional Patent Application No. 61/227,516 filed Jul. 22, 2009.

STATEMENT OF GOVERNMENTAL INTEREST

This invention was made with government support under grant number R01 AG022941 awarded by the National Institutes of Health. The government has certain rights in the invention.

FIELD OF THE INVENTION

The present invention relates to histone deacetylase (HDAC) inhibitors, to pharmaceutical compositions comprising one or more of the HDAC inhibitors, to methods of increasing the sensitivity of cancer cells to the cytotoxic effects of radiotherapy and/or chemotherapy comprising contacting the cell with one or more of the HDAC inhibitors, and to therapeutic methods of treating conditions and diseases wherein inhibition of HDAC provides a benefit, for example, a cancer, an inflammation, a neurological disease, a neurodegenerative disorder, stroke, traumatic brain injury, allograft rejection, autoimmune diseases, and malaria, comprising administering a therapeutically effective amount of a present HDAC inhibitor to an individual in need thereof.

BACKGROUND OF THE INVENTION

Inhibitors of HDACs modulate transcription and induce cell growth arrest, differentiation, and apoptosis. HDAC inhibitors (HDACIs) also enhance the cytotoxic effects of therapeutic agents used in cancer treatment, including radiation and chemotherapeutic drugs. Moreover, recent research indicates that transcriptional dysregulation may contribute to the molecular pathogenesis of certain neurodegenerative disorders, such as Huntington's disease, spinal muscular atrophy, amyotropic lateral sclerosis, and ischemia. For example, suberoylanilide hydroxamic acid (SAHA) has been shown to penetrate into the brain to dramatically improve motor impairment in a mouse model of Huntington's disease, thereby validating research directed to HDACIs in the treatment of neurodegenerative diseases.

A recent review summarized evidence that aberrant histone acetyltransferase (HAT) and HDAC activity may be a common underlying mechanism contributing to neurodegeneration. Moreover, from a mouse model of depression, the therapeutic potential of HDACs in treating depression is discussed. See WO 2008/019025, designating the United States, incorporated herein in its entirety.

Eleven isozymes in the HDAC family of enzymes, which can be grouped into classes by their evolutionary relationships, have been identified. Structure and function appear to be conserved among members of the various classes. The HDAC family is made up of class I HDACs, including HDAC1, 2, 3, and 8; class IIa, including HDAC4, 5, 7, and 9; class IIb, including HDAC6 and 10; and a class IV enzyme, HDAC11 (A. J. de Ruijter et al., *The Biochemical Journal* 2003, 370(Pt), 737-749).

The class I HDACs are found primarily in the nucleus and are expressed in all tissue types, except for the muscle cell-specific HDAC8. The class I HDACs interact with many key transcription factors regulating gene expression, including CoREST and NuRD. Class IIa HDACs have tissue specific expression, and are found in both the nucleus and cytoplasm. Unlike the other isozymes, the class IIb HDAC6 does not extensively associate with transcription factors, and acts as a deacetylase on non-histone proteins, including $\alpha$-tubulin and HSP90 (O. Witt et al., *Cancer Letters* 2008).

HDACs form multiprotein complexes with many regulatory proteins inside the cell. For example, HDAC4, 5, and 7 actually lack intrinsic deacetylase ability, and gain activity only by interacting with HDAC3. Each isozyme interacts with a specific series of regulatory proteins and transcription factors and has a specific set of substrates, and thus each regulates a specific series of genes and proteins (O. Witt et al., *Cancer Letters* 2008). The design of selective HDAC isozyme inhibitors allows preferential inhibition of only the isozyme(s) relevant to a particular disease or condition, thereby reducing the probability of counterproductive and/or adverse effects resulting from an unwanted and undesired inhibition of other HDAC isozymes.

HDAC6 is the most abundant histone deacetylase isozyme in the human body, and along with HDAC7, is the most commonly expressed isozyme in the brain (A. J. de Ruijter et al., *The Biochemical Journal* 2003, 370(Pt), 737-749). HDAC6 is unique in that it does not form multiprotein complexes. Structurally significant features of HDAC6 include two deacetylase domains and a zinc finger motif. It is most commonly found in the cytoplasm, but can be shuttled into the nucleus via its nuclear export signal. A cytoplasmic retention signal, which sequesters the enzyme in the cytoplasm, also was found (A. Valenzuela-Fernandez et al., *Trends in Cell Biology* 2008, 18(6), 291-297). The functions of HDAC6 are unlike any of the other HDAC isozymes. Many non-histone substrates are deacetylated by HDAC6, including $\alpha$-tubulin, HSP90, cortactin, and peroxiredoxins (O. Witt et al., *Cancer Letters* 2008; R. B. Parmigiani et al., *PNAS USA* 2008, 105 (28), 9633-9638).

The design of HDACIs focuses on the three major domains of the enzyme molecule. A zinc binding group (ZBG) of the HDACI typically is a hydroxamic acid, benzamide, or thiol, although other functional groups have been used. This ZBG moiety of the inhibitor chelates the zinc cofactor found in the active site of the enzyme. The ZBG moiety typically is bonded to a lipophilic linker group, which occupies a narrow channel leading from the HDAC surface to the active site. This linker, in turn, is bonded to a surface recognition, or 'cap', moiety, which typically is an aromatic group that interacts with residues at the surface of the enzyme (K. V. Butler et al., *Current Pharmaceutical Design* 2008, 14(6), 505-528).

Currently, at least eleven HDACIs are in clinical development. These HDACIs can be divided into at least five chemical classes, illustrated below, based on their structure, and in most cases they broadly and nonselectively inhibit class I/II HDACs with varying efficiency. These five chemical classes are hydroxamates, cyclic tetrapeptides, cyclic peptides, short-chain fatty acids, and benzamides. Typically, known HDACIs fail to show prominent HDAC isozyme selectivity, which as stated above can cause serious problems in a clinical setting, especially in the treatment of diseases and conditions wherein a prolonged drug administration of an HDACI is required. For example, it has been found that some HDACIs enhance lung and microglial inflammation (TSA and SAHA), as well as high glucose-induced inflammation. If this effect is linked to specific HDAC isozymes, the use of certain HDACIs would be contraindicated in various diseases and conditions, such as diabetes and asthma.

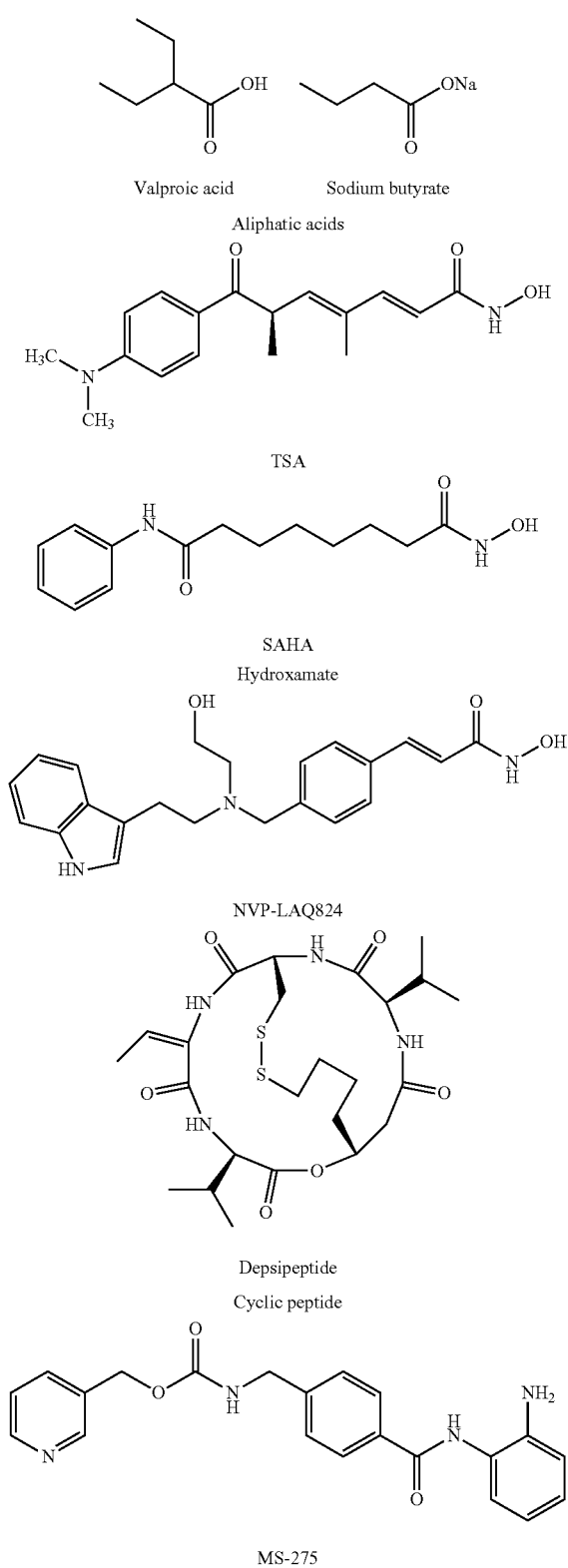
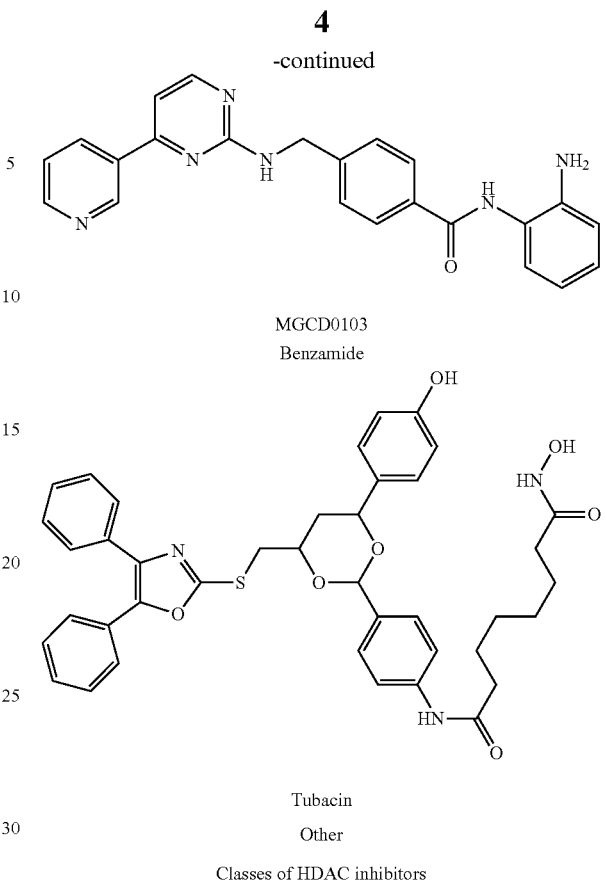

HDAC-regulated factors have been implicated in the mechanisms of major central nervous system (CNS) disorders. In Parkinson's disease (PD), α-synuclein binds to histones and inhibits HAT activity, causing neurodegeneration. Application of HDACIs to PD neurons blocks α-synuclein toxicity. Dysregulation of histone acetylation, involving CBP, a neuroprotective transcription factor with histone acetyltransferase activity, has been found in Huntington's disease (HD), Alzheimer's disease (AD), and Rubinstein-Taybi syndrome (T. Abel et al., Curr. Opin. in Pharmacol. 2008, 8(1), 57-64). In a cellular model of AD, cell death was accompanied by loss of CBP function and histone deacetylation. The mutant HD protein, htt, interacts with CBP, inhibiting the HAT activity and causing cell death. Treatment with an HDACI helps to restore histone acetylation, protecting against neurodegeneration and improving motor performance in a mouse model of HD (C. Rouaux et al., Biochem. Pharmacol. 2004, 68(6), 1157-1164).

Various studies directed to the application of HDACIs in the context of CNS disorders have implicated the class II HDACs, particularly HDAC6, as potential therapeutic targets. One investigation revealed that inhibition of HDAC6 could be beneficial as a treatment for HD, a disease for which no pharmacological treatment is available. The mutant htt protein found in HD disrupts intracellular transport of the pro-survival and pro-growth nerve factor, BDNF, along the microtubule network, causing neuronal toxicity. Inhibition of HDAC6 promotes transport of BDNF by promoting tubulin hyperacetylation. TSA (trichostatin A), a nonselective HDAC inhibitor, was found to facilitate transport and release of BNDF-containing vesicles (J. P. Dompierre et al., J Neurosci 2007, 27(13), 3571-3583). These results provide a biological basis for the identification and development of HDACIs, and particularly HDAC6 selective inhibitors, as a treatment for HD and other neurodegenerative disorders.

HDACIs prevent or delay neuronal dysfunction and death in in vitro and in vivo models thereby indicating that HDACIs are broadly neuroprotective. For example, HDACIs have shown therapeutic efficacy in the polyglutamine-expansion disorder Huntington's disease. While the neuroprotective mechanisms of the HDACIs in rodent models are not yet understood, it is clear that HDACIs induce the expression of certain genes that confer neuroprotection. The upregulation of HSP-70 and Bcl-2 through the inhibition of HDAC has been observed in the cortex and striatum of rats after focal cerebral ischemia. HSP-70 expression has been found to result in neuroprotection in a number of disease models including Alzheimer's disease (AD), Parkinson's disease (PD), and Huntington's disease (HD).

Studies also provide good evidence that HDACI-induced p21cip1/waf1 expression may play a significant role in HDACI-mediated neuroprotection. It recently was reported that p21cip1/waf1 overexpression protects neurons from oxidative stress-induced death, that p21cip1/waf1 is induced in the rodent brain by HDAC inhibition, and that homozygous loss of p21cip1/waf1 exacerbates damage in a mouse MCAO/reperfusion model of ischemic stroke. In a similar study, the HDAC inhibitor TSA was shown to increase gelsolin expression in neurons, and that gelsolin expression is necessary for neuroprotection in an oxygen/glucose deprivation model of neurodegeneration and a mouse MCAO/reperfusion model of ischemic stroke.

Alternatively, unrelated to histone acetylation and gene upregulation, proteins such as alpha-tubulin and HSP90 are targets for acetylation and become acetylated when HDACs are inhibited. In tumor cells, the acetylation of HSP90 has been shown to decrease HSP90 ability to interact with certain client proteins and thereby abrogate chaperone function. With regard to stroke and traumatic brain injury (TBI), as well as several other neurodegenerative diseases, the inhibition of HSP90 is predicted to have a positive effect on neuronal survival. Indeed, the pharmacological HSP90 inhibitor, Geldanamycin, and its analogs have been shown to be neuroprotective in a number of stroke models. HSP90 inhibition and the consequent release of heat-shock factor (HSF) to the nucleus may also, in part, explain an upregulation of HSP70 in the brain during focal ischemia and HDACI treatment.

In addition, HDACIs are useful in the treatment of cancers. For example, histone acetylation and deacetylation play important roles in chromatin folding and maintenance (Kornberg et al., Bjorklund et al., *Cell*, 1999, 96:759-767; Struhl et al., *Cell*, 1998, 94:1-4). Acetylated chromatin is more open and has been implicated in the increased radiation sensitivities observed in some cell types (Oleinick et al., *Int. J. Radiat. Biol.* 1994, 66:523-529). Furthermore, certain radiation-resistant human cancer cells treated with the HDACI inhibitor TSA were sensitized to the damaging effects of ionizing radiation. Thus, HDACIs appear useful as radiation sensitizing agents.

WO 2008/055068, designating the U.S. and incorporated herein in its entirety, discloses numerous diseases and conditions treatable by HDACIs, including the underlying science and reasoning supporting such treatments.

HDAC6 therefore has emerged as an attractive target for drug development and research. (C. M. Grozinger et al., *Proc. Natl. Acad. Sci. USA* 1999, 96, 4868-73; and C. Boyault et al., *Oncogene* 2007, 26, 5468-76.) Presently, HDAC6 inhibition is believed to offer potential therapies for autoimmunity, cancer, and many neurodegenerative conditions. (S. Minucci et al., *Nat. Rev. Cancer.* 2006, 6, 38-51; L. Wang et al., *Nat. Rev. Drug Discov.* 2009, 8, 969-81; J. P. Dompierre et al., *J. Neurosci.* 2007, 27, 3571-83; and A. G. Kazantsev et al., *Nat. Rev. Drug Discov.* 2008, 7, 854-68.) Selective inhibition of HDAC6 by small molecule or genetic tools has been demonstrated to promote survival and re-growth of neurons following injury, offering the possibility for pharmacological intervention in both CNS injury and neurodegenerative conditions. (M. A. Rivieccio et al., *Proc. Natl. Acad. Sci. USA* 2009, 106, 19599-604.) Unlike other histone deacetylases, inhibition of HDAC6 does not appear to be associated with any toxicity, making it an excellent drug target. (O. Witt et al., *Cancer Lett* 2009, 277, 8-21.) Tubacin, an HDAC6 selective inhibitor, and used in models of disease, has helped to validate, in part, HDAC6 as a drug target, but its non-drug-like structure, high lipophilicity (ClogP=6.36 (KOWWIN)), and tedious synthesis make it more useful as a research tool than a drug. (S. Haggarty et al., *Proc. Natl. Acad. Sci. USA* 2003, 100, 4389-94.) Other compounds also have a modest preference for inhibiting HDAC6. (S. Schafer et al., *Chem Med Chem* 2009, 4, 283-90; Y. Itoh et al., *J. Med. Chem.* 2007, 50, 5425-38; and S. Manku et al., *Bioorg. Med. Chem. Lett.* 2009, 19, 1866-70.)

In summary, extensive evidence supports a therapeutic role for HDACIs in the treatment of a variety of conditions and diseases, such as cancers and CNS diseases and degenerations. However, despite exhibiting overall beneficial effects, like beneficial neuroprotective effects, for example, HDACIs known to date have little specificity with regard to HDAC inhibition, and therefore inhibit all zinc-dependent histone deacetylases. It is still unknown which is the salient HDACI(s) that mediate(s) neuroprotection when inhibited. Emerging evidence suggests that at least some of the HDAC isozymes are absolutely required for the maintenance and survival of neurons, e.g., HDAC1. Additionally, adverse side effect issues have been noted with nonspecific HDAC inhibition. Thus, the clinical efficacy of present-day nonspecific HDACIs for stroke, neurodegenerative disorders, neurological diseases, and other diseases and conditions ultimately may be limited. It is important therefore to design, synthesize, and test compounds capable of serving as potent, and preferably isozyme-selective, HDACIs that are able to ameliorate the effects of neurological disease, neurodegenerative disorder, traumatic brain injury, cancer, inflammation, malaria, autoimmune diseases, immunosuppressive therapy, and other conditions and diseases mediated by HDACs.

An important advance in the art would be the discovery of HDACIs, and particularly selective HDAC6 inhibitors, that are useful in the treatment of diseases wherein HDAC inhibition provides a benefit, such as cancers, neurological diseases, traumatic brain injury, neurodegenerative disorders, stroke, malaria, allograft rejection, rheumatoid arthritis, and inflammations. Accordingly, a significant need exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention relates to HDACIs, pharmaceutical compositions comprising the HDACIs, and methods of treating diseases and conditions wherein inhibition of HDAC provides a benefit, such as a cancer, a neurological disease, a neurodegenerative disorder, stroke, an inflammation, traumatic brain injury, rheumatoid arthritis, allograft rejection, autoimmune diseases, and malaria, comprising administering a therapeutically effective amount of an HDACI to an individual in need thereof. The present invention also relates to a method of increasing the sensitivity of a cancer cell to radiotherapy and/or chemotherapy. In some embodiments, the present HDACIs exhibit selectivity for particular HDAC isozymes, such as HDAC6, over other HDAC isozymes.

More particularly, the present invention relates to HDACIs having a structural formula (I):

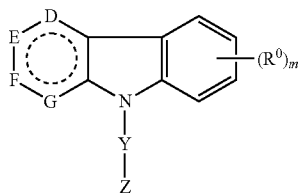
(I)

wherein ring

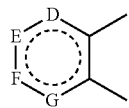

is an aliphatic or aromatic five- or six-membered ring;

D, E, and F, independently, are selected from the group consisting of $C(R^a)_2$, O, S, and $NR^a$;

G is selected from the group consisting of null, $C(R^a)_2$, O, S, $NR^a$, $C(R^a)_2$—$C(R^a)_2$, $NR^a$—$C(R^a)_2$, $NR^a$—$NR^a$, $C(R^a)_2$—O, and $C(R^a)_2$—S;

$R^0$, independently, is selected from the group consisting of $C_{1-6}$alkyl, $C_{1-6}$heteroalkyl, $C_{2-6}$alkenyl, $C_{1-6}$ perfluoroalkyl, $C_{1-6}$perfluoroalkoxy, aryl, heteroaryl, $C_{3-10}$cycloalkyl, $C_{3-8}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl,

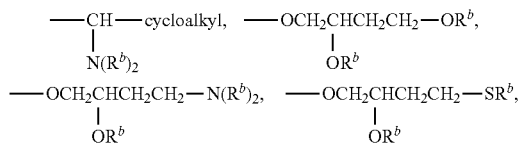

$OR^b$, halo, $N(R^b)_2$, $SR^b$, $SOR^b$, $SO_2R^b$, CN, $C(=O)R^b$, $OC(=O)R^b$, $C(=O)OR^b$, $C_{1-6}$alkyleneN$(R^b)_2$, $C_{1-6}$alkyleneOR$^b$, $C_{1-6}$alkyleneSR$^b$, $C_{1-6}$alkyleneC(=O)OR$^b$, $C(=O)N(R^b)_2$, $C(=O)NR^bC_{1-6}$alkyleneOR$^b$, $OC_{1-6}$alkyleneC(=O)OR$^b$, $OC_{1-6}$alkyleneN$(R^b)_2$, $OC_{1-6}$alkyleneOR$^b$, $OC_{1-6}$alkyleneNR$^b$C(=O)OR$^b$, $NR^bC_{1-6}$alkyleneN$(R^b)_2$, $NR^bC(=O)R^b$, $NR^bC(=O)N(R^b)_2$, $N(SO_2C_{1-6}$alkyl$)_2$, $NR^b(SO_2C_{1-6}$alkyl), nitro, and $SO_2N(R^b)_2$;

m is an integer 0, 1, 2, 3, or 4;

$R^a$, independently, is selected from the group consisting of null, hydrogen, $C_{1-6}$alkyl, $C_{2-6}$alkenyl, $C_{1-6}$heteroalkyl, aryl, heteroaryl, $C_{3-8}$cycloalkyl, $C_{3-10}$heterocycloalkyl, $C_{1-6}$alkylenearyl, $C_{1-6}$alkyleneheteroaryl, $C_{1-6}$alkyleneC(=O)OR$^b$, $C_{1-6}$alkyleneC(=O)R$^b$, $C_{1-6}$alkyleneC(=O)N(R$^b$)$_2$, $C(=O)R^b$, $C(=O)N(R^b)_2$, $C(=O)OR^b$, CN, $OR^b$, halo, $N(R^b)_2$, $SR^b$, $SOR^b$, $SO_2R^b$, $CF_3$, $OCF_3$, $NO_2$, $OC(=O)R^b$, $OC_{1-6}$alkyleneC(=O)OR$^b$, $C_{1-6}$alkyleneOC$_{1-6}$alkyleneC(=O)OR$^b$, $C(=O)NR^bSO_2R^b$, $C(=O)C_{1-6}$alkylenearyl, $C_{1-6}$alkyleneN$(R^b)_2$, $C_{1-6}$alkyleneOR$^b$, $C_{1-6}$alkyleneSR$^b$, $C(=O)NR^bC_{1-6}$alkyleneOR$^b$, $OC_{1-6}$alkyleneN$(R^b)_2$, $OC_{2-6}$alkyleneOR$^b$, $OC_{2-6}$alkyleneNR$^b$C(=O)OR$^b$, $NR^bC_{1-6}$alkyleneN$(R^b)_2$, $NR^bC(=O)R^b$, $NR^bC(=O)N(R^b)_2$, $N(SO_2C_{1-6}$alkyl$)_2$, $NR^b(SO_2C_{1-6}$alkyl), $SO_2N(R^b)_2$, and $OSO_2CF_3$;

$R^b$, independently, is selected from the group consisting of hydrogen, $C_{1-6}$alkyl, $C_{1-6}$heteroalkyl, $C_{1-6}$alkyleneNH$_2$, $C_{1-6}$alkyleneNH$(C_{1-6}$alkyl), $C_{1-6}$alkyleneN$(C_{1-6}$alkyl$)_2$, $C_{1-6}$alkyleneNH$(C_{1-6}$alkyl$)_2$, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, aryl, heteroaryl, $C_{3-8}$cycloalkyl, and $C_{3-10}$heterocycloalkyl;

Y is selected from the group consisting of null, $C_{1-8}$alkylene, $R^a$ substituted $C_{1-8}$alkylene, $NR^b$, $C(=O)$, aryl, $C(=O)$ aryl, $C(=O)C_{1-6}$alkylene, $C_{1-8}$alkyleneNR$^b$, $C_{1-6}$alkylenearyleneC$_{1-6}$alkylene, $C_{2-6}$alkenylene, $C_{4-8}$alkdienylene, $C_{1-6}$alkylenearylene, $C_{1-6}$alkyleneheteroarylene, $R^a$ substituted $C_{1-6}$alkyleneheteroarylene, and $C_{2-6}$alkenylenearyleneC$_{1-6}$alkylene;

Z is selected from the group consisting of —C(=O)N(R$^c$)OH,
—O(CH$_2$)$_{1-6}$C(=O)N(R$^c$)OR$^b$,
—N(R$^c$)(CH$_2$)$_{1-6}$C(=O)N(R$^c$)OR$^c$,
arylC(=O)NHOH,
—N(OH)C(=O)R$^c$,
heteroarylC(=O)NHOH,

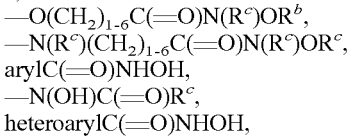

—B(OR$^c$)$_2$,
—SO$_2$NHR$^c$,
—NHSO$_2$NHR$^c$,
—NHSO$_2$C$_{1-6}$alkyl,
—SO$_2$C$_{1-6}$alkyl,
—P(=O)(OR$^g$)$_2$, wherein R$^g$ independently is hydrogen, methyl, or ethyl,
—NH—P(=O)(OR$^g$)$_2$,

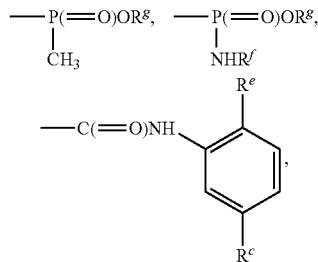

—C(=O)R$^f$ wherein R$^f$ is selected from the group consisting of OH, N(R$^c$)$_2$, NH(OCH$_3$), N(CH$_3$)OH, $C_{1-6}$alkyl, $CF_3$, aryl, heteroaryl, $C_{3-8}$cycloalkyl, NHSO$_2$CH$_3$, NHSO$_2$CF$_3$, and $C_{1-6}$haloalkyl,
—C(=O)(C(R$^c$)$^2$)$_{1-6}$SH,
—C(=O)C(=O)NHR$^c$,
—C(=O)NHN(R$^c$)$_2$,
—C(=O)NH(CH$_2$)$_{1-3}$N(R$^c$)$_2$,
—SR$^d$ wherein R$^d$ is hydrogen or (C=O)CH$_3$,

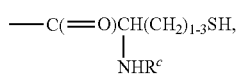

—S—(C═O)C$_{1-6}$alkyl,

C$_{3-10}$heterocycloalkyl optionally substituted with oxo (═O), thioxo (═S), or both, aryl optionally substituted with one or more of C$_{1-6}$alkyl, —C(═O)R$^e$, —NH$_2$, and —SH, heteroaryl optionally substituted with —NH$_2$, —SH, or both, —N(H)C(═O)SH,
—NHC(═O)NHR$^e$,
—NHC(═O)CH$_2$R$^e$,
—NHC(═O)(CH$_2$)$_{1-6}$SH,
—NHC(═O)CH$_2$Hal,
—NHC(═S)NHR$^e$,
—NHC(═S)CH$_2$R$^e$,
—C(═S)NHR$^e$,
—C(═S)CH$_2$R$^e$,
—NHC(═S)CH$_2$R$^e$,
—NHC(═S)CH$_2$Hal, and
—(C═O)C$_{1-6}$alkyl;

R$^c$, independently, is selected from the group consisting of hydrogen, (C═O)CH$_3$, C$_{1-6}$alkyl, CF$_3$, CH$_2$F, and aryl, or two R$^c$ groups are taken together with the carbon to which they attached to form a C$_{3-8}$cycloalkyl group; and R$^e$ is NH$_2$ or OH;

or a pharmaceutically acceptable salt, hydrate, or prodrug thereof.

In another embodiment, the present invention provides a method of treating a condition or disease by administering a therapeutically effective amount of an HDACI of structural formula (I) to an individual in need thereof. The disease or condition of interest is treatable by inhibition of HDAC, for example, a cancer, a neurodegenerative disorder, a traumatic brain injury, a neurological disease, an inflammation, stroke, an autoimmune disease, allograft rejection, and malaria.

The present HDACIs contain a bidentate chelate as the ZBG. Preferably, a present HDACI contains a relatively short linker group between the ZBG and the aromatic surface recognition group, e.g., contains a 0 to 5 carbon atom chain. The aromatic surface recognition group is a tricyclic moiety, such as carbazole, i.e.,

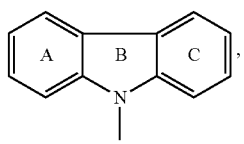

or

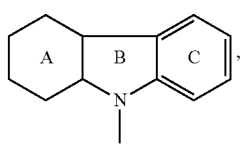

wherein the A ring can be aliphatic or aromatic, carbocyclic or heterocyclic, and 5-, 6-, or 7-membered. Either or both of A and C rings can be substituted, independently, with one to four substituents.

It has been found that a degree of isoform selectivity for an HDACI can be achieved by manipulating the surface recognition group in concert with the ZBG. In particular, a combination of steric and electronic properties of the surface recognition group modulates the ability of the compounds to target different isoforms via interactions with an HDAC surface. Such considerations led to the present HDACIs having a carbazole-type surface recognition group that exhibits selectivity in the inhibition of HDAC6.

Another embodiment of the present invention provides a method of treating a cancer comprising administering to an individual in need thereof, such as a human, a therapeutically effective amount of an HDACI of structural formula (I). The HDACI of structural formula (I) can be administered as the sole anticancer therapy, or in conjunction with a therapeutically effective amount of a second anticancer agent, such as radiation and/or chemotherapy.

Another embodiment of the present invention provides a method of increasing the sensitivity of a cancer cell to the cytotoxic effects of radiotherapy and/or chemotherapy comprising contacting the cell with an effective amount of an HDACI of structural formula (I). In certain embodiments, the cell is an in vivo cell.

In another embodiment, the present invention provides a method of treating a neurological disease comprising administering to an individual in need thereof, such as a human, a therapeutically effective amount of an HDACI of structural formula (I). The present invention also relates to a method of treating neurodegenerative disorders and traumatic brain injuries comprising administering a therapeutically effective amount of an HDACI of the structural formula (I) to an individual in need thereof. In each embodiment, a present HDACI can be the sole therapeutic agent or can be administered with additional therapeutic agents known to treat the disease or condition of interest.

The present invention also provides a method of treating malaria and other parasitic infections comprising administering a therapeutically effective amount of an HDACI of structural formula (I) to an individual in need thereof. In certain embodiments, the individual is a human. In certain embodiments, said method further comprises optionally coadministering a second antimalarial compound (e.g., chloroquine).

In yet another embodiment, the present invention provides a method of inducing immunosuppression in an individual comprising administration of a therapeutically effective amount of an HDACI of structural formula (I) to an individual in need thereof, for example, an individual receiving a transplant. This method further comprises optionally coadministering a second immunosuppressant (e.g., cyclosporin).

In still another embodiment, the present invention provides a method of treating inflammatory diseases and conditions, e.g., arthritis and rheumatic diseases, comprising administration of a therapeutically effective amount of an HDACI of structural formula (I) to an individual in need thereof. The method further contemplates optional coadministration of a second anti-inflammatory drug.

In another embodiment, the present invention also provides a pharmaceutical composition comprising an HDACI of structural formula (I) and a pharmaceutically acceptable excipient.

Another embodiment of the present invention is to utilize an HDACI comprising a compound of structural formula (I) and an optional second therapeutically active agent in a method of treating an individual for a disease or condition wherein inhibition of HDAC provides a benefit.

In a further embodiment, the invention provides for use of a composition comprising an HDACI of structural formula (I)

and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising an HDACI of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

The HDACI of structural formula (I) and the second therapeutic agent can be administered together as a single-unit dose or separately as multi-unit doses, wherein the HDACI of structural formula (I) is administered before the second therapeutic agent, or vice versa. It is envisioned that one or more dose of an HDACI of structural formula (I) and/or one or more dose of a second therapeutic agent can be administered.

In one embodiment, an HDACI of structural formula (I) and a second therapeutic agent are administered simultaneously. In related embodiments, an HDACI of structural formula (I) and second therapeutic agent are administered from a single composition or from separate compositions. In a further embodiment, an HDACI of structural formula (I) and a second therapeutic agent are administered sequentially. An HDACI of structural formula (I) can be administered in an amount of about 0.005 to about 500 milligrams per dose, about 0.05 to about 250 milligrams per dose, or about 0.5 to about 100 milligrams per dose.

Compounds of the invention inhibit HDAC and are useful research tools for in vitro study of histone deacetylases and their role in biological processes.

These and other novel aspects of the present invention will become apparent from the following detailed description of the preferred embodiments.

DETAILED DESCRIPTION OF THE PREFERRED EMBODIMENTS

Figure 1A:
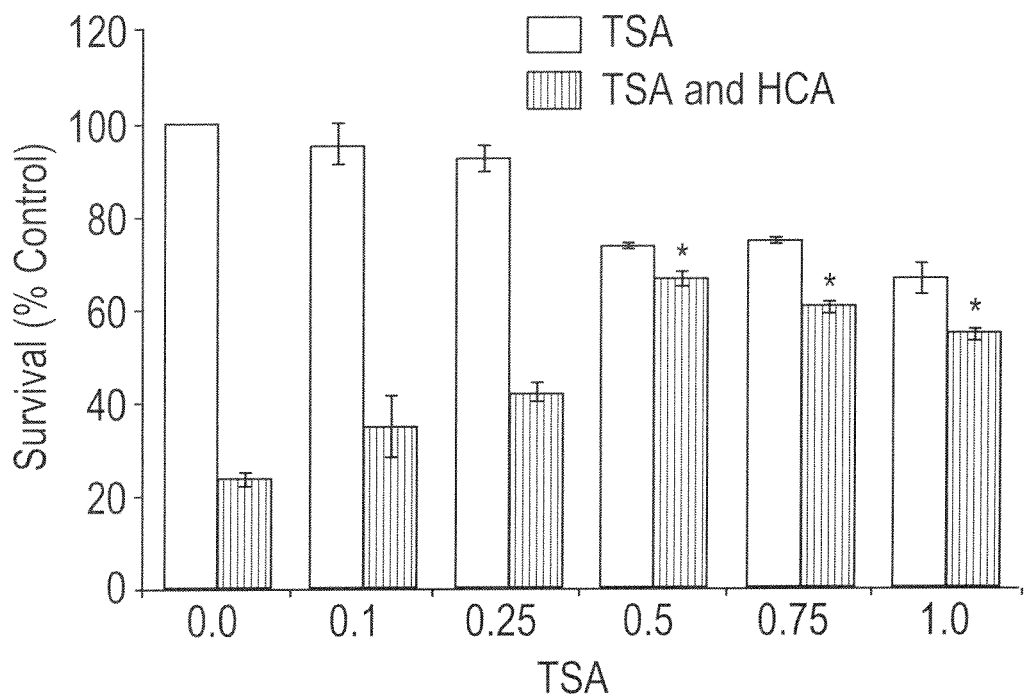
FIGS. 1A and 1B contain bar graphs of concentrations of TSA (FIG. 1A) or compound 6 (FIG. 1B) vs. survival (% control) for the HCA oxidative stress assay.

The present invention is directed to novel HDACIs and their use in therapeutic treatments of, for example, cancers, inflammations, traumatic brain injuries, neurodegenerative disorders, neurological diseases, strokes, autoimmune diseases, inflammatory diseases, and malaria. The present HDACIs also increase the sensitivity of a cancer cell to the cytotoxic effects of radiotherapy and/or chemotherapy. In some embodiments, the present HDACIs selectively inhibit HDAC6 over other HDAC isozymes.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "a disease or condition wherein inhibition of HDAC provides a benefit" pertains to a condition in which HDAC and/or the action of HDAC is important or necessary, e.g., for the onset, progress, expression of that disease or condition, or a disease or a condition which is known to be treated by an HDAC inhibitor (such as, e.g., TSA, pivaloyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration), inflammatory diseases (e.g., osteoarthritis, rheumatoid arthritis), diseases involving angiogenesis (e.g., cancer, rheumatoid arthritis, psoriasis, diabetic retinopathy), hematopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC for any particular cell type, for example, by assays which conveniently can be used to assess the activity of particular compounds.

The term "second therapeutic agent" refers to a therapeutic agent different from an HDACI of structural formula (I) and that is known to treat the disease or condition of interest. For example when a cancer is the disease or condition of interest, the second therapeutic agent can be a known chemotherapeutic drug, like taxol, or radiation, for example.

The term "HDAC" refers to a family of enzymes that remove acetyl groups from a protein, for example, the ε-amino groups of lysine residues at the N-terminus of a histone. The HDAC is a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling in the target cells; and/or relieve, to some extent, one or more of the symptoms associated with the cancer. To extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, an HDACI of structural formula (I) can be administered at the same time or sequentially in any order at different points in time as a second therapeutic agent. A present HDACI and the second therapeutic agent can be administered separately, in any appropriate form and by any suitable route. When a present HDACI and the second therapeutic agent are not administered concurrently, it is understood that they can be administered in any order to a subject in need thereof. For example, a present HDACI can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, an HDACI of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

In particular, the present invention is directed to HDACIs of structural formula (I), compositions comprising a compound of structural formula (I), and therapeutic uses of compounds of structural formula (I):

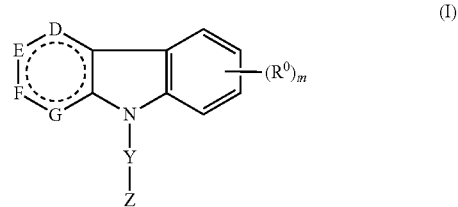

(I)

wherein ring

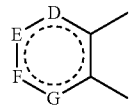

is an aliphatic or aromatic five- or six-membered ring;

D, E, and F, independently, are selected from the group consisting of $C(R^a)_2$, O, S, and $NR^a$;

G is selected from the group consisting of null, $C(R^a)_2$, O, S, $NR^a$, $C(R^a)_2$—$C(R^a)_2$, $NR^a$—$C(R^a)_2$, $NR^a$—$NR^a$, $C(R^a)_2$—O, and $C(R^a)_2$—S;

$R^0$, independently, is selected from the group consisting of $C_{1-6}$alkyl, $C_{1-6}$heteroalkyl, $C_{2-6}$alkenyl, $C_{1-6}$ perfluoroalkyl, $C_{1-6}$ perfluoroalkoxy, aryl, heteroaryl, $C_{3-10}$cycloalkyl, $C_{3-8}$heterocycloalkyl, $C_{1-6}$alkylenearyl, $C_{1-6}$alkyleneheteroaryl, $C_{1-6}$alkyleneheterocycloalkyl, $C_{1-6}$alkylenecycloalkyl, —CH—cycloalkyl,   —OCH$_2$CHCH$_2$CH$_2$—OR$^b$,
  |                              |
  N(R$^b$)$_2$                  OR$^b$ —OCH$_2$CHCH$_2$CH$_2$—N(R$^b$)$_2$,   —OCH$_2$CHCH$_2$CH$_2$—SR$^b$,
  |                                            |
  OR$^b$                                       OR$^b$ OR$^b$, halo, N(R$^b$)$_2$, SR$^b$, SOR$^b$, SO$_2$R$^b$, CN, C(=O)R$^b$, OC(=O)R$^b$, C(=O)OR$^b$, $C_{1-6}$alkyleneN(R$^b$)$_2$, $C_{1-6}$alkyleneOR$^b$, $C_{1-6}$alkyleneSR$^b$, $C_{1-6}$alkyleneC(=O)OR$^b$, C(=O)N(R$^b$)$_2$, C(=O)NR$^b$C$_{1-6}$alkyleneOR$^b$, OC$_{1-6}$alkyleneC (=O)OR$^b$, OC$_{1-6}$alkyleneN(R$^b$)$_2$, OC$_{1-6}$alkyleneOR$^b$, OC$_{1-6}$alkyleneNR$^b$C(=O)OR$^b$, NR$^b$C$_{1-6}$alkyleneN(R$^b$)$_2$, NR$^b$C(=O)R$^b$, NR$^b$C(=O)N(R$^b$)$_2$, N(SO$_2$C$_{1-6}$alkyl)$_2$, NR$^b$(SO$_2$C$_{1-6}$alkyl), nitro, and SO$_2$N(R$^b$)$_2$;

m is an integer 0, 1, 2, 3, or 4;

R$^a$, independently, is selected from the group consisting of null, hydrogen, C$_{1-6}$alkyl, C$_{2-6}$alkenyl, C$_{1-6}$heteroalkyl, aryl, heteroaryl, C$_{3-8}$cycloalkyl, C$_{3-10}$heterocycloalkyl, C$_{1-6}$alkylenearyl, C$_{1-6}$alkyleneheteroaryl, C$_{1-6}$alkyleneC(=O)OR$^b$, C$_{1-6}$alkyleneC(=O)R$^b$, C$_{1-6}$alkyleneC(=O)N(R$^b$)$_2$, C(=O)R$^b$, C(=O)N(R$^b$)$_2$, C(=O)OR$^b$, CN, OR$^b$, halo, N(R$^b$)$_2$, SR$^b$, SOR$^b$, SO$_2$R$^b$, CF$_3$, OCF$_3$, NO$_2$, OC(=O)R$^b$, OC$_{1-6}$alkyleneC(=O)OR$^b$, C$_{1-6}$alkyleneOC$_{1-6}$alkyleneC(=O)OR$^b$, C(=O)NR$^b$SO$_2$R$^b$, C(=O)C$_{1-6}$alkylenearyl, C$_{1-6}$alkyleneN(R$^b$)$_2$, C$_{1-6}$alkyleneOR$^b$, C$_{1-6}$alkyleneSR$^b$, C(=O)NR$^b$C$_{1-6}$alkyleneOR$^b$, OC$_{1-6}$alkyleneN(R$^b$)$_2$, OC$_{2-6}$alkyleneOR$^b$, OC$_{2-6}$alkyleneNR$^b$C(=O)OR$^b$, NR$^b$C$_{1-6}$alkyleneN(R$^b$)$_2$, NR$^b$C(=O)R$^b$, NR$^b$C(=O)N(R$^b$)$_2$, N(SO$_2$C$_{1-6}$alkyl)$_2$, NR$^b$(SO$_2$C$_{1-6}$alkyl), SO$_2$N(R$^b$)$_2$, and OSO$_2$CF$_3$;

R$^b$, independently, is selected from the group consisting of hydrogen, C$_{1-6}$alkyl, C$_{1-6}$heteroalkyl, C$_{1-6}$alkyleneNH$_2$, C$_{1-6}$alkyleneNH(C$_{1-6}$alkyl), C$_{1-6}$alkyleneN(C$_{1-6}$alkyl)$_2$, C$_{1-6}$alkyleneNH(C$_{1-6}$alkyl)$_2$, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, aryl, heteroaryl, C$_{3-8}$cycloalkyl, and C$_{3-10}$heterocycloalkyl;

Y is selected from the group consisting of null, C$_{1-8}$alkylene, R$^a$ substituted C$_{1-8}$alkylene, NR$^b$, C(=O), aryl, C(=O)aryl, C(=O)C$_{1-6}$alkylene, C$_{1-8}$alkyleneNR$^b$, C$_{1-6}$alkylenearyleneC$_{1-6}$ alkylene, C$_{2-6}$alkenylene, C$_{4-8}$alkdienylene, C$_{1-6}$alkylenearylene, C$_{1-6}$alkyleneheteroarylene, R$^a$ substituted C$_{1-6}$alkyleneheteroarylene, and C$_{2-6}$alkenylenearyleneC$_{1-6}$alkylene;

Z is selected from the group consisting of —C(=O)N(R$^c$)OH,

—O(CH$_2$)$_{1-6}$C(=O)N(R$^c$)OR$^b$,

—N(R$^c$)(CH$_2$)$_{1-6}$C(=O)N(R$^c$)OR$^c$, arylC(=O)NHOH,

—N(OH)C(=O)R$^c$, heteroarylC(=O)NHOH,

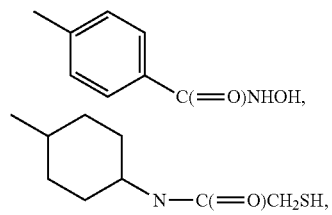

—B(OR$^c$)$_2$,

—SO$_2$NHR$^c$,

—NHSO$_2$NHR$^c$,

—NHSO$_2$C$_{1-6}$alkyl,

—SO$_2$C$_{1-6}$alkyl,

—P(=O)(OR$^g$)$_2$, wherein R$^g$ independently is hydrogen, methyl, or ethyl,

—NH—P(=O)(OR$^g$)$_2$,

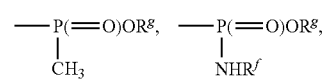

-continued

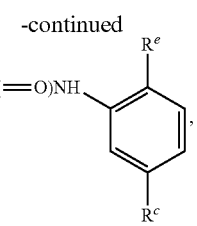

—C(=O)R$^f$ wherein R$^f$ is selected from the group consisting of OH, N(R$^c$)$^2$, NH(OCH$_3$), N(CH$_3$)OH, C$_{1-6}$alkyl, CF$_3$, aryl, heteroaryl, C$_{3-8}$cycloalkyl, NHSO$_2$CH$_3$, NHSO$_2$CF$_3$, and C$_{1-6}$haloalkyl, —C(=O)(C(R$^c$)$^2$)$_{1-6}$SH, —C(=O)C(=O)NHR$^c$, —C(=O)NHN(R$^c$)$_2$, —C(=O)NH(CH$_2$)$_{1-3}$N(R$^c$)$_2$, —SR$^d$ wherein R$^d$ is hydrogen or (C=O)CH$_3$,

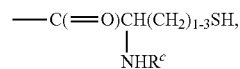

—S—(C=O)C$_{1-6}$alkyl,

C$_{3-10}$heterocycloalkyl optionally substituted with oxo (=O), thioxo (=S), or both, aryl optionally substituted with one or more of C$_{1-6}$alkyl, —C(=O)R$^e$, —NH$_2$, and —SH, heteroaryl optionally substituted with —NH$_2$, —SH, or both,

—N(H)C(=O)SH,

—NHC(=O)NHR$^e$,

—NHC(=O)CH$_2$R$^e$,

—NHC(=O)(CH$_2$)$_{1-6}$SH,

—NHC(=O)CH$_2$Hal,

—NHC(=S)NHR$^e$,

—NHC(=S)CH$_2$R$^e$,

—C(=S)NHR$^e$,

—C(=S)CH$_2$R$^e$,

—NHC(=S)CH$_2$R$^e$,

—NHC(=S)CH$_2$Hal, and

—(C=O)C$_{1-6}$alkyl;

R$^c$, independently, is selected from the group consisting of hydrogen, (C=O)CH$_3$, C$_{1-6}$alkyl, CF$_3$, CH$_2$F, and aryl, or two R$^c$ groups are taken together with the carbon to which they attached to form a C$_{3-8}$cycloalkyl group; and R$^e$ is NH$_2$ or OH;

or a pharmaceutically acceptable salt, hydrate, or prodrug thereof.

The compounds of structural formula (I) inhibit HDAC and are useful in the treatment of a variety of diseases and conditions. In particular, HDACIs of structural formula (I) are used in methods of treating a disease or condition wherein inhibition of HDAC provides a benefit, for example, cancers, neurological diseases, neurodegenerative conditions, autoimmune diseases, inflammatory diseases and conditions, stroke, traumatic brain injury, autism, and malaria. The methods comprise administering a therapeutically effective amount of an HDACI of structural formula (I) to an individual in need thereof.

The present methods also encompass administering a second therapeutic agent to the individual in addition to an HDACI of structural formula (I). The second therapeutic agent is selected from agents, such as drugs and adjuvants, known as useful in treating the disease or condition afflicting the individual, e.g., a chemotherapeutic agent and/or radiation known as useful in treating a particular cancer.

As used herein, the term "alkyl" refers to straight chained and branched saturated hydrocarbon groups, nonlimiting examples of which include methyl, ethyl, and straight chain and branched propyl, butyl, pentyl, hexyl, heptyl, and octyl groups containing the indicated number of carbon atoms. The term $C_n$ means the alkyl group has "n" carbon atoms.

The term "alkylene" refers to a bidentate moiety obtained by removing two hydrogen atoms from an alkane. An "alkylene" is positioned between two other chemical groups and serves to connect them. An example of an alkylene group is —(CH$_2$)$_n$—. An alkyl, e.g., methyl, or alkylene, e.g., —CH$_2$CH$_2$—, group can be substituted, independently, with one or more of halo, trifluoromethyl, trifluoromethoxy, hydroxy, alkoxy, nitro, cyano, alkylamino, and amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkdienylene" is defined identically as "alkenylene" except the group contains two carbon-carbon double bonds, either conjugated or non-conjugated.

The term "heteroalkyl" refers to an alkyl group having one or more, and typically one to three, heteroatoms in the carbon chain of the alkyl group. The heteroatoms, independently, are selected from O, S, and NR, wherein R is hydrogen, alkyl, cycloalkyl, heterocycloalkyl, aryl, and heteroaryl. A term such as "$C_{1-6}$heteroalkyl" means that the group contains 1 to 6 carbon atoms in addition to the heteroatoms.

The term "perfluoroalkyl" is defined as an alkyl group wherein all hydrogen atoms are replaced by fluorine atoms.

As used herein, the term "halo" and "Hal" are defined as fluoro, chloro, bromo, and iodo.

The term "hydroxy" is defined as —OH.

The term "alkoxy" is defined as —OR, wherein R is alkyl. The term "perfluoroalkoxy" is defined as an alkoxy group wherein all hydrogen atoms are replaced by fluorine atoms.

The term "amino" is defined as —NR$_2$, wherein each R group, independently, is hydrogen, alkyl, cycloalkyl, heterocycloalkyl, $C_{1-3}$alkylenearyl, heteroaryl, or aryl, or both R groups are taken together with the N to which they are attached to form a 4 to 8 membered ring.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

The term "Ac" is defined as —C(=O)CH$_3$.

The term "tBu" is defined as tertiary butyl, i.e. —C(CH$_3$)$_3$.

The term "Boc" is defined as tert-butoxycarbonyl.

As used herein, compounds such as

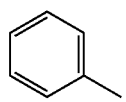

is an abbreviation for

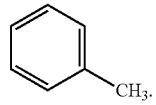

In addition, compounds such as

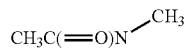

is an abbreviation for

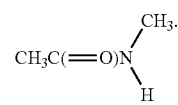

As used herein, groups such as $C_{1-3}$alkylphenyl means a $C_{1-3}$alkyl group bonded to a phenyl ring, for example,

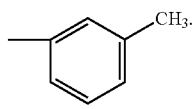

Groups such as $C_{1-3}$alkylenephenyl means a phenyl group bonded to a $C_{1-3}$alkylene group, for example,

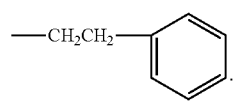

As used herein, the term "aryl" refers to a monocyclic aromatic group, e.g., phenyl. Unless otherwise indicated, an aryl group can be unsubstituted or substituted with one or more, and in particular one to five, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Exemplary aryl groups include, but are not limited to, phenyl, chlorophenyl, methylphenyl, methoxyphenyl, trifluoromethylphenyl, nitrophenyl, 2,4-methoxychlorophenyl, and the like.

The term "arylene" refers to a bidentate aryl group that bonds to two other groups and serves to connect these groups, e.g.,

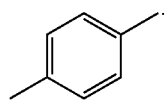

The term "$C_{1-4}$alkylenearylene$C_{1-4}$alkylene" means

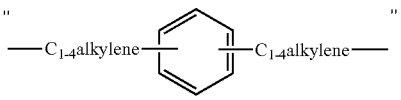

and serves to connect two other groups.

The term "$C_{1-6}$alkylenearylene" means

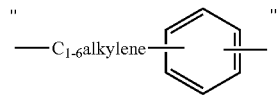

and serves to connect two other groups.

The term "$C_{2-6}$alkenylenearylene$C_{1-4}$alkylene" means

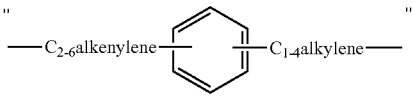

and serves to connect two other groups.

As used herein, the term "heteroaryl" refers to a monocyclic ring system containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl. Examples of heteroaryl groups include, but are not limited to, thienyl, furyl, oxazolyl, thiophenyl, triazolyl, isothiazolyl, isoxazolyl, imidazolyl, pyrimidinyl, thiazolyl, thiadiazolyl, pyridinyl, pyridazinyl, pyrazolyl, pyrazinyl, tetrazolyl, oxazolyl, pyrrolyl, and triazinyl.

As used herein, the term "$C_{3-8}$cycloalkyl" means a monocyclic aliphatic ring containing three to eight carbon atoms, either saturated or unsaturated.

As used herein, the term "heterocycloalkyl" means a monocyclic or a bicyclic aliphatic ring containing 3 to 10 total atoms, either saturated or unsaturated, of which one to five of the atoms are independently selected from nitrogen, oxygen, and sulfur and the remaining atoms are carbon.

In accordance with the present invention, ring

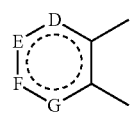

is a five-, six-, or seven-membered, aliphatic or aromatic ring. For example, ring -D-E-F-G- can be

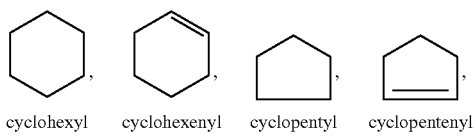

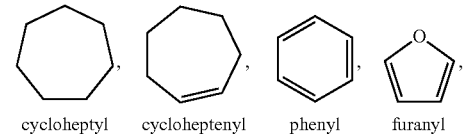

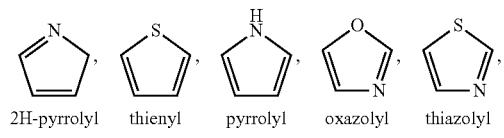

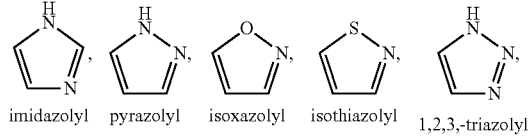

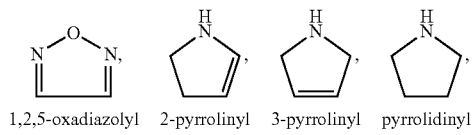

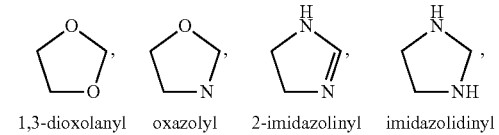

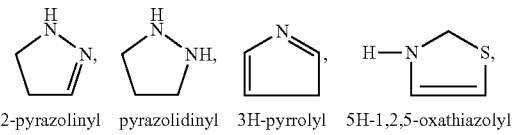

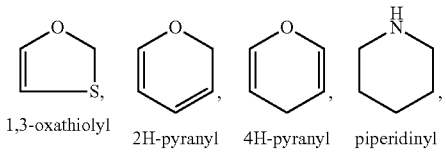

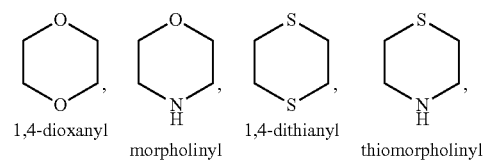

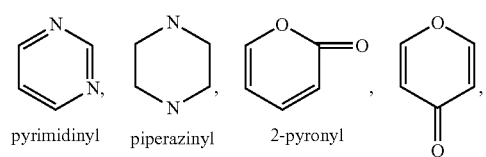

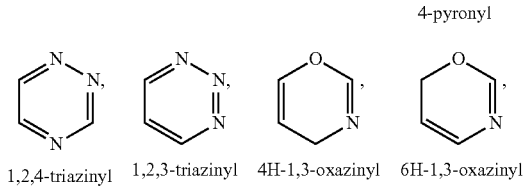

-continued

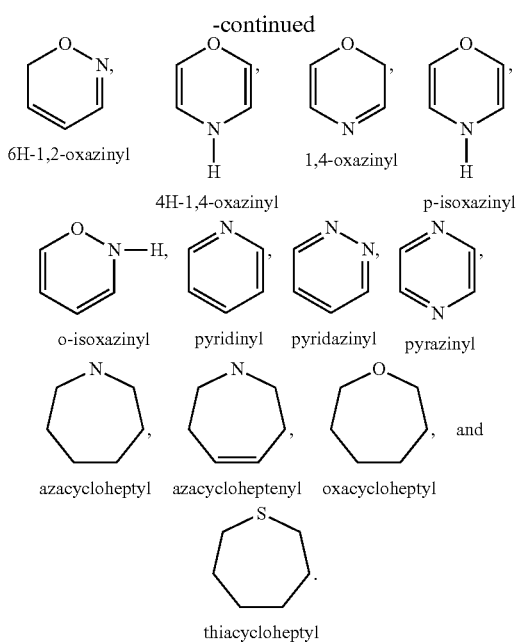

In each of the above ring systems, the hydrogen of an aliphatic nitrogen atom can be replaced by $C_{1-6}$alkyl or aryl.

The above rings can be attached to the middle (B) ring of the tricyclic structure in any possible orientation, for example, piperidinyl can be bonded to the B ring of the tricyclic ring system in any of the following orientations:

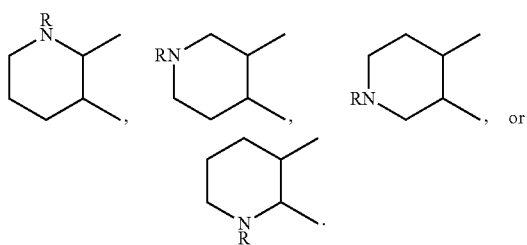

All other -D-E-F-G- rings similarly can be oriented in various configurations with respect to the center B ring of the tricyclic structure.

Nonlimiting examples of the tricyclic moiety

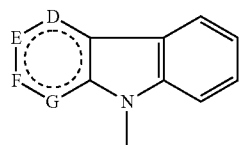

include, but are not limited to, substituted and unsubstituted

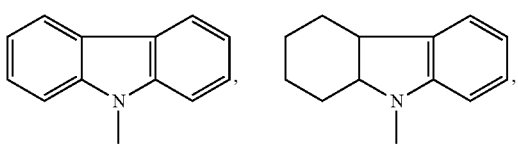

-continued

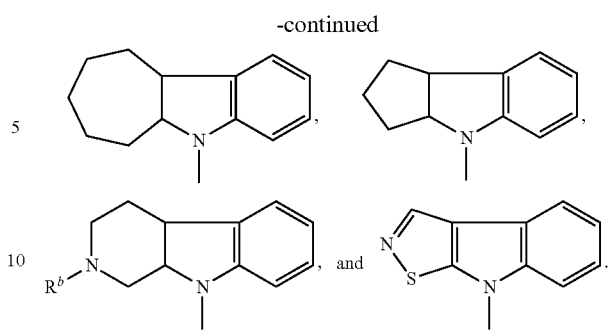

Examples of preferred -D-E-F-G-rings include, but are not limited to,

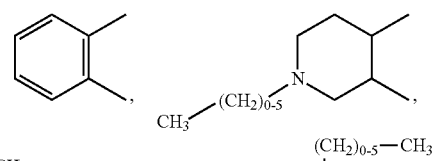

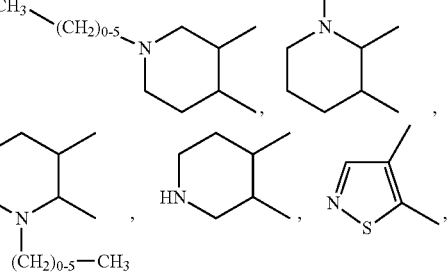

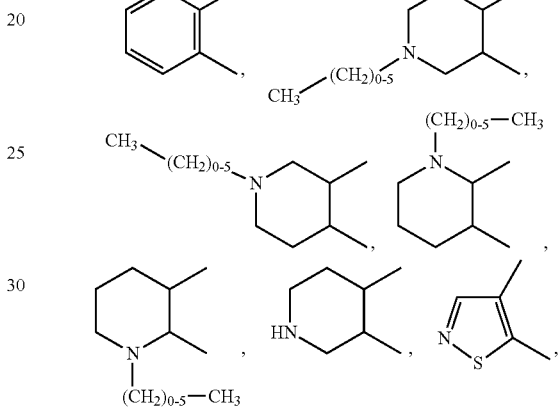

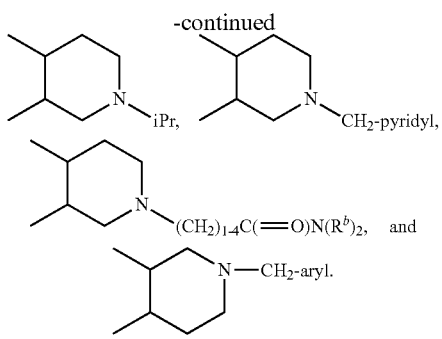

In some embodiments, R° substituents on the phenyl ring, if present at all, preferably are $OR^b$, halo, $C_{1-6}$alkyl, aryl, heterocycloalkyl, —$(CH_2)_{1-4}$heterocycloalkyl,

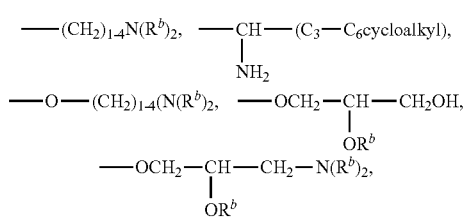

or —$C(=O)N(CH_2)_{1-4}N(R^b)_2$. The integer "m" typically is 0, 1, or 2.

In some embodiments, $R^a$ and $R^b$, independently, are $C_{1-6}$alkyl, halo, $C_{1-3}$alkylenearyl, $C_{1-3}$alkyleneheteroaryl, $C_{1-3}$alkyleneheterocycloalkyl, $C(=O)C_{1-3}$alkyl, $C_{2-6}$alkenyl, BOC, $C_{1-3}$alkyleneC(=O)NH$_2$,

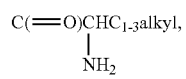

and $C_{1-3}$alkyleneC(=O)OH.

In other preferred embodiments, Y is null, —$(CH_2)_{1-6}$—,

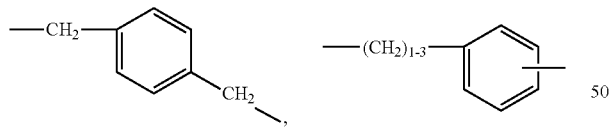

optionally substituted with halo, $CF_3$, or CN,

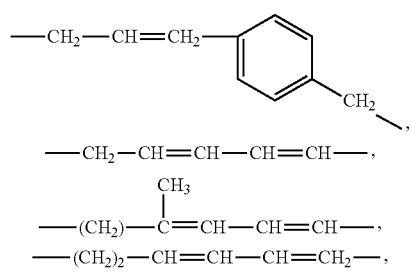

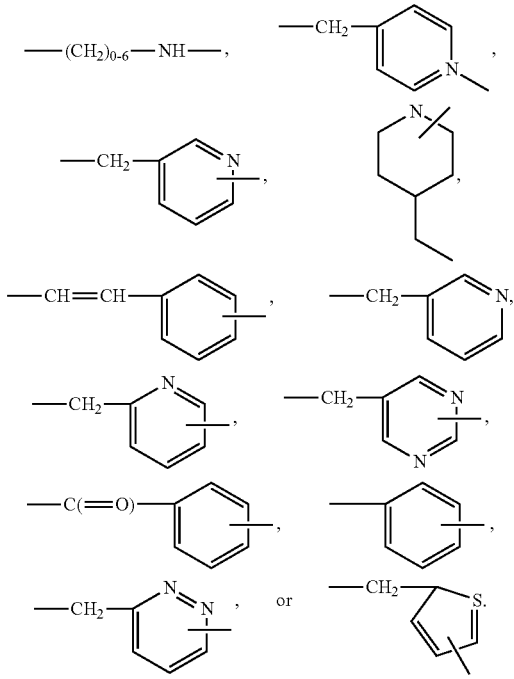

In still other preferred embodiments, Z is

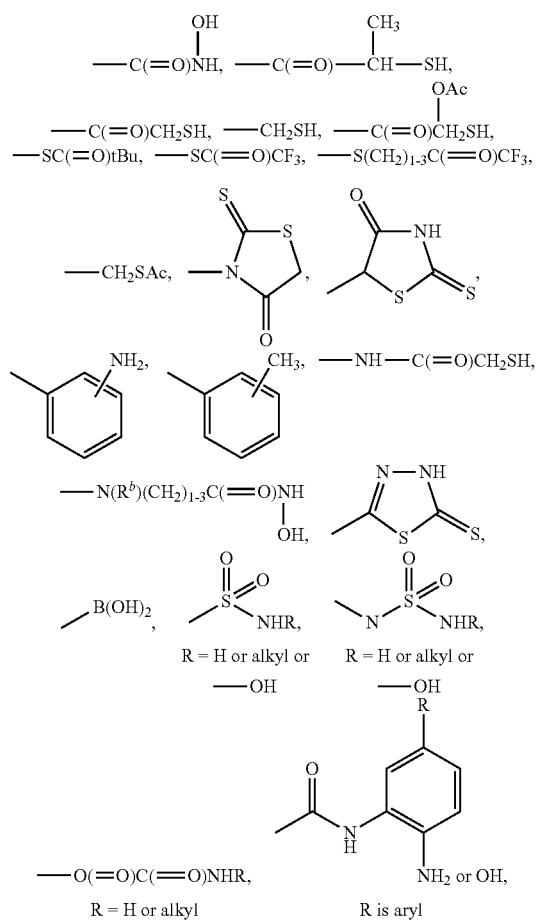

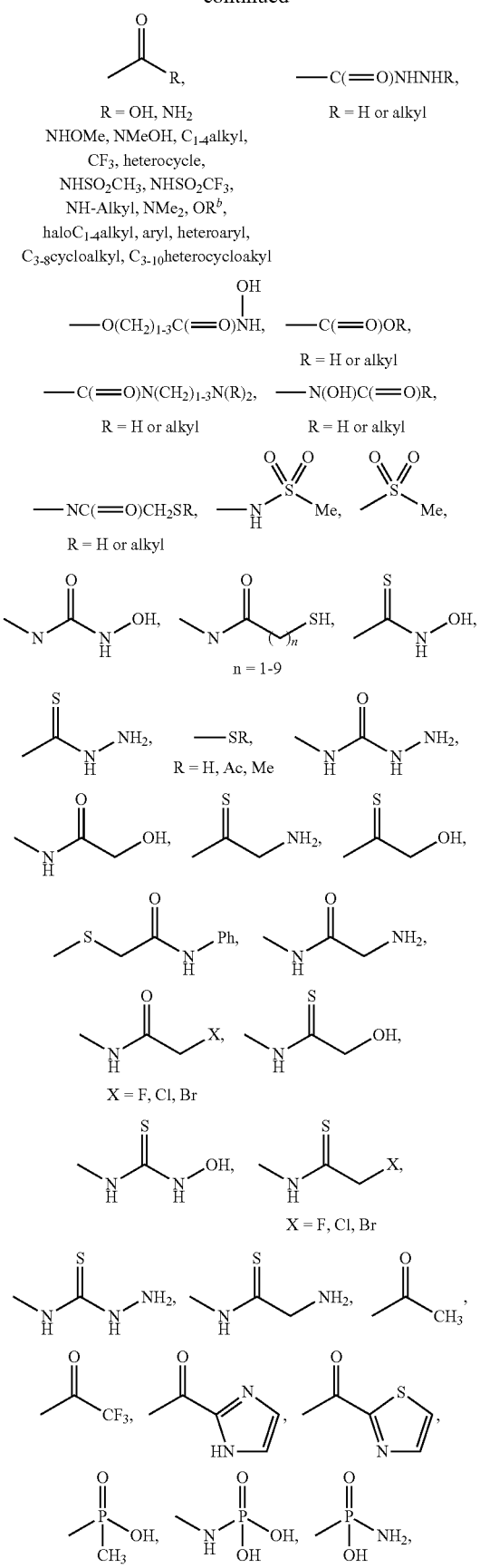

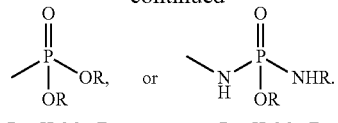

Additionally, salts, prodrugs, and hydrates of the present HDACIs also are included in the present invention and can be used in the methods disclosed herein. The present invention further includes all possible stereoisomers and geometric isomers of the compounds of structural formula (I). The present invention includes both racemic compounds and optically active isomers. When an HDACI of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry,* 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Prodrugs of compounds of structural formula (I) also are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.,* 15, 83 (1995)). Specific prodrugs of HDACIs are discussed in WO 2008/055068, incorporated in its entirety herein by reference.

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the invention can exist as salts. Pharmaceutically acceptable salts of the present HDACIs often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or prodrugs thereof.

The compounds of structural formula (I) also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.* (2001) 7:3229).

Specific compounds of the present invention include, but are not limited to,

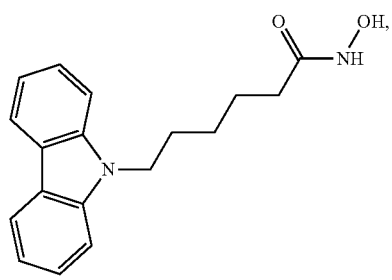

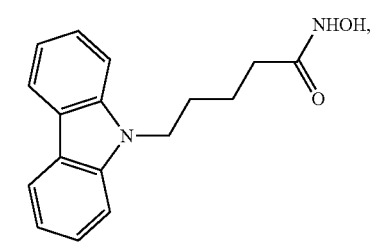

-continued

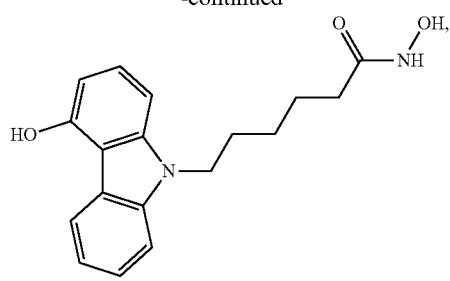

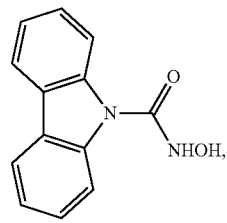

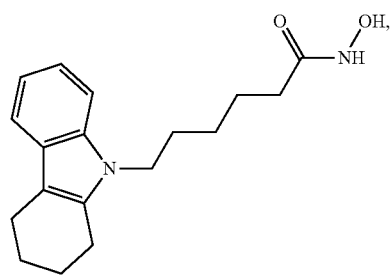

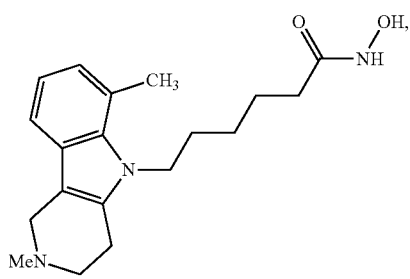

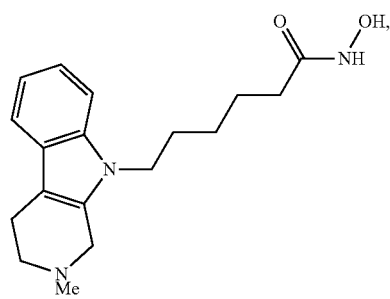

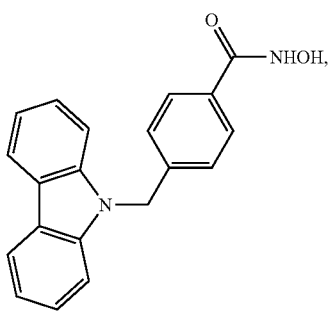

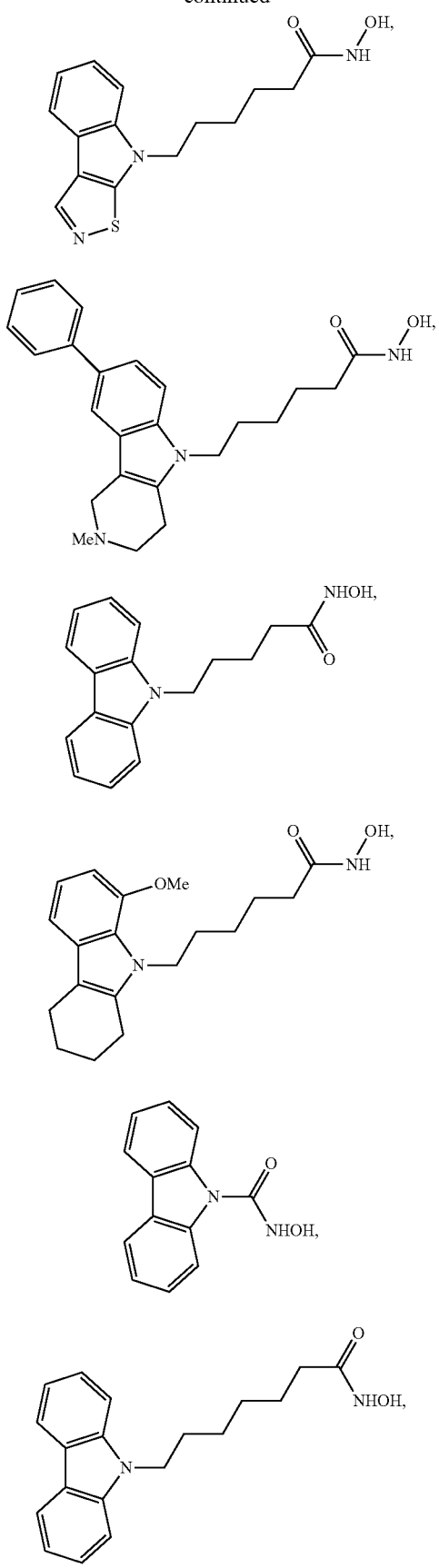
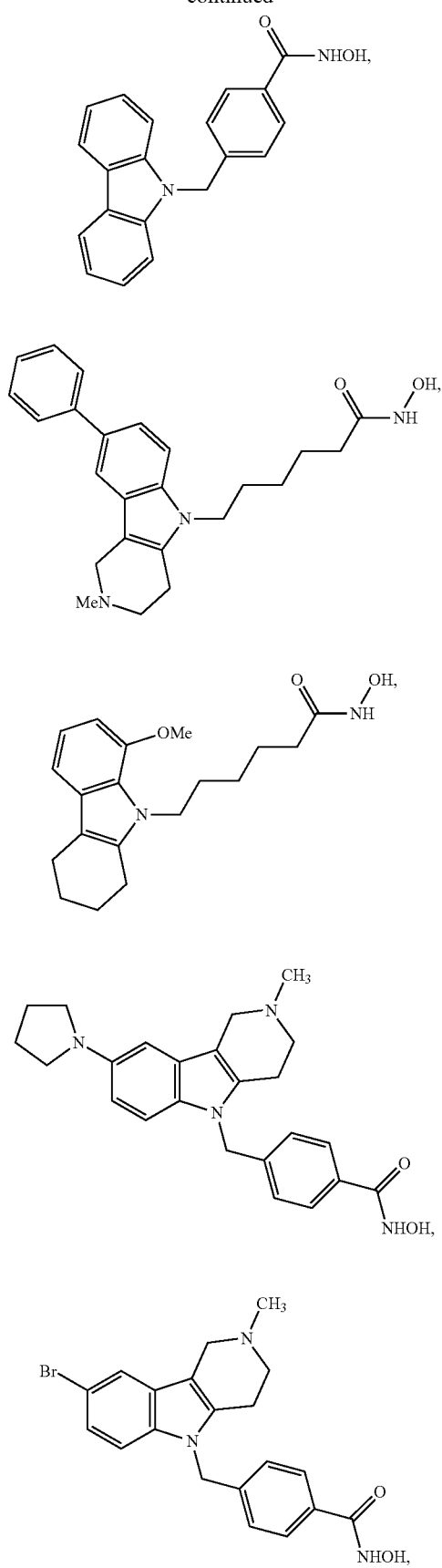

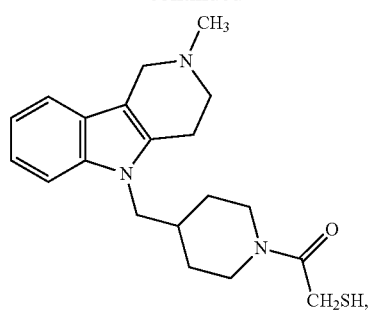
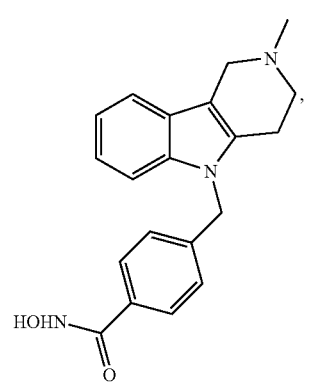
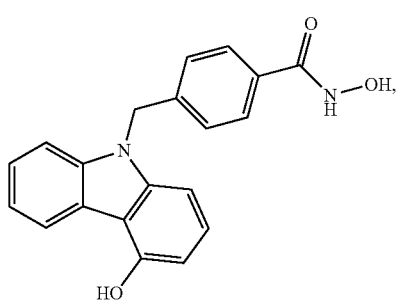
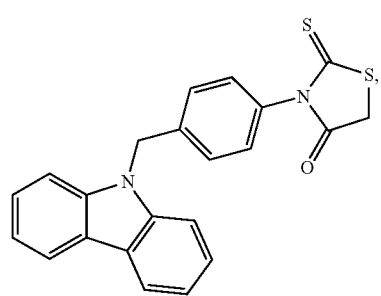
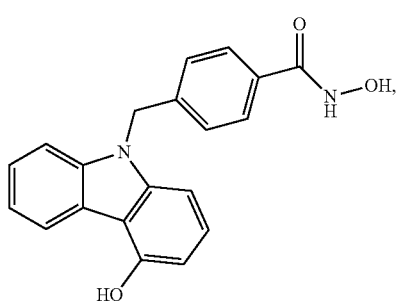
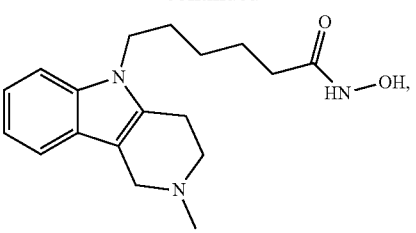
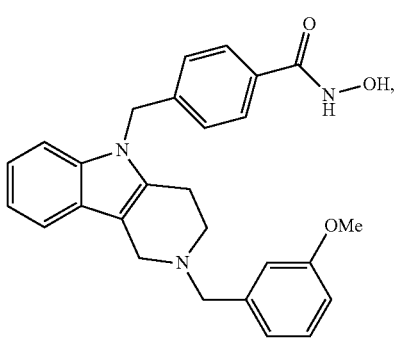
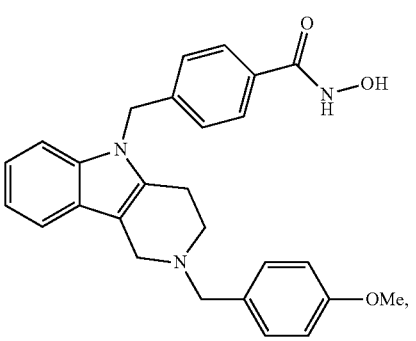
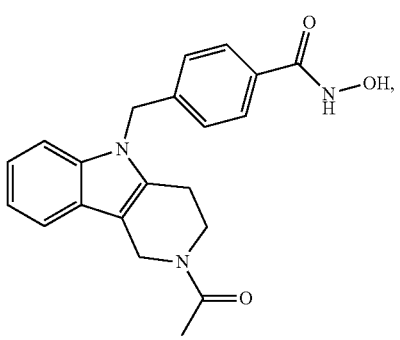

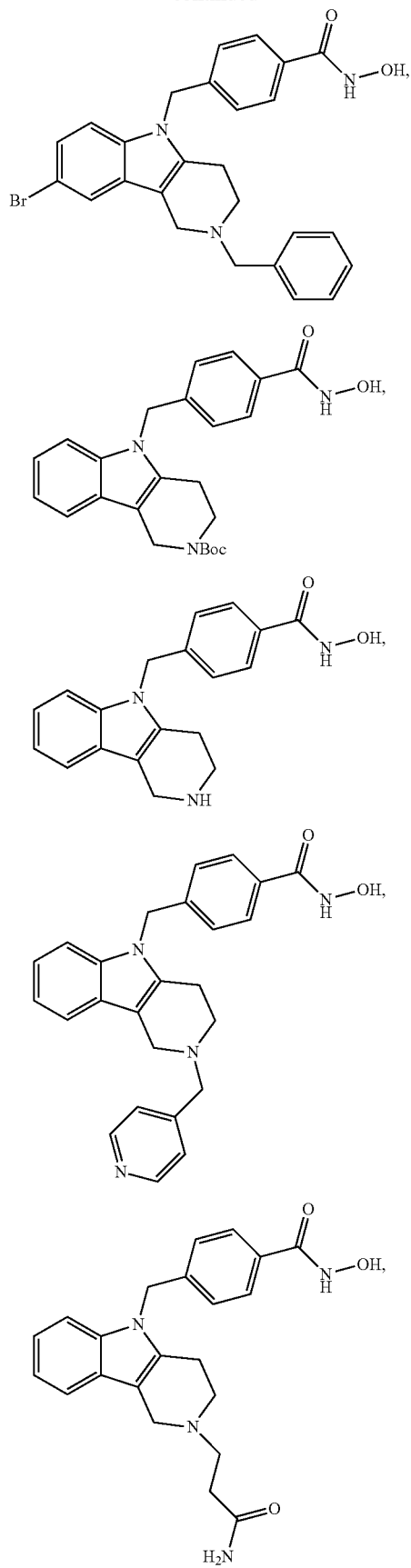
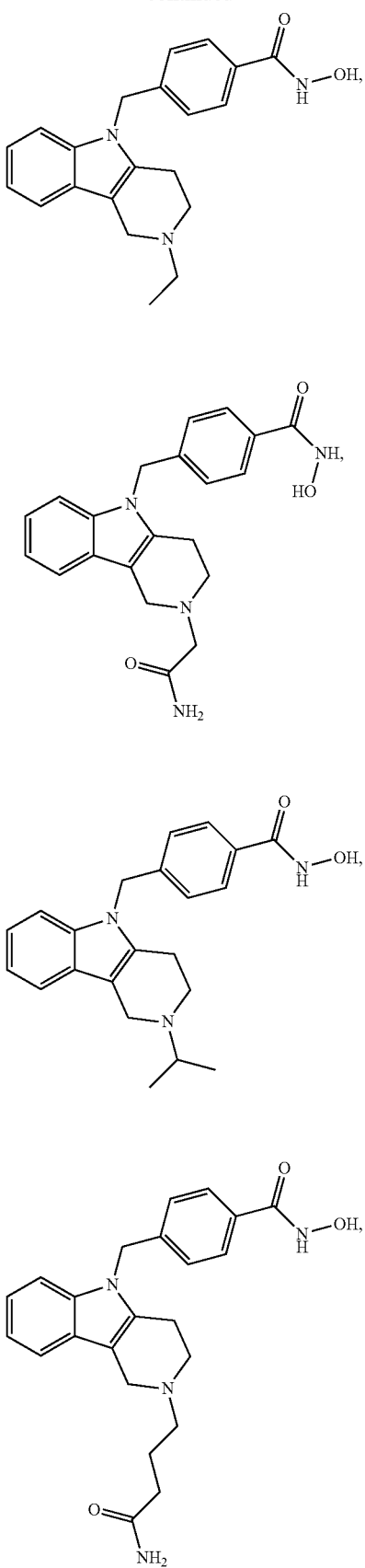

35
-continued
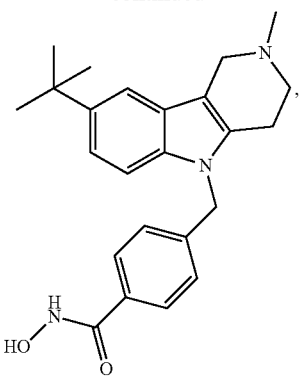
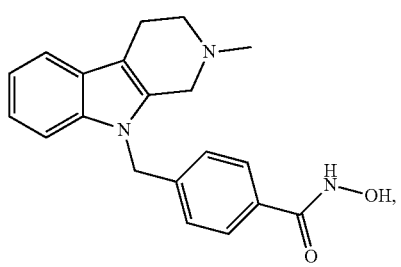
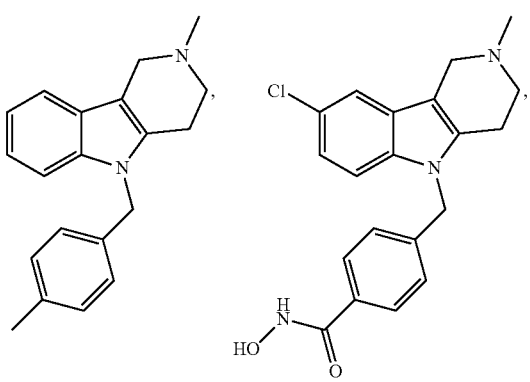
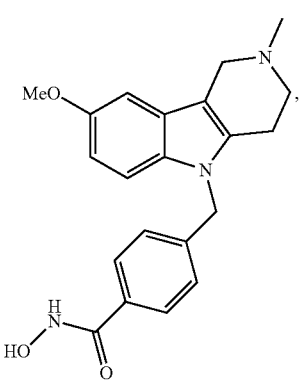
36
-continued
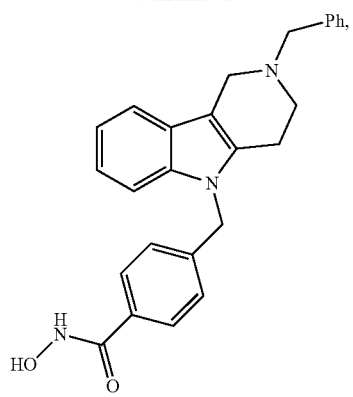
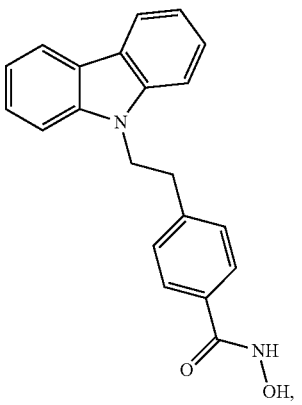
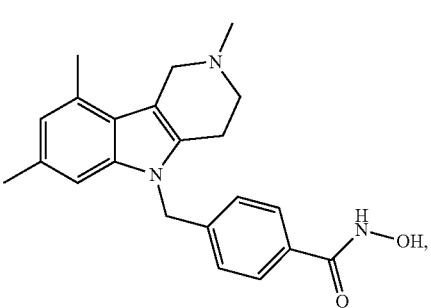
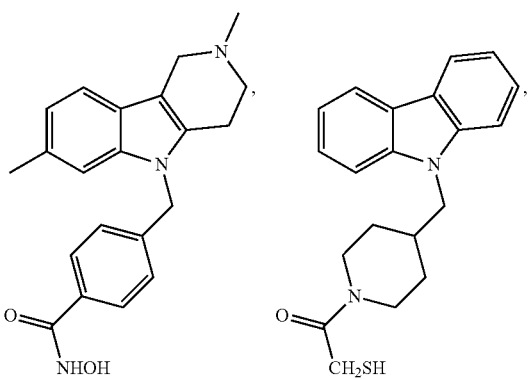

37
-continued
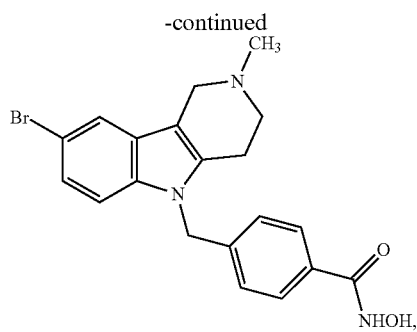
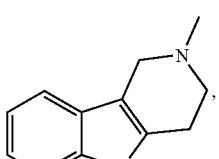
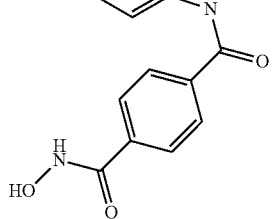
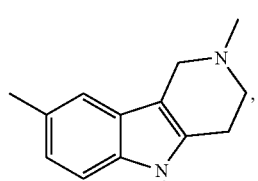
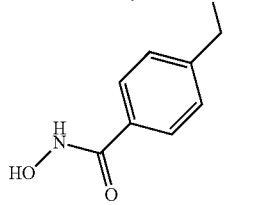
38
-continued
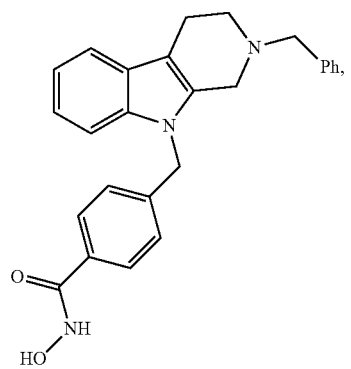
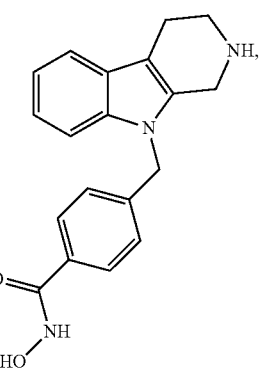
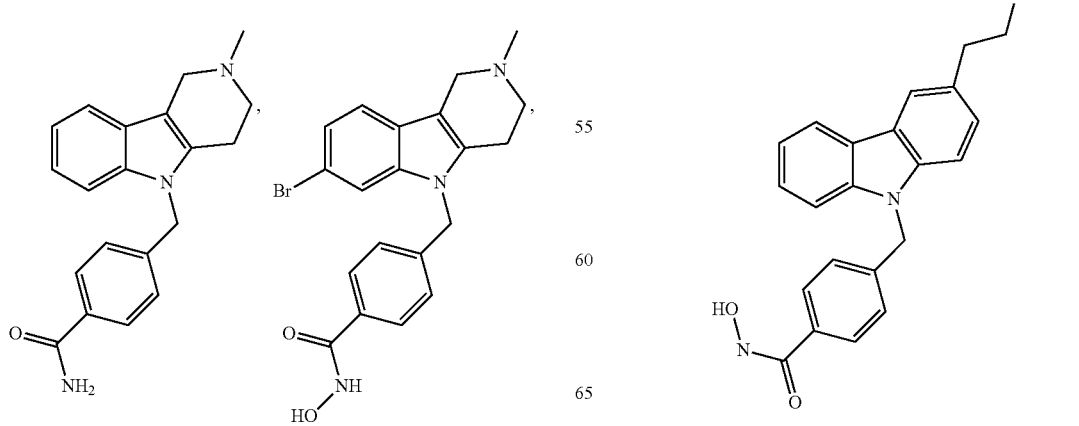

39
-continued
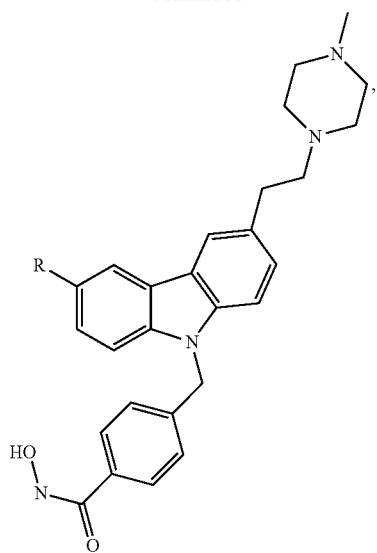
R = H, Me, Cl, Br
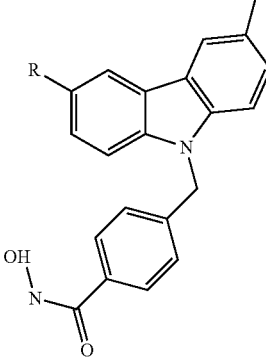
40
-continued
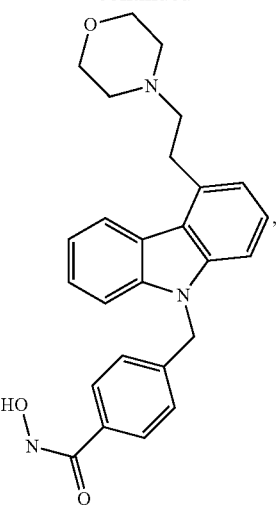
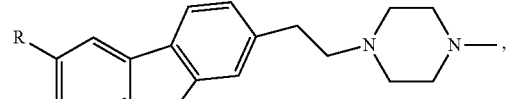
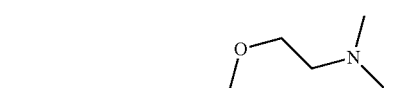
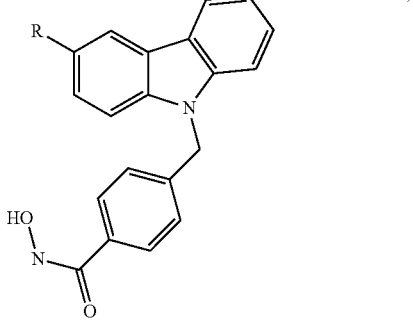

41
-continued
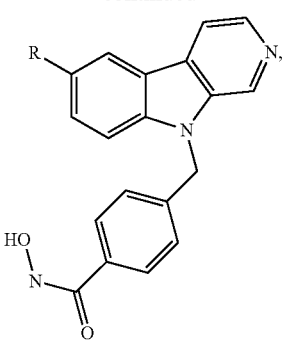
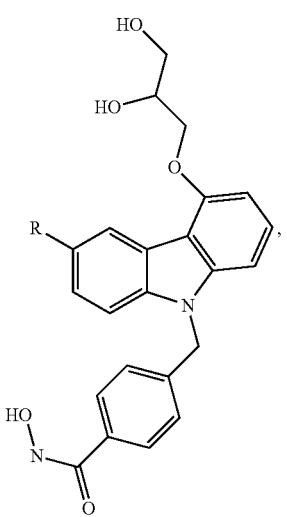
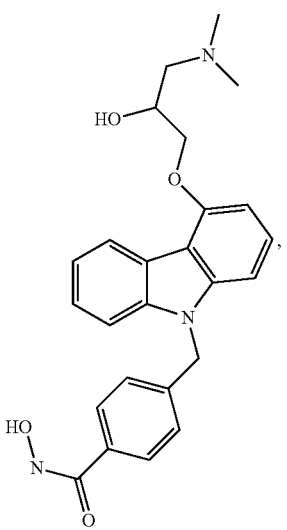
42
-continued
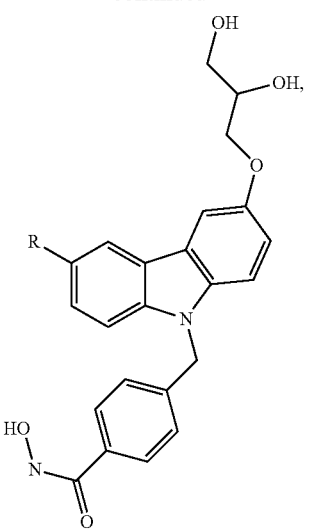
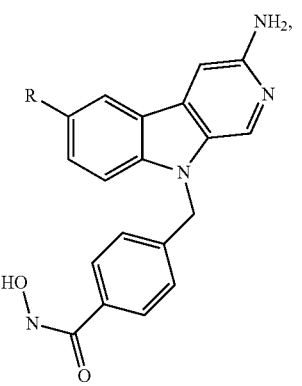
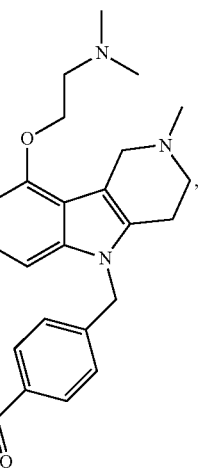

43
-continued
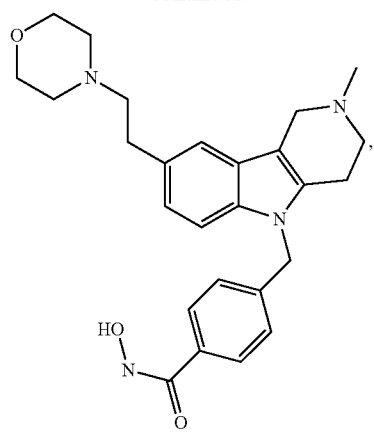
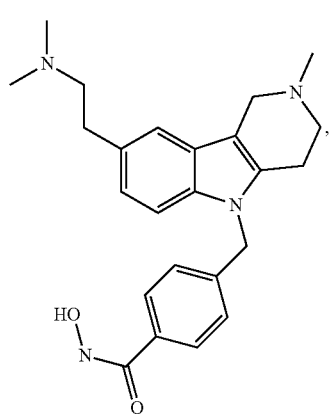
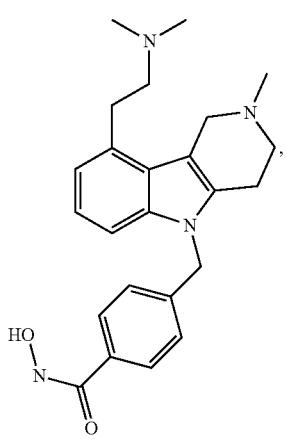
44
-continued
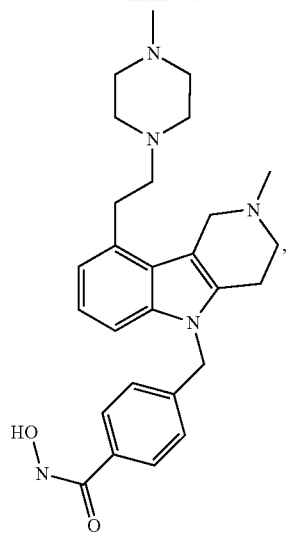
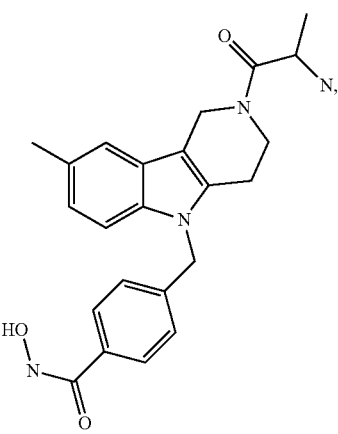
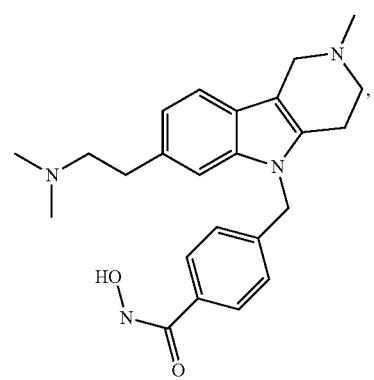

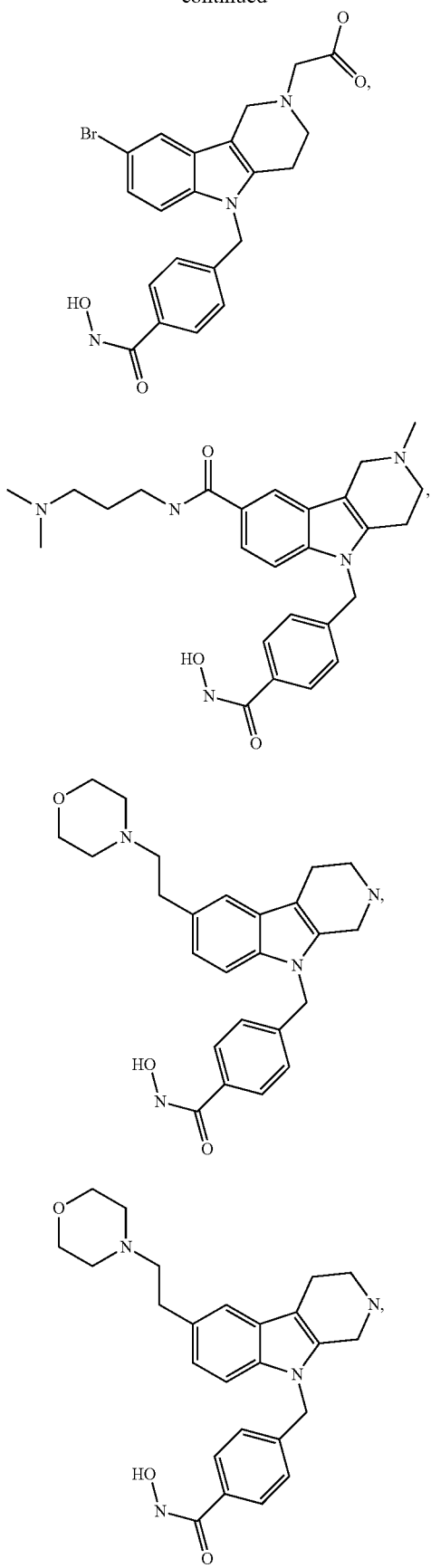
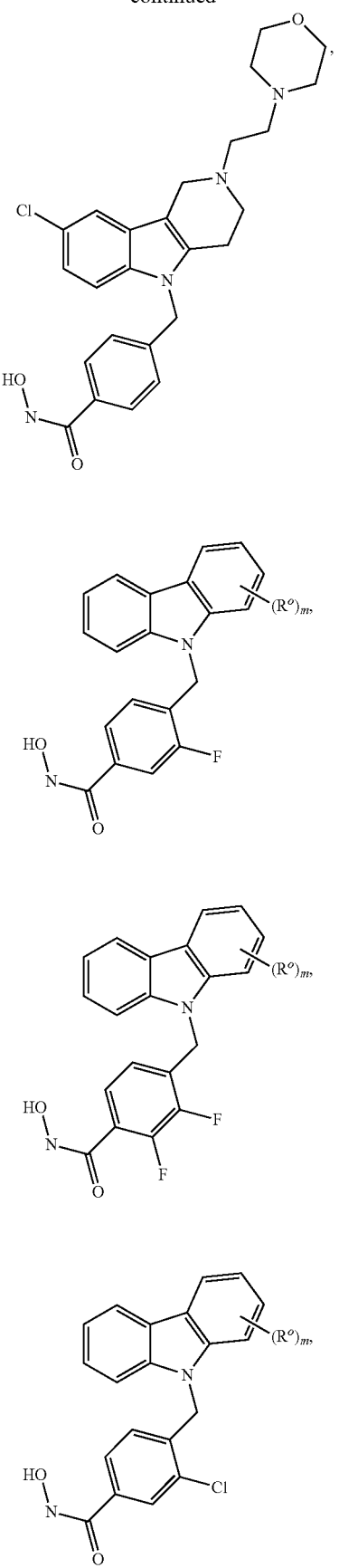

-continued
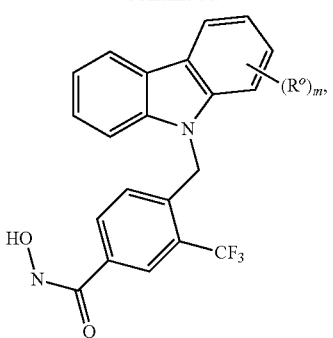
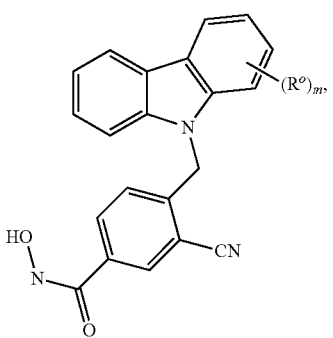
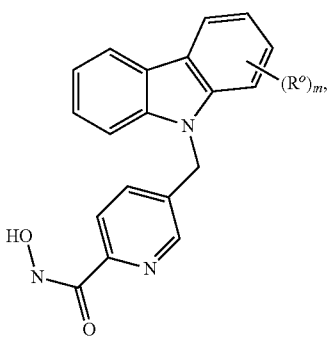
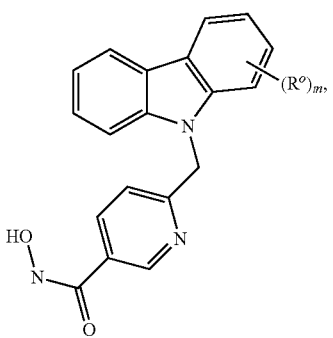
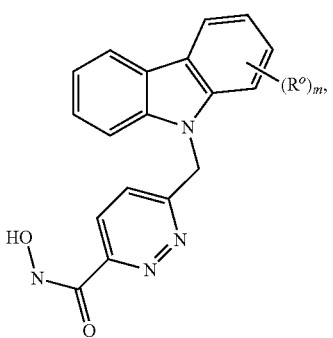
-continued
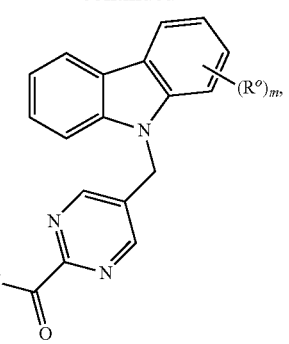
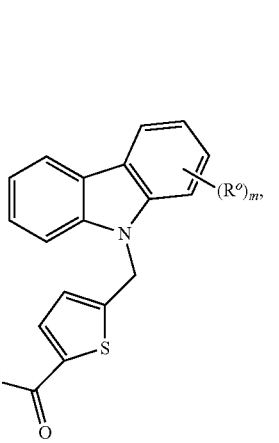
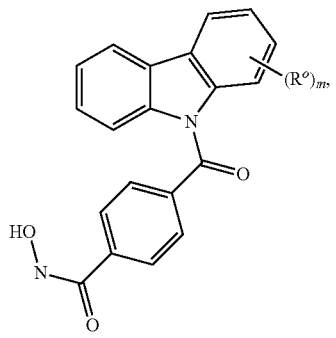
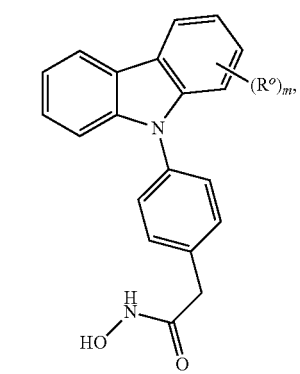

49
-continued
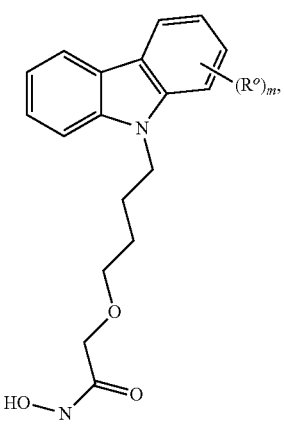
50
-continued
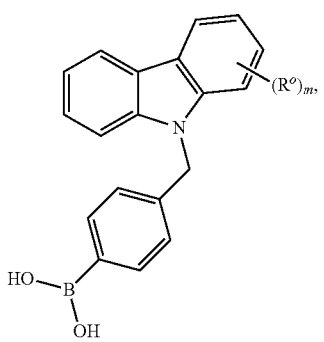
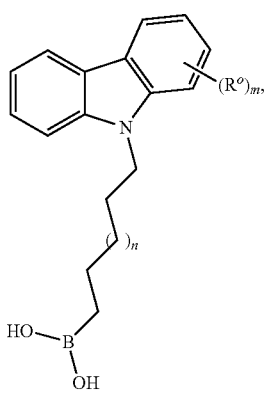
n = 1, 2
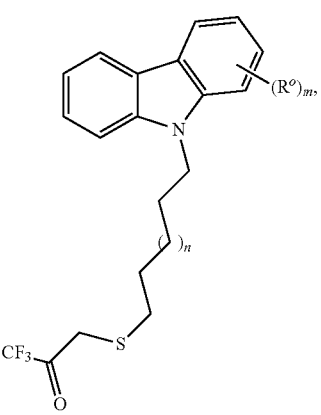
n = 1, 2
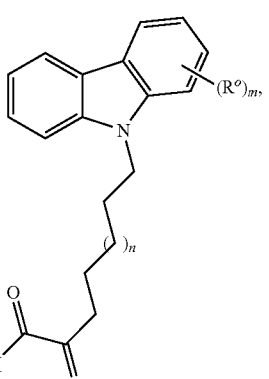
n = 1, 2

-continued
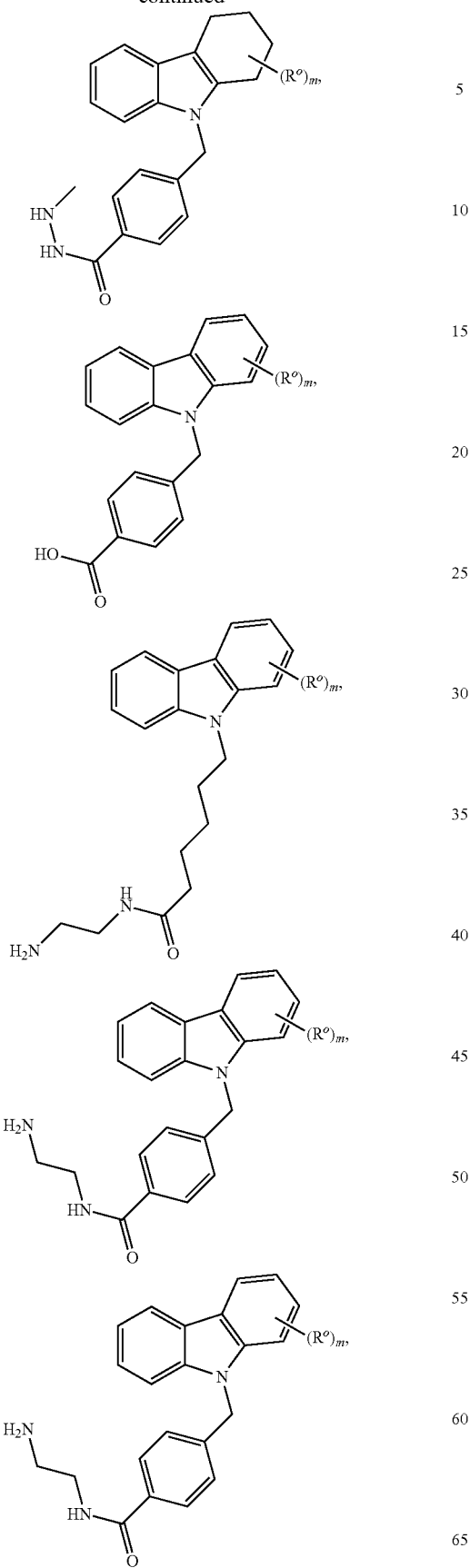
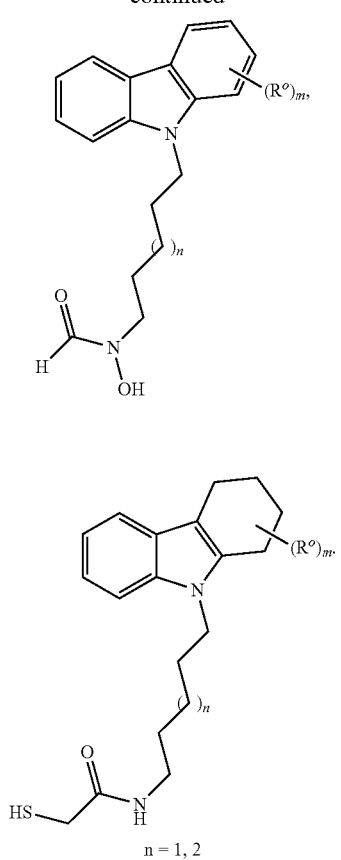
n = 1, 2
Three preferred structures of the invention are
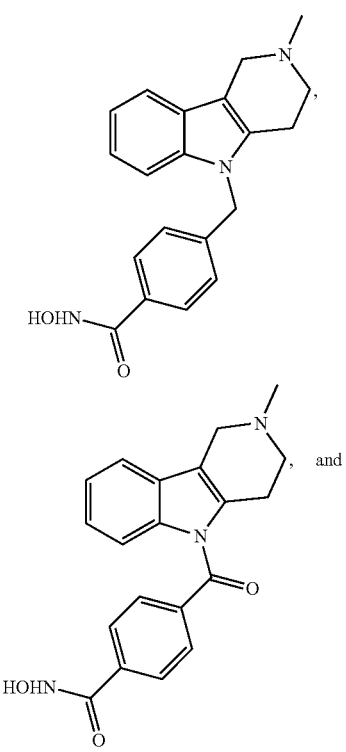
and

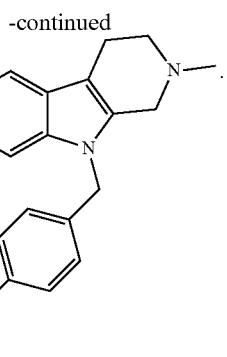

The following synthetic schemes are representative of the reactions used to synthesize compounds of structural formula (I). Modifications and alternate schemes to prepare HDACIs of the invention are readily within the capabilities of persons skilled in the art.

Synthetic Methods

Compounds of formula (I) can be prepared by any suitable method known in the art, or by the following processes which form part of the present invention. In particular, compounds of structural formula (I) can be prepared according to the following synthetic schemes.

In the synthetic methods, the examples, and throughout the specification, the abbreviations have the following meanings:

| | |
|---|---|
| DMF | dimethylformamide |
| min | minutes |
| TLC | thin layer chromatography |
| $CH_2Cl_2$ | methylene chloride |
| MeOH | methanol |
| $Na_2SO_4$ | sodium sulfate |
| AcOH | acetic acid |
| MS | mass spectrometry |
| $Na_2CO_3$ | sodium carbonate |
| HPLC | high performance liquid chromatography |
| h | hours |
| $NaHCO_3$ | sodium bicarbonate |
| HCl | hydrochloric acid |
| g | gram |
| mol | mole |
| mmol | millimole |
| mL | milliliter |
| $H_2SO_4$ | sulfuric acid |
| NaH | sodium hydride |
| TMS | tetramethylsilane |
| TFA | trifluoroacetic acid |
| KOH | potassium hydroxide |
| $NH_4Cl$ | ammonium chloride |
| $NH_2OHCl$ | hydroxylamine hydrochloride |
| NaOMe | sodium methoxide |
| $CD_3OD$ | deuterated methanol |
| M | molar |
| KOtBu | potassium tert-butoxide |
| DMSO | dimethyl sulfoxide |
| KOH | potassium hydroxide |
| $NaCNBH_3$ | sodium cyanoborohydroxide |
| N | normal |
| KI | potassium iodide |
| $SOCl_2$ | thionyl chloride |
| $CD_3CN$ | deuterated acetonitrile |
| $ZnCl_2$ | zinc chloride |
| CuI | copper iodide |
| NMR | nuclear magnetic resonance spectrometry |
| EtOAc | ethyl acetate |
| THF | tetrahydrofuran |
| NaOH | sodium hydroxide |
| $PdCl_2(PPh)_3$ | dichloro-triphenylphosphino-palladium (II) |
| $NEt_3$ | triethylamine |
| $CDCl_3$ | deuterated chloroform |
| Hz | Hertz |

It should be understood that protecting groups can be utilized in accordance with general principles of synthetic organic chemistry to provide compounds of structural formula (I). Protecting group-forming reagents are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

Synthetic Methods and Procedures

General Information for Synthetic Methods.

$^1$H NMR and $^{13}$C NMR spectra were recorded on a Bruker spectrometer with TMS as an internal standard. Standard abbreviation indicating multiplicity was used as follows: s=singlet, d=doublet, t=triplet, q=quadruplet, m=multiplet and br=broad. $^{13}$C APT experiments: up —C, $CH_2$; down —CH, $CH_3$. MS experiments were performed on a Hewlett Packard Series 1100MSD machine using electrospray ionization. HRMS experiment was performed on Q-TOF-2TM (Micromass). The progress of all reactions was monitored by TLC on precoated silica gel plates (Merck Silica Gel 60 F254). Column chromatography was performed using Merck silica gel (40-60 mesh). Column chromatography was performed using silica gel unless otherwise indicated. Medium pressure automated column chromatography (MPCC) was performed on a Combiflash Rf machine. Solvents and reagents were obtained from commercial sources. Solvents were anhydrous unless otherwise noted. Tubacin was provided by Harvard University.

HPLC Methods.

Solvents: 0.05% TFA in water (solvent A); 0.05% TFA in 1:1 mixture of water and MeOH (solvent B); and 0.05% TFA in MeOH (solvent C). Method A: Column: Synergi 4 um (150×4.6 mm), flow rate 1.4 mL/min. Machine: Agilent 1100. Gradient: t=0 min, 100% A; t=5 min, 100% B; t=12 min, 100% C; t=16 min, 100% C; t=20 min, 40% A, 60% B; t=25 min, 40% A, 60% B. Method B: Column: Synergi 4 μm (150×4.6 mm), flow rate 1.4 mL/min. Machine: Agilent 1100. Gradient: t=0 min, 100% A; t=8 min, 100% B; t=18 min, 100% C; t=21 min, 100% C; t=24 min, 80% A, 20% B; t=29 min, 80% A, 20% B.

Procedures

General Procedure A: To KOH (4.8 g) stirring in methanol (20 mL) at 0° C. was added hydroxylamine hydrochloride (5.2 g) and allowed to stir at that temperature for 30 minutes. The mixture was filtered and the filtrate transferred to a round bottom flask. A solution of the ester starting material in a minimal amount of methanol was added to the flask and allowed to stir for 1 h. The reaction mixture was neutralized by addition of saturated aqueous $NH_4Cl$ and the volume reduced by rotary evaporation to remove methanol. The reaction mixture was transferred to a separatory funnel with ethyl acetate (50 mL) and water (30 mL). The organic layer was separated, dried ($Na_2SO_4$) and concentrated.

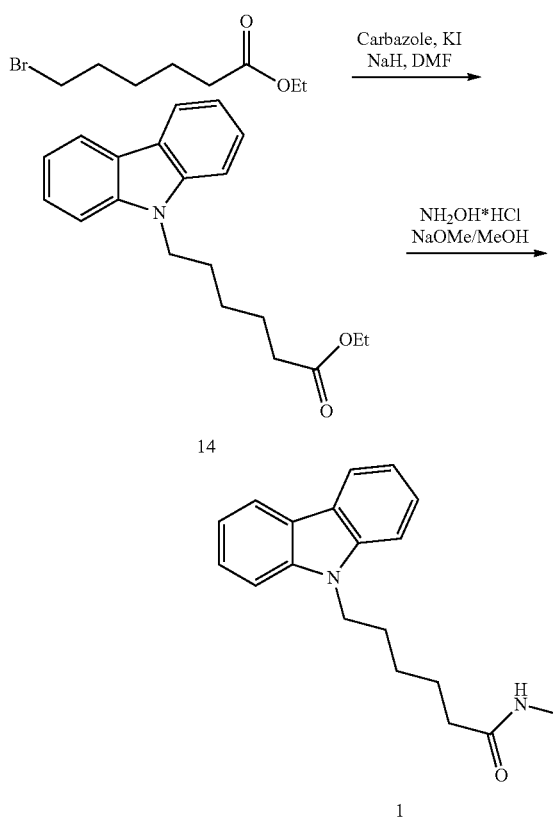

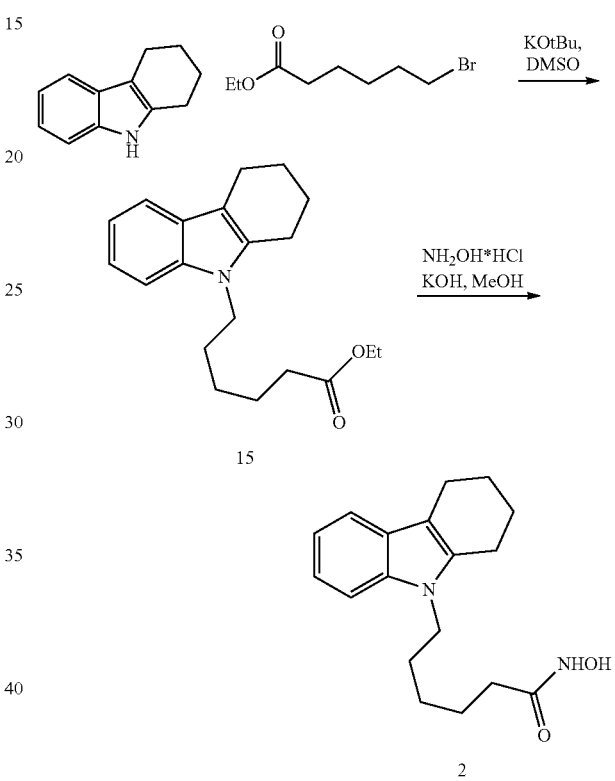

6-Carbazol-9-yl-hexanoic acid ethyl ester (14): Carbazole (2.0 g, 12.0 mmol) and sodium hydride (60 wt. % in mineral oil, 0.29 g, 12.0 mmol) were placed under argon and dissolved in DMF (5 mL). After stirring for 30 minutes, 6-bromo-hexanoic acid ethyl ester (2.0 mL, 12.0 mmol) and potassium iodide (10 mg) were added to the reaction. The reaction was heated to 80° C. for 2 h. The reaction was then quenched with water (30 mL) followed by addition of ethyl acetate (30 mL). The organic layer was isolated and the aqueous layer extracted with ethyl acetate (2×10 mL). The combined organic layers were washed with water (2×20 mL), brine (15 mL), dried ($Na_2SO_4$) and concentrated in vacuo. Purification by column chromatography (0-80% gradient of ethyl acetate in hexane) afforded the title compound (2.7 g, 73%) as a yellow oil. $^1$H NMR (400 MHz, $CDCl_3$): δ 8.13 (d, 2H, J=7.7 Hz), 7.56 (d, 2H, J=8.2 Hz), 7.42 (m, 2H), 7.26 (m, 2H), 4.34 (t, 2H, J=7.0 Hz), 4.13 (q, 2H, J=7.1 H), 2.29 (t, 2H, J=7.3 Hz), 1.93 (m, 2H), 1.70 (m, 2H), 1.45 (m, 2H), 1.25 (t, 3H, J=7.1 Hz). $^{13}$C NMR (100 MHz, DMSO): δ 173.1, 140.4, 126.1, 122.5, 120.7, 119.0, 109.6, 60.0, 42.5, 33.8, 28.7, 26.4, 24.7, 14.5. ESI-HRMS (m/z): $[M+H]^+$ calcd. for $C_{20}H_{23}NO_2$, 310.1802. found, 310.1792.

6-Carbazol-9-ylhexanoic acid hydroxyamide (1): 6-Carbazol-9-ylhexanoic acid ethyl ester (14) (1.0 g, 3.2 mmol) and hydroxylamine hydrochloride (1.4 g, 19.4 mmol) were placed under argon and dissolved in 5 mL of methanol. To it was added a 25 wt. % sodium methoxide solution in methanol (5.6 g, 25.9 mmol) which resulted in the formation of a white precipitate. The reaction was stirred for 24 h at room temperature after which the reaction was diluted with ethyl acetate (20 mL) and saturated aqueous $NaHCO_3$ (20 mL). The organic layer was isolated and the aqueous layer was further extracted with ethyl acetate (2×10 mL). The combined organic layers were washed with brine (10 mL), dried with anhydrous sodium sulfate, filtered, and concentrated in vacuo. The crude extract was purified by HPLC to yield the title compound (0.41 g, 41%) as a white solid. $^1$H NMR (400 MHz, DMSO): δ 10.29 (s, 1H), 8.64 (s, 1H), 8.15 (d, 2H, J=7.7 Hz), 7.59 (d, 2H, J=8.2 Hz), 7.46 (m, 2H), 7.19 (m, 2H), 4.37 (t, 2H, J=7.1 Hz), 1.90 (t, 2H, J=7.3 Hz), 1.76 (m, 2H), 1.51 (m, 2H), 1.30 (m, 2H). $^{13}$C NMR (100 MHz, DMSO): δ 169.4, 140.4, 126.1, 122.4, 120.7, 119.1, 109.6, 42.6, 32.6, 28.7, 26.6, 25.3. ESI-HRMS (m/z): $[M+H]^+$ calcd. for $C_{18}H_{20}N_2O_2$, 297.1598. found, 297.1591. Analytical HPLC: Purity=99%, $t_R$=10.54 min, Method A.

6-(1,2,3,4-Tetrahydrocarbazol-9-yl)hexanoic acid ethyl ester (15): A RB flask fitted with reflux condenser containing tetrahydrocarbazole (1.71 g, 10.0 mol) was dissolved in DMSO (30 mL), treated with potassium tert-butoxide (1M solution in THF, 12 mL) and stirred at 110° C. for 20 min. Ethyl 6-bromohexanoate (1.67 mL, 10.0 mmol) was added and the mixture stirred at 110° C. for 60 min. The reaction was quenched with a 1:1 brine:water solution (120 mL) and extracted with ethyl acetate. The combined organic extracts were washed with brine, dried ($Na_2SO_4$) and concentrated. Purification by column chromatography (25% ethyl acetate in hexane) afforded the title compound (1.01 g, 32%). $^1$H NMR (400 MHz, $CDCl_3$): δ 7.52 (m, 1H), 7.27 (m, 1H), 7.19 (m, 1H), 7.12 (m, 1H), 4.18 (q, 2H, J=7.1 Hz), 4.04 (t, 2H, J=7.4 Hz), 2.78-2.73 (m, 4H), 2.33 (t, 2H, J=7.5 Hz), 2.00-1.92 (m, 4H), 1.80-1.75 (m, 2H), 1.72-1.66 (m, 2H), 1.42 (m, 2H), 1.30 (t, 3H, J=6.9 Hz). ESI-HRMS (m/z): $[M+H]^+$ calcd. for $C_{20}H_{27}NO_2$, 314.2115. found, 314.2103.

6-(1,2,3,4-Tetrahydrocarbazol-9-yl)hexanoic acid hydroxyamide (2): 6-(1,2,3,4-Tetrahydro-carbazol-9-yl)hexanoic acid ethyl ester (15) (200 mg, 0.64 mmol) was converted to hydroxamic acid by procedure A. Purification by HPLC afforded the product (43 mg, 22%). $^1$H NMR (300 MHz, CD$_3$OD): δ 7.35 (d, 1H, J=7.6 Hz), 7.24 (d, 1H, J=8.1 Hz), 7.06 (t, 1H, J=7.7 Hz), 6.95 (t, 1H, J=7.1 Hz), 4.02 (t, 2H, J=7.1 Hz), 2.70 (m, 4H), 2.05 (t, 2H, J=7.3 Hz), 1.94 (m, 2H), 1.85 (m, 2H), 1.72 (m, 2H), 1.62 (m, 2H), 1.33 (m, 2H). $^{13}$C NMR APT (100 MHz, CDCl$_3$): δ 178.1 (up), 171.7 (up), 135.2 (up), 127.3 (up), 120.5 (down), 118.5 (down), 117.8 (down), 109.2 (up), 108.7 (down), 42.6 (up), 33.8 (up), 32.4 (up), 29.9 (up), 26.4 (up), 25.2 (up), 23.3 (up), 22.2 (up), 21.0 (up). ESI-HRMS (m/z): [M+H]$^+$ calcd. for C$_{18}$H$_{24}$N$_2$O$_2$, 301.1911. found, 301.1898. Analytical HPLC: Purity=100%, $t_R$=8.04 min, Method A.

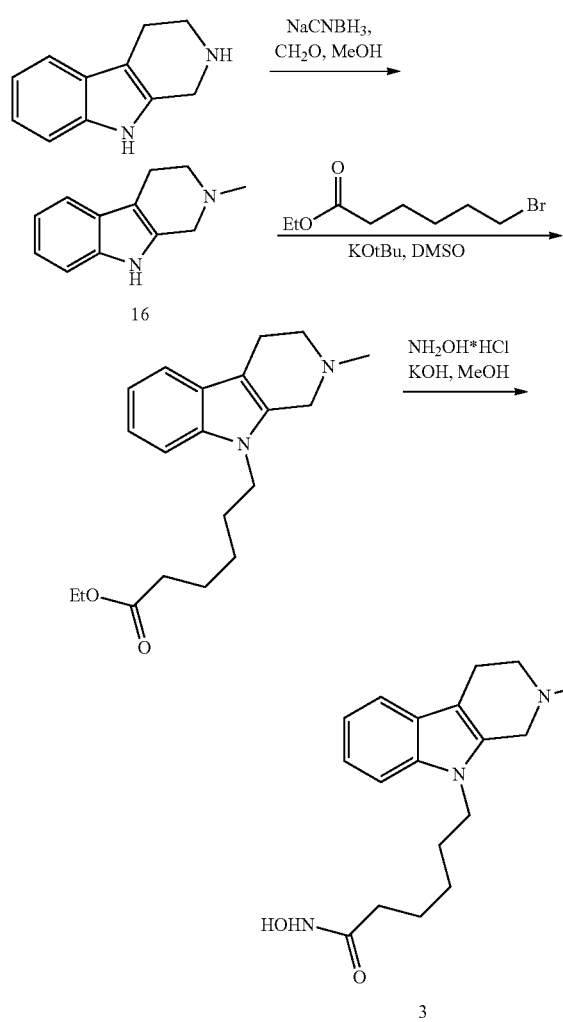

2-Methyl-2,3,4,9-tetrahydro-1H-β-carboline (16): 2,3,4,9-Tetrahydro-1H-β-carboline (0.50 g, 2.9 mmol) and NaCNBH$_3$ (0.44 g, 7.0 mmol) were added to a round bottomed flask, dissolved in MeOH (35 mL), and treated with 3.23 mL of a 27% solution of formaldehyde in water. This mixture was stirred for 2 h, after which, 2N HCl (50 mL) was added, followed by stirring for 15 min. The mixture was taken to pH=11 by addition of concentrated, aqueous NaOH and extracted with methylene chloride (3×30 mL). The combined organic layers were washed with brine, dried (Na$_2$SO$_4$), and concentrated. The product was purified by MPCC (0-10% gradient of MeOH in CH$_2$Cl$_2$), giving the title compound (511 mg, 95%) as a white solid. $^1$H NMR (400 MHz, CD$_3$OD): δ 7.39 (d, 1H, J=7.7 Hz), 7.27 (d, 1H, J=8.0 Hz), 7.05 (t, 1H, J=7.5 Hz), 6.96 (t, 1H, J=7.7 Hz), 3.68 (s, 2H), 2.86 (m, 4H), 2.53 (s, 3H). $^{13}$C NMR APT (100 MHz, CD$_3$OD): δ 136.1 (up), 131.7 (up), 127.2 (up), 121.2 (down), 119.2 (down), 117.9 (down), 110.8 (down), 107.8 (up), 53.0 (up), 52.1 (up), 45.5 (down), 21.4 (up). ESI-HRMS (m/z): [M+H]$^+$ calcd. for C$_{12}$H$_{14}$N$_2$, 187.1230. found, 187.1233

6-(2-Methyl-1,2,3,4-tetrahydro-β-carbolin-9-yl)hexanoic acid hydroxyamide, trifluoroacetic acid salt (3): A round bottom flask fitted with reflux condenser containing 2-methyl-2,3,4,9-tetrahydro-1H-β-carboline (16) (0.20 g, 1.1 mmol), and sodium hydride (60% by wt. in mineral oil, 0.055 g, 1.35 mmol) was vacuum purged and filled with argon, followed by addition of DMF (4 mL). After stirring at 60° C. for 20 min, ethyl 6-bromo-hexanoate (0.24 g, 1.1 mmol) was added and the mixture was stirred at 60° C. for 6 h. The reaction was quenched by addition of water (30 mL), transferred to a separatory funnel and extracted with ethyl acetate (3×20 mL). The combined organic layers were washed with brine (2×20 mL), dried (Na$_2$SO$_4$) and concentrated. The product was purified by MPCC (0-10% gradient of MeOH in CH$_2$Cl$_2$), giving 190 mg of 6-(2-methyl-1,2,3,4-tetrahydro-b-carbolin-9-yl) hexanoic acid ethyl ester.

6-(2-Methyl-1,2,3,4-tetrahydro-β-carbolin-9-yl)hexanoic acid ethyl ester (150 mg) and hydroxylamine hydrochloride (190 mg, 2.74 mmol) were placed under argon and dissolved in 1 mL of methanol. To it was added a 25 wt. % sodium methoxide solution in methanol (0.7 g, 3.2 mmol) which resulted in the formation of a white precipitate. The reaction was stirred for 24 h at room temperature after which the reaction was diluted with ethyl acetate (20 mL) and saturated aqueous NaHCO$_3$ (20 mL). The organic layer was isolated and the aqueous layer was further extracted with ethyl acetate (2×10 mL). The combined organic layers were washed with brine (10 mL), dried with anhydrous sodium sulfate, filtered, and concentrated in vacuo. The crude extract was purified by HPLC to yield the title compound (49 mg) as a white solid. $^1$H NMR (400 MHz, CD$_3$OD): δ 7.51 (d, 1H, J=8.0 Hz), 7.42 (d, 1H, J=8.4 Hz), 7.23 (t, 1H, J=7.4 Hz), 7.10 (t, 1H, J=7.1 Hz), 4.64 (br, 2H), 4.12 (m, 2H), 3.70 (br, 2H), 3.18 (m, 5H), 2.07 (t, 2H, J=7.3 Hz), 1.80 (m, 2H), 1.63 (m, 2H), 1.35 (m, 2H). $^{13}$C NMR (100 MHz, CDCl$_3$): δ 136.7, 125.8, 125.7, 122.5, 119.9, 118.5, 109.6, 104.8, 52.2, 50.2, 43.6, 42.3, 29.1, 25.7, 24.6, 18.2 ESI-HRMS (m/z): [M+H]$^+$ calcd. for C$_{18}$H$_{25}$N$_3$O$_2$, 316.2020. found, 316.2015. Analytical HPLC: Purity=99%, $t_R$=1.58 min, Method A.

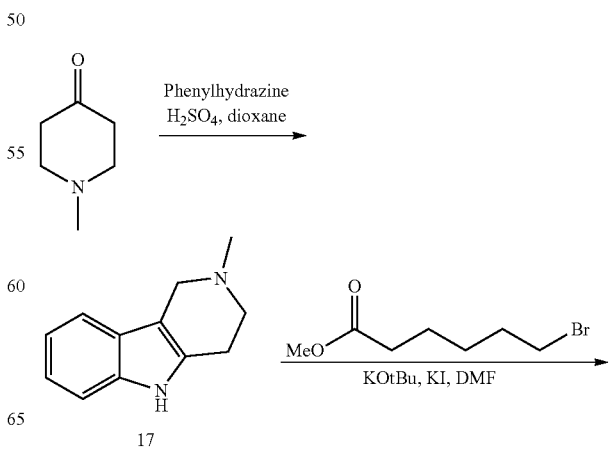

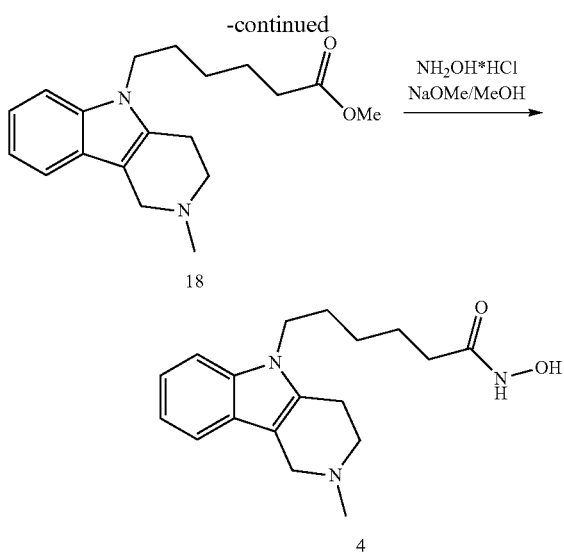

2-Methyl-2,3,4,5-tetrahydro-1H-pyrido[4,3-b]indole (17): Phenyl hydrazine (1.0 g, 9.3 mmols) and 1-methyl-piperidin-4-one (1.1 g, 9.3 mmols) were dissolved in 1,4-dioxane (35 mL) and cooled to 0° C. Concentrated sulfuric acid (5 mL) was added dropwise to the reaction at 0° C. with stirring upon which a precipitate formed. The reaction was then heated to 60° C. for one hour after which the precipitate was fully dissolved. The reaction was stirred for an additional hour at 60° C. The reaction was then cooled to room temperature and the pH was adjusted to approximately 12 by the addition of saturated aqueous sodium bicarbonate solution followed by small portions of solid sodium hydroxide. The organic products were extracted with chloroform (3×20 mL) and the combined organic extracts were washed with brine (15 mL), dried (Na$_2$SO$_4$) and concentrated in vacuo. Purification by column chromatography (0-80% gradient of ethyl acetate in hexane) afforded the final product (1.6 g, 93% yield) as a beige solid. $^1$H NMR (400 MHz, DMSO): δ 10.80 (s, 1H), 7.30 (m, 2H), 6.98 (m, 2H), 3.53 (s, 2H), 2.79 (t, J=5.2 Hz, 2H), 2.71 (t, 2H, J=5.4 Hz), 2.43 (s, 3H). $^{13}$C NMR APT (100 MHz, CDCl$_3$): δ 136.2 (up), 132.0 (up), 126.0 (up), 121.0 (down), 119.1 (down), 117.4 (down), 110.7 (down), 108.3 (up), 52.5 (up), 51.8 (up), 45.8 (down), 23.5 (up). ESI-HRMS (m/z): [M+H]$^+$ calcd. for C$_{12}$H$_{14}$N$_2$, 187.1230. found, 187.1228

6-(2-Methyl-1,2,3,4-tetrahydro-pyrido[4,3-b]indol-5-yl) hexanoic acid methyl ester (18): 2-Methyl-2,3,4,5-tetrahydro-1H-pyrido[4,3-b]indole (17) (0.50 g, 2.7 mmol) was placed under argon and dissolved in 5 mL of anhydrous DMF. Potassium tert-butoxide (0.32 g, 2.8 mmol) was dissolved in 3 mL of anhydrous DMF and added slowly to the reaction at room temperature. The reaction turned from orange to dark brown. After 15 min, 6-bromohexanoic acid methyl ester (0.56 g, 2.7 mmol) and 5 mg of potassium iodide were added to the reaction at room temperature. The reaction was heated to 80° C. for 2 h upon which a precipitate formed and the reaction turned from dark brown to dark orange. The reaction was then diluted with 30 mL of ethyl acetate and 30 mL of water. The organic layer was isolated and the aqueous layer extracted with ethyl acetate (2×10 mL). The combined organic layers were washed with water (2×20 mL), brine (15 mL), dried (Na$_2$SO$_4$) and concentrated in vacuo. Purification by MPCC (0-80% gradient of ethyl acetate in hexane) afforded the title compound (0.35 g, 40%) as a yellow oil. $^1$H NMR (400 MHz, DMSO): δ 7.46 (m, 2H), 7.17 (m, 1H), 7.06 (m, 1H), 4.46 (m, 2H), 4.10 (t, 2H, J=7.0 Hz), 3.66 (m, 2H), 3.56 (s, 3H), 3.16 (m, 2H), 3.00 (s, 3H), 2.28 (t, 2H, J=7.4 Hz), 1.66 (m, 2H), 1.55 (m, 2H), 1.29 (m, 2H). $^{13}$C NMR (100 MHz, DMSO): δ 173.7, 136.7, 131.3, 124.7, 121.9, 119.7, 118.0, 110.3, 101.8, 51.6, 51.0, 50.5, 42.9, 42.2, 33.6, 29.8, 26.1, 24.6, 19.8. ESI-HRMS (m/z): [M+H]$^+$ calcd. for C$_{19}$H$_{26}$N$_2$O$_2$, 315.1959. found, 315.1945.

6-(2-Methyl-1,2,3,4-tetrahydro-pyrido[4,3-b]indol-5-yl) hexanoic acid hydroxyamide, trifluoroacetic acid salt (4): 6-(2-Methyl-1,2,3,4-tetrahydro-pyrido[4,3-b]indol-5-yl) hexanoic acid ethyl ester (18) (0.35 g, 1.1 mmol) and hydroxylamine hydrochloride (0.44 g, 6.4 mmol) were placed under argon and dissolved in 5 mL of methanol. To it was added a 25% sodium methoxide solution in methanol (1.84 g, 8.5 mmol) which resulted in the formation of a white precipitate. The reaction was stirred for 24 h at room temperature after which the reaction was diluted with 20 mL ethyl acetate and 20 mL of saturated sodium bicarbonate. The organic layer was isolated and the aqueous layer was further extracted with ethyl acetate (2×10 mL). The combined organic layers were washed with brine (10 mL), dried (Na$_2$SO$_4$) and concentrated in vacuo. The crude extract was purified by HPLC to yield the title compound (TFA salt, 0.11 g, 23%) as a white solid. $^1$H NMR (400 MHz, DMSO): δ 10.36 (s, 1H), 10.22 (s, 1H), 7.46 (m, 2H), 7.17 (t, 1H, J=7.2 Hz), 7.06 (t, 1H, J=7.4 Hz), 4.46 (m, 2H), 4.10 (t, 2H, J=5.9 Hz), 3.54 (m, 2H), 3.16 (s, 2H), 3.00 (s, 3H), 1.92 (t, 2H, J=7.3 Hz), 1.64 (m, 2H), 1.50 (m, 2H), 1.26 (m, 2H). $^{13}$C NMR (100 MHz, DMSO): δ 169.0, 136.3, 130.9, 124.3, 121.6, 119.4, 117.7, 109.9, 101.4, 50.6, 50.2, 42.6, 41.8, 32.2, 29.5, 25.9, 24.9, 19.5. ESI-HRMS (m/z): [M+H]$^+$ calcd. for C$_{18}$H$_{25}$N$_3$O$_2$, 316.2020. found, 316.2007. Analytical HPLC: Purity=99%, $t_R$=5.32 min, Method A.

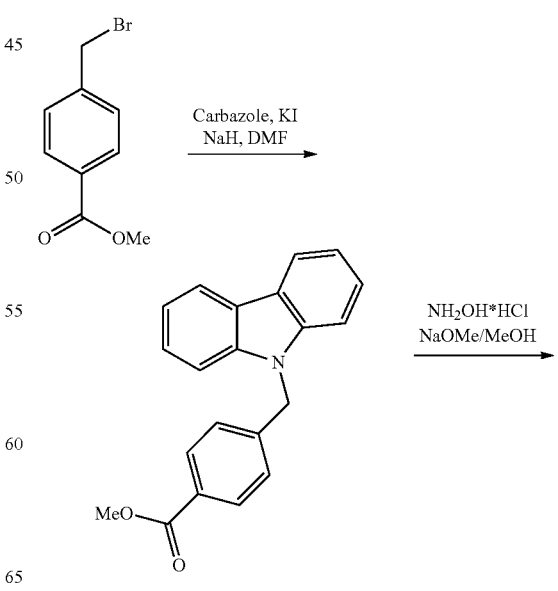

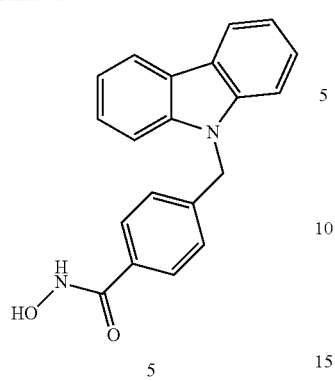

5

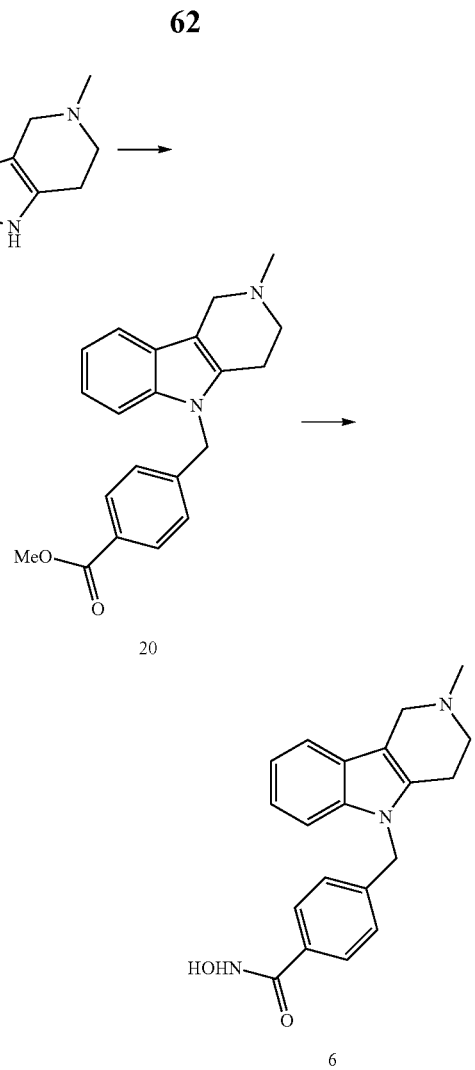

4-Carbazol-9-ylmethylbenzoic acid methyl ester (19): Carbazole (1.0 g, 6.0 mmol) and sodium hydride (60 wt. % in mineral oil, 0.14 g, 6.0 mmol) were placed under argon and dissolved in 5 mL of DMF. The mixture was stirred at room temperature for 30 min, followed by addition of 4-bromomethylbenzoic acid methyl ester (1.4 g, 6.0 mmol) and 5 mg of potassium iodide. The reaction was heated to 80° C. for 2 h upon which a precipitate formed and the reaction turned from dark brown to dark orange. The reaction was then quenched with water (30 mL) and ethyl acetate (30 mL). The organic layer was isolated and the aqueous layer extracted with ethyl acetate (2×10 mL). The combined organic layers were washed with water (2×20 mL), brine (15 mL), dried ($Na_2SO_4$) and concentrated in vacuo. Purification by column chromatography (0-80% gradient of ethyl acetate in hexane) afforded the title compound (0.95 g, 50%) as a light yellow solid. $^1$H NMR (400 MHz, DMSO): δ 8.19 (d, 2H, J=7.7 Hz), 7.51 (d, 2H, J=8.3 Hz), 7.41 (m, 4H), 7.23 (m, 4H), 5.74 (s, 2H), 3.79 (s, 3H). $^{13}$C NMR (100 MHz, DMSO): δ 166.4, 143.8, 129.9, 127.3, 126.4, 125.9, 120.8, 119.6, 118.9, 111.4, 109.9, 52.5, 45.8. ESI-HRMS (m/z): [M+H]$^+$ calcd. for $C_{21}H_{17}NO_2$, 316.1323. found, 316.1314.

4-Carbazol-9-ylmethyl-N-hydroxybenzamide (5): 4-Carbazol-9-ylmethylbenzoic acid methyl ester (19) (1.0 g, 3.2 mmol) and hydroxylamine hydrochloride (1.3 g, 19.0 mmol) were placed under argon and dissolved in 5 mL of methanol. To it was added a 25% sodium methoxide solution in methanol (5.48 g, 25.4 mmol) which resulted in the formation of a white precipitate. The reaction was stirred for 24 h at room temperature after which the reaction was diluted with 20 mL ethyl acetate and 20 mL of saturated sodium bicarbonate. The organic layer was isolated and the aqueous layer was further extracted with ethyl acetate (2×10 mL). The combined organic layers were washed with brine (10 mL), dried ($Na_2SO_4$) and concentrated in vacuo. The crude extract was purified by HPLC to yield the title compound (0.41 g, 41%) as an off-white solid. $^1$H NMR (400 MHz, DMSO): δ 11.09 (s, 1H), 8.97 (s, 1H), 8.18 (d, 2H, J=7.8 Hz), 7.61 (m, 4H), 7.43 (t, 2H, J=8.0 Hz), 7.19 (m, 4H), 5.71 (s, 2H). $^{13}$C NMR (100 MHz, DMSO): δ 164.0, 140.2, 141.1, 132.0, 127.3, 126.8, 126.0, 122.3, 120.5, 119.2, 109.5, 45.4. ESI-HRMS (m/z): [M+H]$^+$ calcd. for $C_{21}H_{17}NO_2$, 317.1149. found, 317.1143. Analytical HPLC: Purity=99%, $t_R$=10.69 min, Method A.

4-(2-Methyl-1,2,3,4-tetrahydro-pyrido[4,3-b]indol-5-ylmethyl)benzoic acid methyl ester (20): Potassium tert-butoxide (0.95 g, 8.5 mmol) was placed under argon and suspended in 1 mL of anhydrous DMF. To it was added 2-methyl-2,3,4,5-tetrahydro-1H-pyrido[4,3-b]indole (17) (1.5 g, 8.1 mmol) dissolved in 3 mL of DMF upon which the reaction turned a deep orange in color. The reaction was stirred at room temperature for 15 min after which 4-bromomethyl-benzoic acid methyl ester (1.8 g, 8.1 mmol) was added in 1 mL of DMF along with approximately 5 mg of potassium iodide. The reaction then turned a light orange in color. The reaction was stirred at 80° C. for two hours after which the reaction was quenched by the addition of 15 mL of water. The pH was adjusted to approximately 12 with 2N NaOH and the organic products were extracted with ethyl acetate (3×15 mL). The combined organic layers were washed with water (15 mL), brine (15 mL), dried with anhydrous sodium sulfate, filtered, and concentrated in vacuo. Purification by column chromatography (0-80% gradient of ethyl acetate in hexane) afforded the title compound (1.7 g, 61%) as a yellow oil. $^1$H NMR (400 MHz, $CD_3OD$): δ 7.83 (d, 2H, J=8.3 Hz), 7.33 (d, 1H, J=7.8 Hz), 7.23 (m, 3H), 7.07 (m, 1H), 6.97 (m, 1H), 4.59 (s, 2H), 4.01 (s, 2H), 3.82 (s, 3H), 2.90 (t, 2H, J=5.5 Hz), 2.84 (t, 2H, J=5.3 Hz), 2.48 (s, 3H). $^{13}$C NMR (100 MHz, MeOD): δ 167.1, 147.5, 134.9, 130.4, 129.2, 128.1, 128.0, 127.4, 120.4, 119.2, 177.7, 108.3, 108.1, 65.4, 51.0, 50.0, 40.2, 29.2, 20.3. ESI-MS (m/z): [M+H]$^+$ 335.2 m/z.

N-Hydroxy-4-(2-methyl-1,2,3,4-tetrahydro-pyrido[4,3-b]indol-5-ylmethyl)benzamide, trifluoroacetic acid salt (6): 4-(2-Methyl-1,2,3,4-tetrahydro-pyrido[4,3-b]indol-5-ylmethyl)benzoic acid methyl ester (20) (0.50 g, 1.5 mmol) and hydroxylamine hydrochloride (0.62 g, 9.0 mmol) were placed under argon and dissolved in 5 mL of methanol. To it was added a 25% sodium methoxide solution in methanol (2.6 g, 12 mmol) which resulted in the formation of a white precipitate. The reaction was stirred for 24 h after which the reaction was diluted with ethyl acetate (20 mL) and saturated sodium bicarbonate (20 mL). The organic layer was isolated and the aqueous layer was further extracted with ethyl acetate (2×10 mL). The combined organic layers were washed with brine (10 mL), dried ($Na_2SO_4$) and concentrated in vacuo. The crude extract was purified by HPLC to yield the title compound (TFA salt, 0.21 g, 31%) as a white solid. $^1$H NMR (400 MHz, DMSO): δ 11.17 (br, 1H), 10.17 (br, 1H), 9.00 (br, 1H), 7.67 (d, 2H, J=7.9 Hz), 7.48 (t, 2H, J=7.9 Hz), 7.17-7.06 (m, 4H), 5.44 (br, 2H), 4.50 (br, 2H), 3.60 (br, 2H), 3.10 (m, 2H), 3.00 (s, 3H). $^{13}$C NMR APT (100 MHz, MeOD): δ 141.5 (up), 137.0 (up), 132.3 (up), 131.7 (up), 127.7 (down), 126.9 (down), 124.8 (up), 122.3 (down), 120.2 (down), 118.2 (down), 110.6 (down), 102.7 (up), 51.0 (up), 50.6 (up), 46.0 (up), 42.3 (down), 20.1 (up). ESI-HRMS (m/z): [M+H]$^+$ calcd. for $C_{20}H_{21}N_3O_2$, 336.1707. found, 336.1708. Analytical HPLC: Purity=100%, $t_R$=5.71 min, Method A.

with reflux condenser containing 2-methyl-2,3,4,9-tetrahydro-1H-b-carboline (16) (0.30 g, 1.62 mmol) and potassium tert-butoxide (0.22 g, 1.92 mmol) was vacuum purged and filled with argon, followed by addition of DMSO (5 mL). After stirring at 120° C. for 20 min, 4-bromomethyl-benzoic acid methyl ester (0.37 g, 1.62 mmol) was added and the mixture was stirred at 120° C. for 3 h. The reaction was quenched by addition of water (30 mL), transferred to a separatory funnel and extracted with ethyl acetate (3×20 mL). The combined organic layers were washed with brine (2×20 mL), dried ($Na_2SO_4$) and concentrated. The product was purified by MPCC (0 to 5% gradient of MeOH in $CH_2Cl_2$), which gave 180 mg (33%) of the title compound. $^1$H NMR (400 MHz, CDCl$_3$): δ 7.95 (d, 2H, J=8.2 Hz), 7.54 (m, 1H, J=7.6 Hz), 7.18-7.11 (m, 4H), 7.15 (d, 2H, J=8.1 Hz), 5.25 (s, 2H), 3.89 (s, 3H), 3.53 (s, 2H), 2.90 (m, 2H), 2.80 (m, 2H), 2.51 (s, 3H). $^{13}$C NMR (100 MHz, CDCl$_3$): δ 166.5, 141.9, 137.4, 130.4, 126.0, 122.8, 120.2, 118.6, 109.4, 106.7, 52.2, 51.3, 49.7, 46.6, 45.56, 42.1, 18.5. ESI-HRMS (m/z): [M+H]$^+$ calcd. for $C_{21}H_{22}N_2O_2$, 335.1727. found, 335.1724.

N-Hydroxy-4-(2-methyl-1,2,3,4-tetrahydro-b-carbolin-9-ylmethyl)benzamide, trifluoroacetic acid salt (7): 4-(2-Methyl-1,2,3,4-tetrahydro-b-carbolin-9-ylmethyl)benzoic acid methyl ester (21) (0.15 g, 0.45 mmol) and hydroxylamine hydrochloride (0.19 g, 2.7 mmol) were placed under argon and dissolved in 2 mL of methanol. To it was added a 25% sodium methoxide solution in methanol (0.76 g, 3.6 mmol) which resulted in immediate precipitation of a white solid. The reaction was stirred for 24 h at room temperature after which was taken up in 20 mL ethyl acetate and 20 mL of saturated sodium bicarbonate. The organic layer was isolated and the aqueous layer was further extracted with ethyl acetate (2×10 mL). The combined organic layers were washed with brine (10 mL), dried with anhydrous sodium sulfate, filtered, and concentrated in vacuo. The crude extract was purified by HPLC to yield the title compound (TFA salt, 28 mg, 14%) as a white solid. 1H NMR (400 MHz, MeOD): δ 7.70 (d, 2H, J=6.63 Hz), 7.58 (d, 1H, J=7.9 Hz), 7.38 (d, 1H, J=8.17 Hz), 7.22 (t, 1H, J=6.97 Hz), 7.13 (m, 3H), 5.46 (s, 2H), 4.49 (m, 2H), 3.49 (m, 2H), 3.20 (t, 2H, J=6.48 Hz), 3.09 (s, 3H). $^{13}$C NMR (100 MHz, DMSO): δ 206.7, 158.6, 141.2, 137.2, 132.4, 127.8, 127.0, 126.0, 122.7, 120.1, 118.89, 110.6, 106.0, 51.6, 49.5, 46.2, 42.5, 18.7. ESI-HRMS (m/z): [M−H]$^-$ calcd. for $C_{20}H_{21}N_3O_2$, 334.1561. found, 334.1535. Analytical HPLC: Purity=98%, $t_R$=8.07 min, Method B.

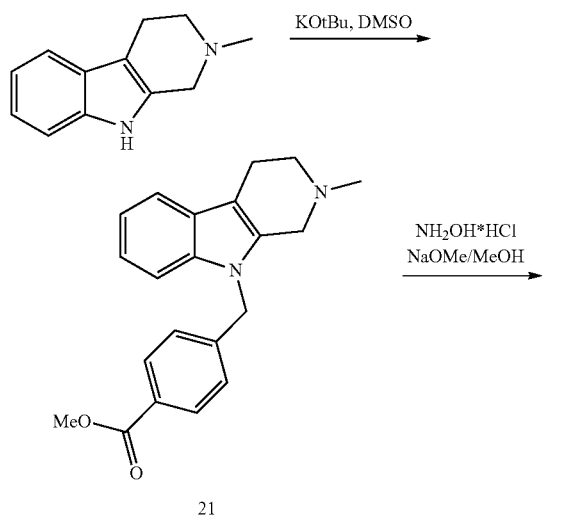

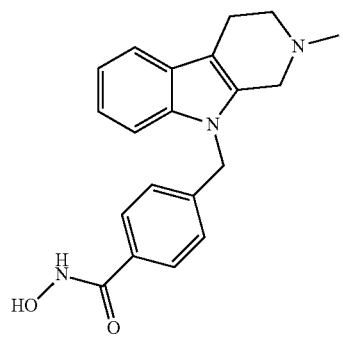

4-(2-Methyl-1,2,3,4-tetrahydro-b-carbolin-9-ylmethyl)benzoic acid methyl ester (21): A round bottom flask fitted

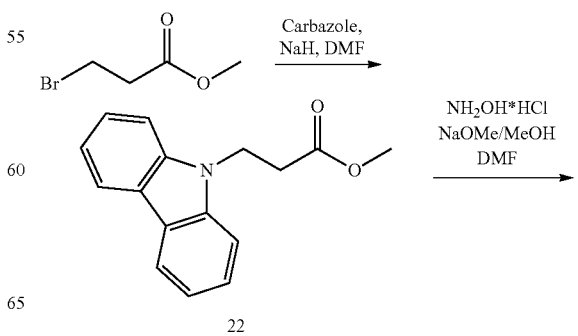

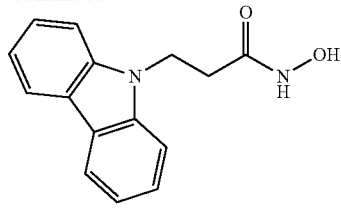

8

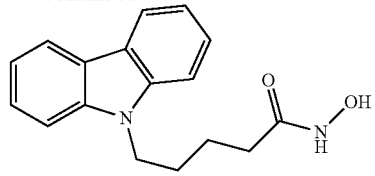

9

3-Carbazol-9-yl-propionic acid methyl ester (22): Carbazole (1.0 g, 5.98 mmol) and sodium hydride (60 wt. % in mineral oil, 0.36 g, 8.97 mmol) were placed under argon, dissolved in DMF (10 mL) and stirred for 20 min at 60° C. This was followed by addition of 6-bromo-propanoic acid methyl ester (0.65 mL, 5.98 mmol). The reaction was stirred at 60° C. for 4 h. The reaction was then diluted with ethyl acetate (30 mL) and water (30 mL). The organic layer was isolated and the aqueous layer extracted with ethyl acetate (2×20 mL). The combined organic layers were washed with brine (3×30 mL), dried ($Na_2SO_4$) and concentrated in vacuo. Purification by MPCC (0-20% gradient of ethyl acetate in hexane) afforded the title compound (735 mg, 49%). $^1$H NMR (400 MHz, $CDCl_3$): δ 8.12 (d, 2H, J=7.8 Hz), 7.49 (m, 4H), 7.27 (t, 2H, J=6.5 Hz), 4.68 (t, 2H, J=7.3 Hz), 3.67 (s, 3H), 2.89 (t, 2H, J=7.2 Hz). $^{13}$C NMR (100 MHz, $CDCl_3$): δ 171.8, 140.0, 125.8, 123.1, 120.4, 119.2, 108.6, 51.9, 38.7, 33.3. ESI-HRMS (m/z): [M+H]$^+$ calcd. for $C_{16}H_{15}NO_2$, 253.1103. found, 254.1154.

3-Carbazol-9-yl-N-hydroxy-propionamide (8): 3-Carbazol-9-yl-propionic acid methyl ester (22) (0.50 g, 1.97 mmol) and hydroxylamine hydrochloride (0.82 g, 12 mmol) were placed under argon and dissolved in DMF (8 mL). To it was added a 25% sodium methoxide solution in methanol (3.4 g, 16 mmol) which resulted in immediate precipitation of a white solid. The reaction was stirred for 24 h at room temperature after which was taken up in ethyl acetate (20 mL), water (10 mL) and of saturated aqueous $NaHCO_3$ (10 mL). The organic layer was isolated and the aqueous layer was further extracted with ethyl acetate (2×20 mL). The combined organic layers were washed with brine (10 mL), dried ($Na_2SO_4$) and concentrated in vacuo. The crude extract was purified by HPLC to yield the title compound (234 mg, 47%) as a white solid. $^1$H NMR (400 MHz, DMSO): δ 10.46 (s, 1H), 8.75 (s, 1H), 8.14 (d, 2H, J=7.7 Hz), 7.60 (d, 2H, J=8.0 Hz), 7.45 (t, 2H, J=7.2 Hz), 7.20 (t, 2H, J=7.6 Hz), 4.61 (t, 2H, J=6.8 Hz), 2.48 (m, 2H). $^{13}$C NMR (100 MHz, $CDCl_3$): δ 169.2, 140.2, 126.2, 122.6, 120.6, 119.3, 109.8, 39.3, 32.3. ESI-MS (m/z): [M+H]$^+$ 254.1. Analytical HPLC: Purity=97%, $t_R$=5.62 min, Method A.

5-Carbazol-9-ylpentanoic acid methyl ester (23): To a round bottom flask fitted with reflux condenser containing carbazole (1.00 g, 5.98 mmol) and sodium hydride (60 wt. % in mineral oil, 0.29 g, 7.18 mmol), was added DMF (22 mL). After stirring at 50° C. for 20 min, ethyl 5-bromopentanoate (0.95 mL, 5.98 mmol) was added and the mixture stirred at 80° C. overnight. The reaction was quenched by addition of 5% aqueous $NH_4Cl$ (100 mL), transferred to a separatory funnel and extracted with ethyl acetate (3×40 mL). The combined organic layers were washed with brine (2×20 mL), dried ($Na_2SO_4$) and concentrated. Purification by MPCC (0-40% gradient of ethyl acetate in hexane) afforded the title compound (0.87 g, 49%). $^1$H NMR (400 MHz, $CDCl_3$): δ 8.14 (d, 2H, J=7.8 Hz), 7.51 (t, 2H, J=7.2 Hz), 7.43 (d, 2H, J=8.2 Hz), 7.27 (t, 2H, J=7.4 Hz), 4.35 (t, 2H, J=7.1 Hz), 4.13 (q, 2H, J=7.1 Hz), 2.35 (t, 2H, J=7.3 Hz), 1.98-1.91 (m, 2H), 1.79-1.72 (m, 2H), 1.25 (t, 3H, J=7.1 Hz). $^{13}$C NMR APT (100 MHz, $CHCl_3$): δ 173.2 (up), 140.3 (up), 125.6 (down), 122.89 (up), 120.4 (down), 118.9 (down), 108.6 (down), 60.4 (up), 42.7 (up), 33.9 (up), 28.4 (up), 22.7 (up), 14.2 (down). ESI-HRMS (m/z): [M+H]$^+$ calcd. for $C_{19}H_{21}NO_2$, 296.1645. found, 296.1650.

5-Carbazol-9-yl-pentanoic acid hydroxyamide (9): 5-Carbazol-9-ylpentanoic acid methyl ester (23) (110 mg, 0.37 mmol) was converted to hydroxamic acid by procedure A. Purification by HPLC afforded the title product (26 mg, 25%). $^1$H NMR (400 MHz, MeOD): δ 8.07 (d, 2H, J=7.5 Hz), 7.49 (d, 2H, J=8.2 Hz), 7.43 (t, 2H, J=7.7 Hz), 7.20 (t, 2H, J=7.4 Hz), 4.40 (t, 2H, J=7.0 Hz), 2.09 (t, 2H, J=7.3 Hz), 1.88 (m, 2H), 1.68 (m, 2H). $^{13}$C NMR APT (100 MHz, $CD_3OD$): δ 140.3 (up), 125.3 (down), 122.7 (up), 119.7 (down), 118.4 (down), 108.5 (down), 41.9 (up), 32.1 (up), 28.1 (up), 23.1 (up). ESI-HRMS (m/z): [M+H]$^+$ calcd. for $C_{17}H_{18}N_2O_2$, 283.1441. found, 283.1448. Analytical HPLC: Purity=99%, $t_R$=5.65 min, Method A.

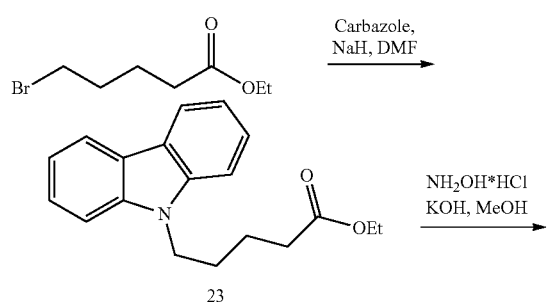

23

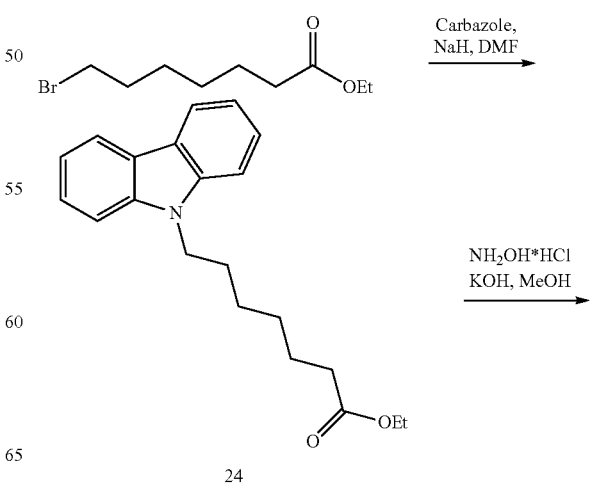

24

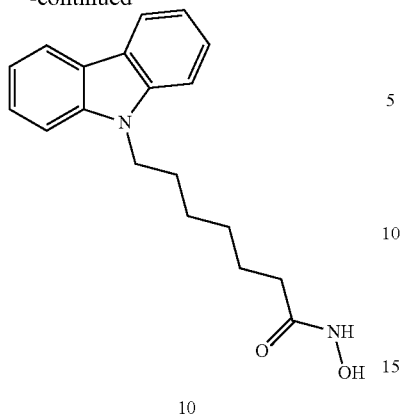

10

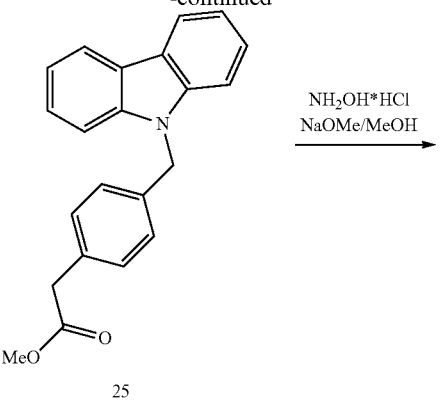

25

7-Carbazol-9-ylheptanoic acid ethyl ester (24): A RB flask fitted with reflux condenser containing carbazole (0.60 g, 3.59 mmol) and sodium hydride (60 wt. % in mineral oil, 0.22 g, 5.38 mmol) was vacuum purged and filled with argon, followed by addition of DMF (16 mL). After stirring at 50° C. for 20 min, ethyl 7-bromo-heptanoate (0.85 g, 3.59 mmol) was added and the mixture stirred at 80° C. overnight. The reaction was quenched by addition of 5% aqueous $NH_4Cl$ (75 mL), transferred to a separatory funnel and extracted with ethyl acetate (3×30 mL). The combined organic layers were washed with brine (2×20 L), dried ($Na_2SO_4$) and concentrated. Purification by MPCC (0-50% gradient of ethyl acetate in hexane) afforded the title compound (0.77 g, 66%). $^1$H NMR (300 MHz, $CDCl_3$): δ 8.15 (d, 2H, J=7.8 Hz), 7.52 (t, 2H, J=7.3 Hz), 7.44 (d, 2H, J=8.1 Hz), 7.28 (t, 2H, J=7.7 Hz), 4.32 (t, 2H, J=7.2 Hz), 4.16 (q, 2H, J=7.1 Hz), 2.30 (t, 2H, J=7.4 Hz), 1.91 (m, 2H), 1.64 (m, 2H), 1.41 (m, 4H), 1.30 (t, 3H, J=7.2 Hz). $^{13}$C NMR APT (100 MHz, $CDCl_3$): 173.7 (up), 140.5 (up), 125.6 (down), 122.9 (up), 120.4 (down), 118.8 (down), 108.7 (down), 60.3 (up), 43.0 (up), 34.3 (up), 28.9 (up), 27.0 (up), 24.8 (up), 14.3 (down). ESI-HRMS (m/z): $[M+H]^+$ calcd. for $C_{21}H_{25}NO_2$, 324.1958. found, 324.1957

7-Carbazol-9-ylheptanoic acid hydroxyamide (10): 7-Carbazol-9-ylheptanoic acid ethyl ester (24) (0.25 g, 0.77 mmol) was converted to hydroxamic acid by procedure A. Purification by HPLC gave the title compound (31 mg, 13%) as a white powder. $^1$H NMR (400 MHz, MeOD): δ 7.97 (d, 2H, J=7.7 Hz), 7.41-7.32 (m, 4H), 7.09 (t, 2H, J=7.1 Hz), 4.28 (t, 2H, J=7.4 Hz), 1.91 (t, 2H, J=7.3 Hz), 1.78 (m, 2H), 1.47 (m, 2H), 1.34-1.19 (m, 4H). $^{13}$C NMR APT (100 MHz, MeOD): δ 171.5 (up), 140.3 (up), 125.2 (down), 122.6 (up), 119.6 (down), 118.3 (down), 108.5 (down), 42.1 (up), 32.2 (up), 28.5 (up), 26.4 (up), 25.2 (up). ESI-MS (m/z): $[M+Na]^+$ 333.2. Analytical HPLC: Purity=99%, $t_R$=16.17 min, Method B.

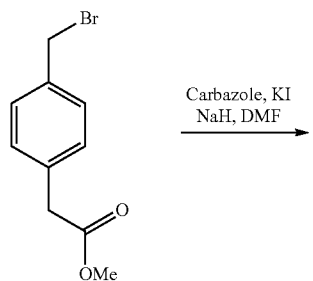

(4-Carbazol-9-ylmethyl-phenyl)acetic acid methyl ester (25): Carbazole (1.0 g, 6.0 mmol) and sodium hydride (60 wt. % in mineral oil, 0.14 g, 6.0 mmol) were placed under argon and dissolved in DMF (5 mL). The mixture was stirred at room temperature for 30 min, followed by treatment with (4-bromomethylphenyl)acetic acid methyl ester (1.5 g, 6.0 mmol) and 5 mg of potassium iodide. The reaction was heated to 80° C. for 2 h. The reaction was then diluted with ethyl acetate (30 mL) and water (30 mL). The organic layer was isolated and the aqueous layer extracted with ethyl acetate (2×10 mL). The combined organic layers were washed with water (2×20 mL), brine (15 mL), dried ($Na_2SO_4$) and concentrated in vacuo. Purification by column chromatography (0-80% gradient of ethyl acetate in hexane) afforded the title compound (0.71 g, 36%) as a yellow oil. $^1$H NMR (400 MHz, $CDCl_3$): δ 8.20 (d, 2H, J=7.7 Hz), 7.49 (m, 2H), 7.40 (d, 2H, J=8.1 Hz), 7.32 (m, 2H), 7.17 (d, 2H, J=8.1 Hz), 7.12 (d, 2H, J=8.1 Hz), 5.52 (s, 2H), 3.71 (s, 3H), 3.61 (s, 2H). $^{13}$C NMR (100 MHz, $CDCl_3$): δ 171.6, 140.3, 135.7, 132.8, 129.3, 126.5, 125.5, 122.8, 120.1, 118.9, 108.5, 51.7, 45.9, 40.4. ESI-HRMS (m/z): $[M+H]^+$ calcd. for $C_{22}H_{19}NO_2$, 330.1489. found, 330.1494.

2-(4-Carbazol-9-ylmethylphenyl)-N-hydroxyacetamide (11): (4-Carbazol-9-ylmethylphenyl)acetic acid methyl ester (25) (0.25 g, 0.8 mmol) and hydroxylamine hydrochloride (0.32 g, 4.6 mmol) were placed under argon and dissolved in 5 mL of methanol. To it was added a 25% sodium methoxide solution in methanol (1.33 g, 6.2 mmol) which resulted in the formation of a white precipitate. The reaction was stirred for 24 h at room temperature after which the reaction was diluted with ethyl acetate (20 mL) and saturated aqueous sodium bicarbonate (20 mL). The organic layer was isolated and the aqueous layer was further extracted with ethyl acetate (2×10 mL). The combined organic layers were washed with brine (10 mL), dried (Na$_2$SO$_4$) and concentrated in vacuo. The crude extract was purified by HPLC to yield the title compound (100 mg, 40%) as a white solid. $^1$H NMR (400 MHz, DMSO): δ 10.57 (s, 1H), 8.73 (s, 1H), 8.17 (d, 2H, J=7.7 Hz), 7.61 (d, 2H, J=8.2 Hz), 7.42 (t, 2H, J=7.5 Hz), 7.20 (t, 2H, J=7.4 Hz), 7.11 (m, 4H), 5.62 (s, 2H), 3.18 (s, 2H). $^{13}$C NMR (100 MHz, CD$_3$OD): δ 168.9, 140.2, 136.1, 133.8, 128.5, 126.0, 125.0, 122.5, 119.3, 118.4, 108.3, 45.0, 38.4. ESI-HRMS (m/z): [M+H]$^+$ calcd. for C$_{21}$H$_{18}$N$_2$O$_2$, 331.1441. found, 331.1445. Analytical HPLC: Purity=99%, $t_R$=6.82 min, Method A.

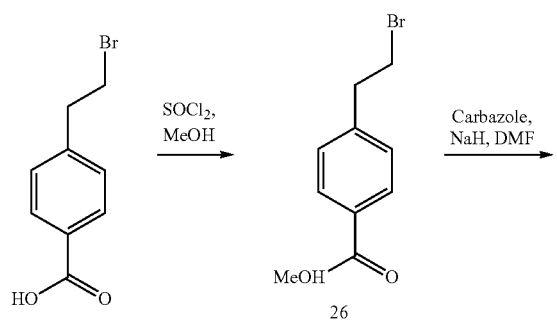

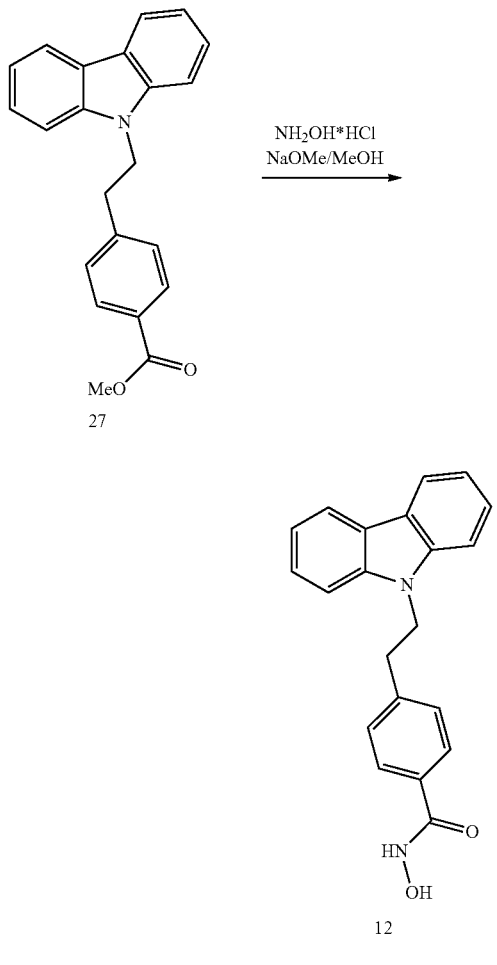

4-(2-Bromo-ethyl)benzoic acid methyl ester (26): 4-(2-Bromo-ethyl)-benzoic acid (1.00 g, 4.37 mmol) was dissolved in MeOH (10 mL) and cooled to 0° C. This was followed by dropwise addition of thionyl chloride (0.48 mL, 6.55 mmol). The mixture was refluxed for 2 h, followed by removal of all volatiles by rotary evaporation. The resulting oil was taken up in EtOAc (50 mL) and washed with water (50 mL). The EtOAc portion was separated, dried (Na$_2$SO$_4$) and concentrated to give the product (1.04 g, 98%) as a yellow oil. $^1$H NMR (400 MHz, CDCl$_3$) δ 8.00 (d, 2H, J=6.54 Hz), 7.29 (d, 2H, J=7.1 Hz), 3.92 (s, 3H), 3.59 (t, 2H, J=7.38 Hz), 3.23 (t, 2H, J=7.34 Hz).

4-(2-Carbazol-9-yl-ethyl)benzoic acid methyl ester (27): Carbazole (0.50 g, 2.99 mmol) and sodium hydride (60 wt. % in mineral oil, 0.14 g, 3.59 mmol) were placed under argon and dissolved in 6 mL of anhydrous DMF at room temperature, giving a dark brown solution. Following the evolution of hydrogen gas, 4-(2-bromo-ethyl)benzoic acid methyl ester (26) (0.73 g, 2.99 mmol) in DMF (2 mL) was added and the reaction was stirred at 70° C. for 2 h. The mixture was taken up in ethyl acetate (30 mL) and water (30 mL), the organic layer was separated and the aqueous layer extracted with ethyl acetate (2×10 mL). The combined organic layers were washed with brine (2×25 mL), dried (Na$_2$SO$_4$) and concentrated in vacuo. The residue was purified by MPCC(C$_{18}$, 10-100% gradient of MeOH in H$_2$O). The product co-eluted with unreacted carbazole. Cold MeOH (8 mL) was added to the product mixture and the suspension was filtered to remove the solid carbazole. The filtrate was concentrated to give the title compound (291 mg, 43%) as a red solid. $^1$H NMR (400 MHz, CDCl$_3$): δ 8.11 (m, 2H), 7.92 (d, 2H, J=8.0 Hz), 7.43 (m, 2H), 7.30 (m, 2H), 7.25 (m, 4H), 4.55 (t, 2H, J=7.3 Hz), 3.91 (s, 3H), 3.20 (t, 2H, J=7.4 Hz). $^{13}$C NMR (100 MHz, CDCl$_3$): δ 167.0, 144.1, 140.1, 123.0, 128.9, 125.8, 122.9, 120.4, 119.4, 110.6, 108.4, 52.1, 44.4, 35.2. ESI-HRMS (m/z): [M+H]$^+$ calcd. for C$_{22}$H$_{19}$NO$_2$, 330.1489. found, 330.1460.

4-(2-Carbazol-9-yl-ethyl)-N-hydroxy-benzamide (12): 4-(2-Carbazol-9-ylethyl)benzoic acid methyl ester (27) (0.15 g, 0.46 mmol) and hydroxylamine hydrochloride (0.19 g, 2.7 mmol) were placed under argon and dissolved in DMF (3 mL). To this was added a 25% sodium methoxide solution in methanol (0.79 g, 3.6 mmol) which resulted in immediate precipitation of a white solid. The reaction was stirred for 24 h at room temperature after which it was taken up in 20 mL ethyl acetate and 20 mL of saturated sodium bicarbonate. The organic layer was isolated and the aqueous layer was further extracted with ethyl acetate (2×10 mL). The combined organic layers were washed with brine (10 mL), dried (Na$_2$SO$_4$) and concentrated in vacuo. The crude extract was purified by HPLC to yield the title compound (10 mg, 7%) as an off-white solid. $^1$H NMR (400 MHz, DMSO): δ 11.14 (br, 1H), 8.14 (d, 2H, J=7.8 Hz), 7.62 (m, 4H), 7.40 (m, 4H), 7.18 (t, 2H, J=7.6 Hz), 4.62 (t, 2H, J=7.0 Hz), 3.11 (t, 2H, J=7.6 Hz). $^{13}$C NMR (100 MHz, DMSO): δ 140.2, 129.4, 127.3, 126.1, 122.5, 120.7, 119.2, 109.7, 44.1, 34.7. ESI-HRMS (m/z): [M−H]$^−$ calcd. for C$_{21}$H$_{18}$N$_2$O$_2$, 329.1298. found, 329.1273. Analytical HPLC: Purity=100%, $t_R$=9.13 min, Method B.

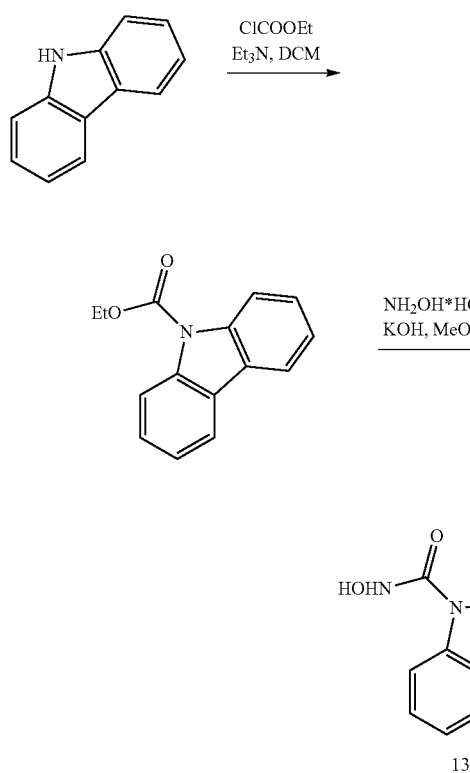

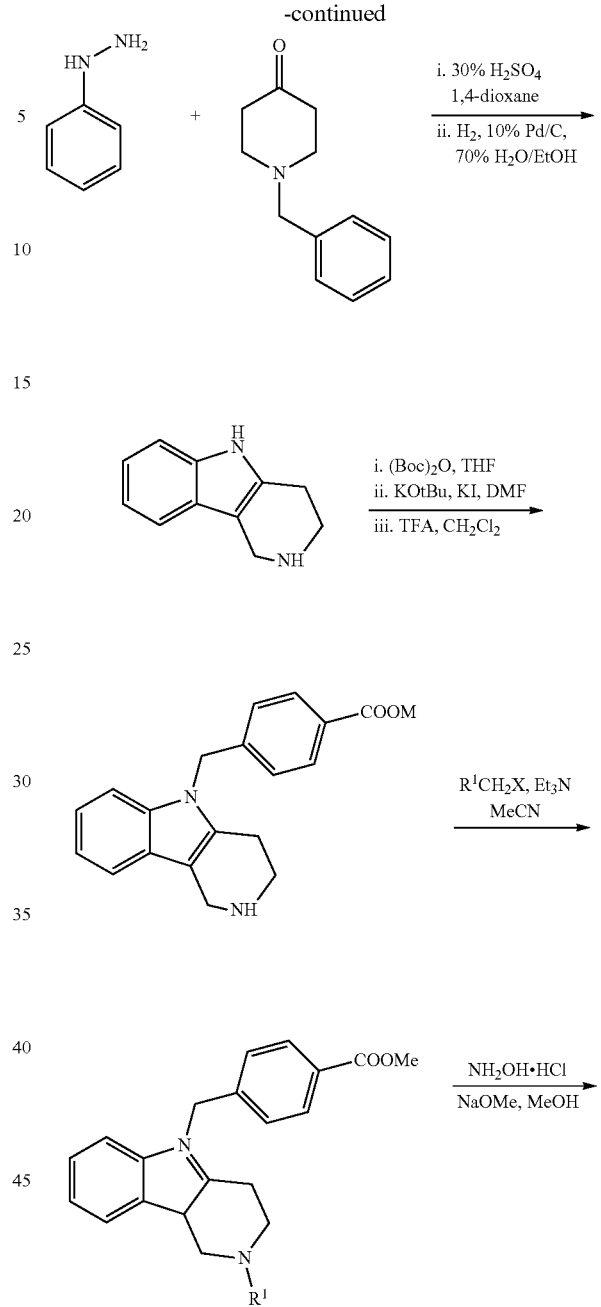

Carbazole-9-carboxylic acid hydroxyamide (13): An argon filled RB flask containing carbazole (0.500 g, 2.99 mmol) at 0° C. was treated with dichloromethane (12.5 mL) and triethylamine (2.5 mL), followed by slow addition of ethyl chloroformate (0.59 mL, 5.98 mmol). The mixture was stirred at ambient temperature for 16 h, poured into 25 mL of 2N HCl, and extracted with chloroform. The organic portion was washed with saturated aqueous $NaHCO_3$ and brine, dried ($Na_2SO_4$) and concentrated. The crude product was treated with methanol (4 mL) and filtered. The filtrate was concentrated to give carbazole-9-carboxylic acid ethyl ester (169 mg). Carbazole-9-carboxylic acid ethyl ester (95 mg, 0.39 mmol) was converted to hydroxamic acid by procedure A. Purification by HPLC gave the title compound (19 mg). $^1$H NMR (400 MHz, $CD_3CN$): δ 9.43 (br, 1H), 8.08 (d, 2H, J=7.7 Hz), 7.50 (d, 2H, J=8.1 Hz), 7.43 (t, 2H, J=7.1 Hz), 7.22 (t, 2H, J=7.1 Hz). $^{13}$C NMR APT (100 MHz, $CD_3OD$): δ 125.8 (down), 120.3 (down), 119.4 (down), 110.6 (down). ESI-MS (m/z): [M+Na]$^+$249.6. Analytical HPLC: Purity=99%, $t_R$=8.51 min, Method A.

General Procedure B:

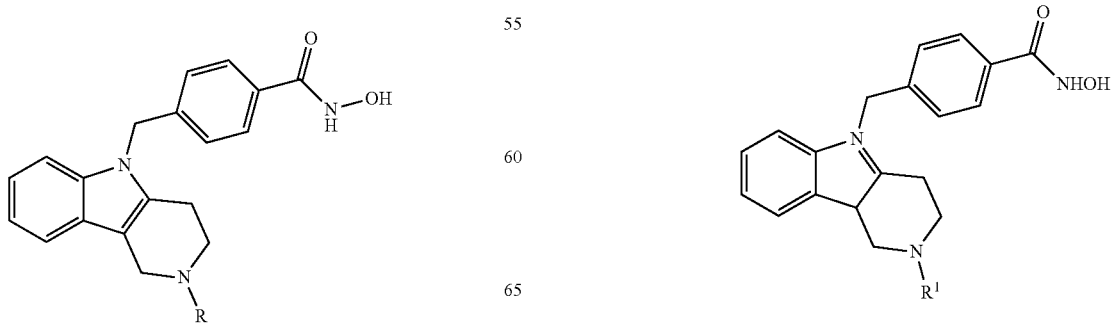

General Procedure C:
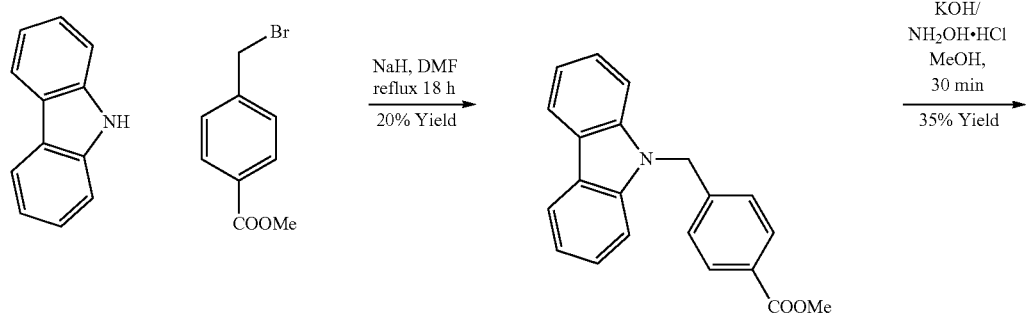
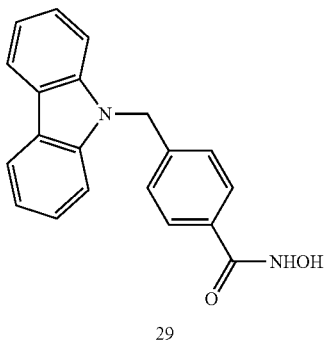
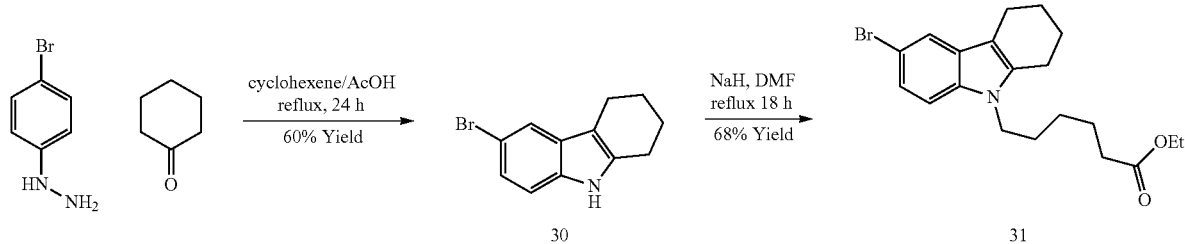
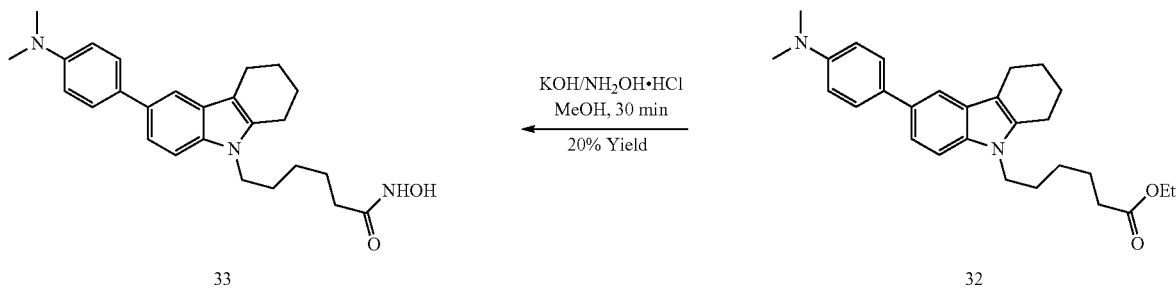

Synthetic Details

4-Carbazol-9-ylmethyl-benzoic acid methyl ester (28)

Carbazole (0.80 g, 4.80 mmol) and sodium hydride (NaH) (60% in mineral oil, 0.25 g, 6.2 mmol) were added to a flask, which was charged with argon. DMF (dimethylformamide) (12 mL) was added and the mixture was stirred at 60° C. for 1 hour (h), after which 4-bromomethyl benzoic acid methyl ester (1.16 g, 4.8 mmol) was added, and the mixture was stirred at 80° C. overnight. Water was added and the product was extracted with $CH_2Cl_2$ (dichloromethane), dried ($Na_2SO_4$, sodium sulfate) and concentrated. The product was purified by column chromatography to give 310 mg of compound 28 as a white solid.

4-Carbazol-9-ylmethyl-N-hydroxy-benzamide (29)

Potassium hydroxide (KOH) (85%, 5.2 g) and hydroxylamine hydrochloride ($NH_2OH.HCl$) (4.8 g) were dissolved in 30 mL methanol (MeOH) and stirred at 0° C. for 15 minutes (min), after which the solid was filtered off and the filtrate was added to 4-carbazol-9-ylmethyl-benzoic acid ethyl ester (28) (125 mg) and stirred for 30 min. The solvent was evaporated and the residue was treated with water and extracted with $CH_2Cl_2$, dried ($Na_2SO_4$), and concentrated. The product was purified by HPLC to give 38 mg of compound 2 as a light brown solid. $^1H$ NMR (400 MHz, $CDCl_3$): δ8.03 (d, 2H), 7.52 (d, 2H), 7.30 m, 4H), 7.11 (m, 4H), 5.55 (s, 2H) 1.93 (s, 1H). ESI-MS: m/z $[M+Na]^+$: 339.1

6-Bromo-2,3,4,9-tetrahydro-1H-carbazole (30)

Cyclohexanone (1.16 mL, 11.2 mmol) and 4-bromo-phenylhydrazine hydrochloride (2.50 g, 11.2 mmol) were refluxed in cyclohexanone (18 mL) and acetic acid (AcOH) (12 L) for 24 h. The reaction mixture was treated with saturated sodium bicarbonate ($Na_2CO_3$) and extracted with ethyl acetate, dried ($Na_2CO_3$) and concentrated. The product was purified by column chromatography, giving 479 mg of compound 30 as a solid.

6-(6-Bromo-1,2,3,4-tetrahydro-carbazol-9-yl)-hexanoic acid ethyl ester (31)

Compound 31 was prepared from 6-bromo-2,3,4,9-tetrahydro-1H-carbazole (30) (1.50 g, 6.00 mmol) and ethyl 6-bromohexanoate (1.34 g, 6.00 mmol) using the procedure described above for compound 28 as a solid (1.453 g).

6-[6-(4-Dimethylamino-phenyl)-1,2,3,4-tetrahydro-carbazol-9-yl]-hexanoic acid ethyl ester (32)

4-Dimethylamino boronic acid (0.221 g, 1.34 mmol), tetrabutylammonium bromide (TBAB) (0.049 g, 1.25 mmol), palladium acetate ($Pd(OAc)_2$ (0.017 g, 0.08 mmol), triorthotoluene phosphine ($P(o-toluene)_3$ (0.035 g, 0.12 mmol), and 6-(6-bromo-1,2,3,4-tetrahydro-carbazol-9-yl)-hexanoic acid ethyl ester (compound 4) (0.300 g, 0.76 mmol) were added to a flask, dissolved in toluene (3 mL), ethanol (2 mL), and 2M $Na_2CO_3$ (1 mL), and stirred overnight at 70° C. Compound 32 was purified by column chromatography to give 310 mg of the product as a solid.

6-[6-(4-Dimethylamino-phenyl)-1,2,3,4-tetrahydro-carbazol-9-yl]-hexanoic acid hydroxyamide (33)

Compound 33 was prepared from 6-(6-bromo-1,2,3,4-tetrahydro-carbazol-9-yl)-hexanoic acid ethyl ester (compound 32) using the procedure described above for compound 29 as a white solid (85%). $^1H$ NMR (400 MHz, MeOD): δ 7.86 (d, 2H), 7.65 (m, 3H), 7.33 (s, 2H), 4.09 (t, 2H), 2.76 (m, 4H), 2.16 (s, 1H), 2.08 (t, 2H), 1.98 (m, 2H), 1.90 (m, 2H), 1.77 (m, 2H), 1.66 (m, 2H), 1.38 (m, 2H).

The effectiveness, or potency, of an HDACI of structural formula (I) with respect to inhibiting the activity of an HDAC is measured by an $IC_{50}$ value. The quantitative $IC_{50}$ value indicates the concentration of a particular compound that is needed to inhibit the activity of an enzyme by 50% in vitro. Stated alternatively, the $IC_{50}$ value is the half maximal (50%) inhibitory concentration of a compound tested using a specific enzyme, e.g., HDAC, of interest. The smaller the $IC_{50}$ value, the more potent the inhibiting action of the compound because a lower concentration of the compound is needed to inhibit enzyme activity by 50%.

In preferred embodiments, a present HDACI inhibits HDAC enzymatic activity by about at least 50%, preferably at least about 75%, at least 90%, at least 95%, or at least 99%.

Compounds of the present invention were tested for $IC_{50}$ values against both HDAC6 and HDAC1. In some embodiments, a present compound also was tested against HDAC1, 2, 3, 4, 5, 8, 10, and 11. The tested compounds showed a range of $IC_{50}$ values vs. HDAC6 of about 1 nm to greater than 30 µm, and a range of $IC_{50}$ value vs. HDAC1 of about 91 nm to greater than 30 µm. Therefore, in some embodiments, an HDAC of structural formula (I) is a selective HDAC6 inhibitor which, because of a low affinity for other HDAC isozymes, e.g., HDAC1, give rise to fewer side effects than compounds that are non-selective HDAC inhibitors.

In some embodiments, the present HDACIs interact with and reduce the activity of all histone deacetylases in a cell. In some preferred embodiments, the present HDACIs interact with and reduce the activity of fewer than all histone deacetylases in the cell. In certain preferred embodiments, the present HDACIs interact with and reduce the activity of one histone deacetylase (e.g., HDAC-6), but do not substantially interact with or reduce the activities of other histone deacetylases (e.g., HDAC-1, HDAC-2, HDAC-3, HDAC-4, HDAC-5, HDAC-7, HDAC-8, HDAC-9, HDAC-10, and HDAC-11).

The present invention therefore provides HDACIs of structural formula (I) for the treatment of a variety of diseases and conditions wherein inhibition of HDAC has a beneficial effect. Preferably, a compound of structural formula (I) is selective for HDAC6 over the other HDAC isozymes by a factor of at least 2, at least 5, at least 10, at least 20, at least 50, at least 100, at least 500, at least 1000, at least 2000, at least 3000, and preferably up to about 4000. For example, in various embodiments, an HDACI of structural formula (I) exhibits an $IC_{50}$ value versus HDAC6 that is about 350 or about 1000 times less than the $IC_{50}$ value vs. HDAC1, i.e., a selectivity ratio (HDAC1 $IC_{50}$/HDAC6 $IC_{50}$) of about 350 or about 1000.

Other assays also showed a selectivity of a present compound for HDAC6 over HDAC1, 2, 3, 4, 5, 8, 10, and 11 of about 1000.

The $IC_{50}$ values for compounds of structural formula (I) vs. HDAC 1 and HDAC6 were determined as follows:

The HDAC1, 2, 4, 5, 6, 7, 8, 9, 10, and 11 assays used isolated recombinant human protein; HDAC3/NcoR2 complex was used for the HDAC3 assay. Substrate for HDAC1, 2, 3, 6, 10, and 11 assays is a fluorogenic peptide from p53 residues 379-382 (RHKKAc); substrate for HDAC8 is fluorogenic diacyl peptide based on residues 379-382 of p53 ($RHK_{Ac}K_{Ac}$). Acetyl-Lys(trifluoroacetyl)-AMC substrate was used for HDAC4, 5, 7, and 9 assays. Compounds were dissolved in DMSO and tested in 10-dose $IC_{50}$ mode with 3-fold serial dilution starting at 30 μM. Control Compound Trichostatin A (TSA) was tested in a 10-dose $IC_{50}$ with 3-fold serial dilution starting at 5 $IC_{50}$ values were extracted by curve-fitting the dose/response slopes. Assays were performed in duplicate and $IC_{50}$ values are an average of data from both experiments.

Materials

Human HDAC1 (GenBank Accession No. NM_004964): Full length with C-terminal GST tag, MW=79.9 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >10% by SDS-PAGE. Specific Activity is 20 U/μg, where one U=1 pmol/min under assay condition of 25 mM Tris/Cl, pH8.0, 137 mM NaCl, 2.7 mM KCl, 1 mM $MgCl_2$, 0.1 mg/ml BSA, 100 μM HDAC substrate, and 13.2 ng/μl HDAC1, incubation for 30 mM at 30° C.

Human HDAC6 (GenBank Accession No. BC069243): Full length with N-terminal GST tag, MW=159 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >90% by SDS-PAGE. Specific Activity is 50 U/μg, where one U=1 pmol/min under assay condition of 25 mM Tris/Cl, pH8.0, 137 mM NaCl, 2.7 mM KCl, 1 mM $MgCl_2$, and 0.1 mg/ml BSA, 30 μM HDAC substrate, and 5 ng/μl HDAC6, incubation for 60 min at 30° C.

Substrate for HDAC1 and HDAC6: Acetylated peptide substrate for HDAC, based on residues 379-382 of p53 (Arg-His-Lys-Lys(Ac)), a site of regulatory acetylation by the p300 and CBP acetyltransferases (lysines 381, 382) 1-6, is the best for HDAC from among a panel of substrates patterned on p53, histone H3 and histone H4 acetylation sites7.

References: W. Gu et al., Cell (1997) 90 595; K. Sakaguchi et al., Genes Dev., (1998) 12 2831; L. Liu et al., Mol. Cell. Biol., (1999) 19 1202; A. Ito et al., EMBO J., (2001) 20 1331; N. A. Barley et al., Mol. Cell, (2001) 8 1243; and A. Ito et al., EMBO J., (2002) 21 6236.

Reaction Buffer: 50 mM Tris-HCl, pH 8.0, 137 mM NaCl, 2.7 mM KCl, 1 mM $MgCl_2$, 1 mg/ml BSA.

Assay Conditions

HDAC1: 75 nM HDAC1 and 50 μM HDAC substrate are in the reaction buffer and 1% DMSO final. Incubate for 2 hours at 30° C.

HDAC6: 12.6 nM HDAC6 and 50 μM HDAC substrate are in the reaction buffer and 1% DMSO final. Incubate for 2 hours at 30° C.

$IC_{50}$ Calculations

All $IC_{50}$ values are automatically calculated using the GraphPad Prism version 5 and Equation of Sigmoidal dose-response (variable slope):

Y=Bottom+(Top-Bottom)/(1+10^((LogEC50-X)*HillSlope)), where X is the logarithm of concentration, Y is the response, Y starts at Bottom and goes to Top with a sigmoid shape. In most cases, "Bottom" is set 0, and "Top" is set "less than 120%". This is identical to the "four parameter logistic equation". $IC_{50}$ curves also are drawn using the GraphPad Prism, and $IC_{50}$ values and Hill slopes are provided.

HDAC Activity Assays: HDAC assay is performed using fluorescently-labeled acetylated substrate, which comprises an acetylated lysine side chain. After incubation with HDAC, deacetylation of the substrate sensitizes the substrate such that, in a second step, treatment with the detection enzyme produces a fluorophore. HDACs 1 and 6 were expressed as full length fusion proteins. Purified proteins were incubated with 50 μM fluorescently-labeled acetylated peptide substrate and test compound for 2 hours at room temperature in HDAC assay buffer containing 50 mM Tris-HCl (pH 8.0), 137 mM NaCl, 2.7 mM KCl, 1 mM $MgCl_2$, 1% DMSO, and 1% BSA.

Reactions were terminated by the addition of the Developer after 2 hours, and the development of fluorescence signal, which was relative to the amount of deacetylated peptide, was monitored by time-course measurement of EnVision (PerkinElmer). The HDAC activity was estimated from the slope of time-course measurement of the fluorescence intensity. The slope of no-enzyme control (substrate alone) was served as background, and % Enzyme activity was calculated using background-subtracted slope of no inhibitor control (DMSO) as 100% activity.

To date, HDACIs have demonstrated a relatively non-specific inhibition of various HDAC isozymes. Most HDACI so far identified primarily inhibit HDAC 1, 2, 3, and 8, producing an antiproliferative phenotype which is useful for oncology applications, but not for the many non-oncology applications of HDACIs. (K. B. Glaser et al, Biochemical and biophysical research communications 2003, 310, 529-36.) The potential toxicities associated with the inhibition of certain HDAC isozymes can lead to additional difficulties for the clinical development of pan-HDAC, i.e., nonselective HDAC, inhibitors. Because the network of cellular effects mediated by acetylation is so vast and because inhibition of some HDAC isozymes may lead to undesirable side effects, HDAC isozyme selective inhibitors hold a greater therapeutic promise than their nonselective counterparts.

As illustrated below, many HDACIs of the present invention exhibit selective inhibition of HDAC6 compared to other HDAC isozymes.

TABLE 1

HDAC inhibition data for compounds 1-7 and comparative HDAC inhibitors.

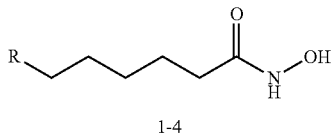

1-4

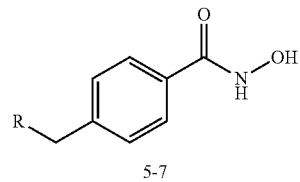

5-7

TABLE 1-continued
HDAC inhibition data for compounds 1-7 and comparative HDAC inhibitors.
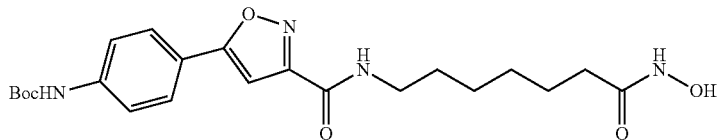
ISOX
(Comparative)
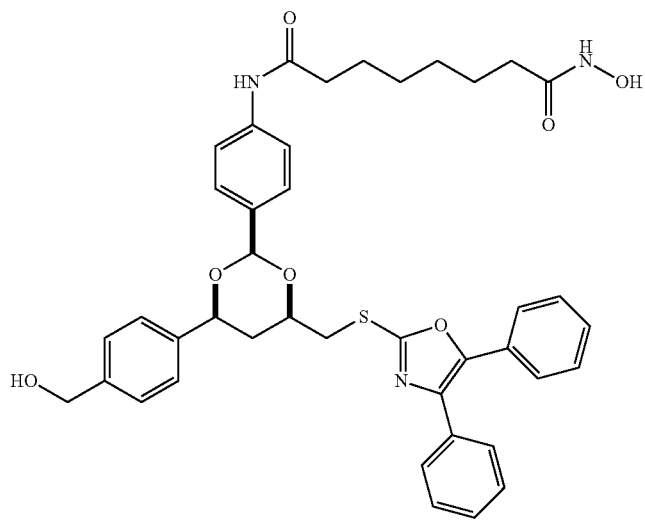
Tubacin
(Comparative)
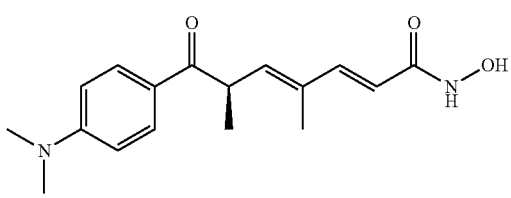
TSA
(Comparative)
| | R = | HDAC1 IC$_{50}$ (μM) ± SD | HDAC6 IC$_{50}$ (μM) ± SD |
|---|---|---|---|
| 1 | carbazole | 14.0 ± 4.8 | 0.062 ± 0.004 |
| 2 | 1,2,3,4-tetrahydrocarbazole | 8.6 ± 3.7 | 0.090 ± 0.019 |
| 3 | N-Me tetrahydro-β-carboline | >30 | 0.550 ± 0.002 |

TABLE 1-continued

HDAC inhibition data for compounds 1-7 and comparative HDAC inhibitors.

| | | | |
|---|---|---|---|
| 4 | 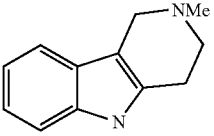 | 25.2 ± 3.3 | 0.213 ± 0.044 |
| 5 | 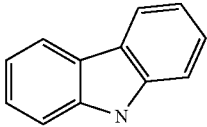 | 10.9 ± 3.4 | 0.019 ± 0.001 |
| 6 | 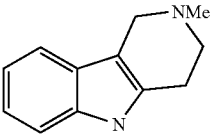 | 13.8 ± 2.6 | 0.014 ± 0.001 |
| 7 | 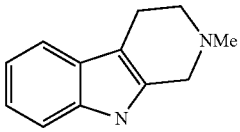 | 5.18 ± 0.12 | 0.0014 ± 0.0003 |
| TSA | N/A | 4.74 ± 1.26 | 1.21 ± 0.49 |
| Tubacin | N/A | 1.40 ± 0.24 | 0.004 ± 0.001 |
| ISOX | N/A | 0.071 ± 0.059 | 0.0024 ± 0.0021 |

Data are shown as $IC_{50}$ values in µM±standard deviation. Values are the mean of two experiments, except TSA, which is a mean of 9 experiments. Compounds were tested in duplicate in a 10-dose $IC_{50}$ mode with 3-fold serial dilution starting from 30 µM solutions. $IC_{50}$ values were extracted by curve-fitting the dose/response slopes. TSA was used as an internal standard.

Assays values are an average of two experiments. ISOX was previously found to have a low picomolar $IC_{50}$ at HDAC6. When ISOX was tested in these assays, an HDAC6 $IC_{50}$ value of 2.4 nM was observed. After investigating the source of this discrepancy, it was found that lack of a detergent (Triton X100) in the original assay caused the anomalously high activity.

Compound 6 demonstrates excellent HDAC6 potency and selectivity, with an $IC_{50}$ of 14 nM at HDAC6 and an about 1000-fold selectivity against HDAC1. Compound 7 demonstrated even greater potency and selectivity, with an $IC_{50}$ of 1.4 nM at HDAC6 and 3700-fold selectivity against HDAC 1. Compounds 5-7 exhibited greatly enhanced activity and selectivity compared to compounds 1-4. It is theorized, but not relied upon, that the tolyl linker imparts a bent conformation which forces tighter interactions between the tricycle and the catalytic channel rim, giving a greater response to structural changes made to the tricycle. It is further theorized, but not relied upon, that the enhanced selectivity of the carboline derivatives also may result from the presence of the N-methyl group because this substituent further expands the dimensions of the cap group, thus further favoring interactions with HDAC6.

The present HDACIs were compared to other compounds reported to be highly selective for HDAC6. Tubacin was found to potently inhibit HDAC6, with an $IC_{50}$ value of 4 nM and 350-fold selectivity over HDAC1. Compounds 6 and 7 are far more selective for HDAC6 than any other compounds reported in literature. Compounds 6 and 7 also possess properties making them useful drug products, e.g., ClogP=2.41 (KOWWIN) and tPSA=57 for both compounds 6 and 7; AlogPs water solubility=45.2 mg/l for compound 6 and 43.7 g/l for compound 7. The tertiary amine group of the compounds can be used to form pharmaceutically useful salts, thus facilitating compound solubilization. Furthermore, their facile, three-step syntheses allow easy scale-up for in vivo studies.

Compound 6 was profiled against all 11 HDAC isozymes to investigate its ability to induce α-tubulin acetylation in cells, as well as to profile its neuroprotective action in a cell model of oxidative stress. Tubacin also was tested at all 11 HDAC isoforms (Table 2). Compound 6 was substantially more selective than Tubacin at all isozymes, except HDAC8, and maintained over 1000-fold selectivity against all isoforms excluding HDAC8, where it displayed 58-fold selectivity. The moderate activity of compound 6 at HDAC8 may be the product of a known conformational change that occurs upon binding to HDAC8, which dilates the catalytic pocket, to better accommodate the bulky tricyclic group. (J. R. Somoza et al., Structure 2004, 12, 1325-34.)

TABLE 2

Enzyme inhibition data for Tubacin and Compound 6 at all 11 HDAC isozymes.

| | Tubacin $IC_{50}$ (µM) ± SD | Compound 6 $IC_{50}$ (µM) ± SD |
|---|---|---|
| HDAC1 | 1.40 ± 0.24 | 13.8 ± 2.6 |
| HDAC2 | 6.27 ± 0.29 | >30 |
| HDAC3 | 1.27 ± 0.16 | >30 |
| HDAC4 | 17.3 ± 2.1 | >30 |
| HDAC5 | 3.35 ± 0.03 | >30 |
| HDAC6 | 0.004 ± 0.001 | 0.014 ± 0.001 |

TABLE 2-continued

Enzyme inhibition data for Tubacin and Compound 6 at all 11 HDAC isozymes.

|   | Tubacin IC$_{50}$ (µM) ± SD | Compound 6 IC$_{50}$ (µM) ± SD |
|---|---|---|
| HDAC7 | 9.7 ± 1.8 | >30 |
| HDAC8 | 1.27 ± 0.16 | 0.814 ± 0.040 |
| HDAC9 | 4.31 ± 0.34 | >30 |
| HDAC10 | 3.71 ± 0.16 | >30 |
| HDAC11 | 3.79 ± 0.10 | >30 |

Values are the mean of two experiments. Data are shown as IC$_{50}$ values in µM±standard deviation. Compounds were tested in duplicate in 10-dose IC$_{50}$ mode with 3-fold serial dilution starting from 30 µM solutions. IC$_{50}$ values were extracted by curve-fitting the dose/response slopes.

The following table provides additional information showing the potency and selectivity of HDACIs 8-13 vs. HDAC1 and HDAC6.

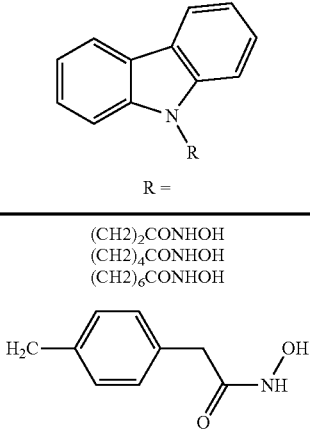

|    | R = | HDAC1 IC$_{50}$ (µM) ± SD | HDAC6 IC$_{50}$ (µM) ± SD |
|----|-----|---------------------------|---------------------------|
| 8  | (CH2)$_2$CONHOH | >30 | 1.59 ± 0.08 |
| 9  | (CH2)$_4$CONHOH | 12.8 ± 0.7 | 2.63 ± 0.04 |
| 10 | (CH2)$_6$CONHOH | 0.204 ± 0.087 | 0.006 ± 0.002 |
| 11 | 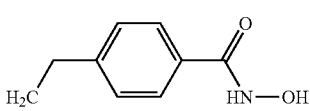 | >30 | 0.301 ± 0.009 |
| 12 | (structure shown) | >30 | 0.180 ± 0.018 |
| 13 | CONHOH | >30 | >30 |

Values are the means of two experiments. Data is shown as IC$_{50}$ values in µM±standard deviation. Compounds were tested in duplicate in 10-dose IC$_{50}$ mode with 3-fold serial dilution starting from 30 µM solutions. IC$_{50}$ values were extracted by curve-fitting the dose/response slopes.

In one embodiment, the present invention relates to a method of treating an individual suffering from a disease or condition wherein inhibition of HDACs provides a benefit comprising administering a therapeutically effective amount of a compound of structural formula (I) to an individual in need thereof.

The methods described herein relate to the use of an HDACI of structural formula (I) and an optional second therapeutic agent useful in the treatment of diseases and conditions wherein inhibition of HDAC provides a benefit. The methods of the present invention can be accomplished by administering an HDACI of structural formula (I) as the neat compound or as a pharmaceutical composition. Administration of a pharmaceutical composition, or neat HDACI of structural formula (I), can be performed during or after the onset of the disease or condition of interest. Typically, the pharmaceutical compositions are sterile, and contain no toxic, carcinogenic, or mutagenic compounds that would cause an adverse reaction when administered.

In many embodiments, an HDACI of structural formula (I) is administered in conjunction with a second therapeutic agent useful in the treatment of a disease or condition wherein inhibition of HDAC provides a benefit. The second therapeutic agent is different from the HDACI of structural formula (I). An HDACI of structural formula (I) and the second therapeutic agent can be administered simultaneously or sequentially. In addition, an HDACI of structural formula (I) and second therapeutic agent can be administered from a single composition or two separate compositions. An HDACI of structural formula (I) and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein inhibition of HDAC provides a benefit. The present invention also is directed to pharmaceutical compositions comprising an HDACI of structural formula (I) and an optional second therapeutic agent useful in the treatment of diseases and conditions wherein inhibition of HDAC provides a benefit. Further provided are kits comprising an HDACI of structural formula (I) and, optionally, a second therapeutic agent useful in the treatment of diseases and conditions wherein inhibition of HDAC provides a benefit, packaged separately or together, and an insert having instructions for using these active agents.

An HDACI of structural formula (I) and the second therapeutic agent can be administered together as a single-unit dose or separately as multi-unit doses, wherein the an HDACI of structural formula (I) is administered before the second therapeutic agent or vice versa. One or more dose of an HDACI of structural formula (I) and/or one or more dose of the second therapeutic agent can be administered. The HDACIs of structural formula (I) therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, an HDACI of structural formula (I) is a potent inhibitor of HDAC and can be used in treating diseases and conditions wherein inhibition of HDAC provides a benefit, for example, cancer, a neurological disease, a neurodegenerative condition, traumatic brain injury, stroke, an inflammation, an autoimmune disease, autism, and malaria.

In one preferred embodiment, the present invention provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof a therapeutically effective amount of an HDACI of structural formula (I).

In one embodiment, the invention provides a method for treating cancer comprising administering to a subject in need thereof an amount of an HDACI of structural formula (I) or a pharmaceutically acceptable salt thereof sufficient to treat the cancer. An HDACI of structural formula (I) can be used as the sole anticancer agent, or in combination with another anticancer treatment, e.g., radiation, chemotherapy, and surgery.

In another embodiment, the invention provides a method for increasing the sensitivity of a cancer cell to the cytotoxic effects of radiotherapy and/or chemotherapy comprising contacting the cell with an HDACI of structural formula (I) or a pharmaceutically acceptable salt thereof in an amount sufficient to increase the sensitivity of the cell to the cytotoxic effects of radiotherapy and/or chemotherapy.

In a further embodiment, the present invention provides a method for treating cancer comprising: (a) administering to an individual in need thereof an amount of a compound of structural formula (I); and (b) administering to the individual an amount of radiotherapy, chemotherapy, or both. The amounts administered are each effective to treat cancer. In another embodiment, the amounts are together effective to treat cancer.

In another embodiment, the invention provides a method for treating cancer, said method comprising administering to a subject in need thereof a pharmaceutical composition comprising an amount of an HDACI of structural formula (I) effective to treat cancer.

This combination therapy of the invention can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myclomonocytic leukemia, acute nonlymphocyctic leukemia, acute undifferentiated leukemia, chronic myclocytic leukemia, chronic lymphocytic leukemia, hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

The HDACIs of structural formula (I) can also be administered to prevent progression to a neoplastic or malignant state, including but not limited to the cancers listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where chronic irritation or inflammation exists, and often is found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include, for example, morphology changes, looser substratum attachment, loss of contact inhibition, loss of anchorage dependence, protease release, increased sugar transport, decreased serum requirement, expression of fetal antigens, disappearance of the 250,000 dalton cell surface protein.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., *Archives of Medical Research* (1997) 28:265-271), Epstein-Barr virus (EBV) can lead to lymphoma (see, e.g., Herrmann et al., *J Pathol* (2003) 199(2):140-5), hepatitis B or C virus can lead to liver carcinoma (see, e.g., El-Serag, *J Clin Gastroenterol* (2002) 35(5 Suppl 2):S72-8), human T cell leukemia virus (HTLV)-I can lead to T-cell leukemia (see e.g., Mortreux et al., *Leukemia* (2003) 17(1):26-38), human herpesvirus-8 infection can lead to Kaposi's sarcoma (see, e.g., Kadow et al., *Curr Opin Investig Drugs* (2002) 3(11):1574-9), and Human Immune deficiency Virus (HIV) infection contribute to cancer development as a consequence of immunodeficiency (see, e.g., Dal Maso et al., *Lancet Oncol* (2003) 4(2):110-9).

In other embodiments, a subject exhibiting one or more of the following predisposing factors for malignancy can be treated by administration of the HDACIs and methods of the invention: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112-113) etc.), and exposure to carcinogens (e.g., smoking, and inhalation of or contacting with certain chemicals).

In another specific embodiment, the HDACIs and methods of the invention are administered to a human subject to prevent progression to breast, colon, ovarian, or cervical cancer.

In one embodiment, the invention provides methods for treating cancer comprising (a) administering to an individual in need thereof an amount of an HDACI of structural formula (I); and (b) administering to the individual one or more additional anticancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In one embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, an HDACI of structural formula (I) or a pharmaceutically acceptable salt thereof is administered adjunctively with the additional anticancer treatment modality.

In a preferred embodiment, the additional anticancer treatment modality is radiotherapy. In the methods of the present invention, any radiotherapy protocol can be used depending upon the type of cancer to be treated. Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present HDACI, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-

DA), 2,3-DPG, BW12C, calcium channel blockers, pentoxifylline, antiangiogenesis compounds, hydralazine, and L-BSO.

In a preferred embodiment, an HDACI of structural formula (I) or a pharmaceutically acceptable salt thereof is administered prior to the administration of radiotherapy and/or chemotherapy.

In another preferred embodiment, an HDACI of structural formula (I) or a pharmaceutically acceptable salt thereof is administered adjunctively with radiotherapy and/or chemotherapy.

An HDACI of structural formula (I) and additional treatment modalities can act additively or synergistically (i.e., the combination of an HDACI of structural formula (I) or a pharmaceutically acceptable salt thereof, and an additional anticancer treatment modality is more effective than their additive effects when each are administered alone). A synergistic combination permits the use of lower dosages of an HDACI of structural formula (I) and/or the additional treatment modality and/or less frequent administration of an HDACI of structural formula (I) and/or additional treatment modality to a subject with cancer. The ability to utilize lower dosages of an HDACI of structural formula (I) and/or an additional treatment modality and/or to administer a compound of the invention and the additional treatment modality less frequently can reduce the toxicity associated with the administration without reducing the efficacy of an HDACI of structural formula (I) and/or the additional treatment modality in the treatment of cancer. In addition, a synergistic effect can result in the improved efficacy of the treatment of cancer and/or the reduction of adverse or unwanted side effects associated with the administration of an HDACI of structural formula (I) and/or an additional anticancer treatment modality as monotherapy.

In one embodiment, the HDACIs of structural formula (I) may act synergistically with radiotherapy when administered in doses typically employed when such HDACIs are used alone for the treatment of cancer. In another embodiment, the HDACIs of structural formula (I) may act synergistically with radiotherapy when administered in doses that are less than doses typically employed when such HDACIs are used as monotherapy for the treatment of cancer.

In one embodiment, radiotherapy may act synergistically with an HDACI of structural formula (I) when administered in doses typically employed when radiotherapy is used as monotherapy for the treatment of cancer. In another embodiment, radiotherapy may act synergistically with a compound of the invention when administered in doses that are less than doses typically employed when radiotherapy is used as monotherapy for the treatment of cancer.

The effectiveness of the HDACIs of structural formula (I) as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14 about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the TCD50 assay.

In vivo assay systems typically use transplantable solid tumor systems in experimental subjects. Radiation survival parameters for normal tissues as well as for tumors can be assayed using in vivo methods known in the art.

The present invention provides methods of treating cancers comprising the administration of an effective amount of an HDACI of structural formula (I) in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the HDACIs of structural formula (I) as radiosensitizers in conjunction with radiotherapy.

When the combination therapy of the invention comprises administering an HDACI of structural formula (I) with one or more additional anticancer agents, the HDACI of structural formula (I) and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; anyone or a combination of the additional anticancer agents listed below may be administered.

The present invention includes methods for treating cancer comprising administering to an individual in need thereof an HDACI of structural formula (I) and one or more additional anticancer agents or pharmaceutically acceptable salts thereof. An HDACI of structural formula (I) and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, trofosfamide, chlorambucil, nitrosoureas, carmustine (BCNU), lomustine (CCNU), alkylsulphonates, busulfan, treosulfan, triazenes, plant alkaloids, vinca alkaloids (vineristine, vinblastine, vindesine, vinorelbine), taxoids, DNA topoisomcrase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, floxuridine, doxifluridine, ratitrexed, cytosine analogs, cytarabine (ara C), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, E1) 1089, CB 1093, ICH 1060, photodynamic therapies, vertoporfin, BPD-MA, phthalocyanine, photosensitizer Pc4, demethoxy-hypocrellin A (2BA-2-DMHA), cytokines, interferon-a, interferon-I3, interferon-y, tumor necrosis factor, angiogenesis inhibitors, angiostatin (plasminogen fragment), antiangiogenic antithrombin UI, angiozyme, ABT-627, Bay 12-9566, benefin, bevacizumab, BMS-275291, cartilage-derived inhibitor (CDI), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (UMPs), 2-methoxyestradiol, MMI 270 (CGS 27023A), MoAb IMC-I C11, neovastat, NM-3, panzem, P1-88, placental ribonuclease inhibitor, plasminogen activator inhibitor, platelet factor-4 (PF4), prinomastat, prolactin 161(D fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1), TNP-470, transforming growth factor-beta (TGF-11), vasculostatin, vasostatin (calreticulin fragment), ZD 6126, ZD 6474, farnesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, $Ca^{2+}ATPase$ inhibitors, and thapsigargin.

Other anti-cancer agents that may be used in the present invention include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelcsin; bleomycin sulfate; brequinar sodium; bropirimine; busul fan; cactinomycin; calusterone; caracemide; carbetimer; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexorrnaplatin; dezaguanine; dezaguanine mesylate; diaziquone; docetaxel; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mecchlorethamine hydrochloride; megestrol acetate; melengestrol acetate; melphalan; menogaril; mercaptopurine; methotrexate sodium; metoprine; meturedepa; mitindomide; mitocarcin; mitocromin; mitogillin; mitomalcin; mitomycin; mitusper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsornycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracit mustard; uredepa; vapreotide; verteporfln; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride.

Further anti-cancer drugs that can be used in the present invention include, but are not limited to: 20-epi-1,25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCRJABL antagonists; benzochlorins; benzoylstaurosporine; beta lactam derivatives; beta alethine; betaclarnycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide amino triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fltidarabine; fluorodaunoruniein hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubiein; ipomeanol, 4; iroplact; irsogladine; isobengazole; isohomohalicondrin B; itasetron; jasplakinolide; kahalalide F; larnellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostin; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; propyl his acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RH retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thyrnotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the invention that the HDACIs of structural formula (I) can be administered in conjunction with chemical agents that are understood to mimic the effects of radiotherapy and/or that function by direct contact with DNA. Preferred agents for use in combination with the HDACIs of structural formula (I) for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the HDACIs of structural formula (I) as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

The HDACIs of structural formula (I) can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of an HDACI of structural formula (I) effective to eradicate the subject's remaining bone-marrow cell population, then the stem cell graft is infused back into the subject. Supportive care then is provided while bone marrow function is restored and the subject recovers.

The present methods for treating cancer can further comprise the administration of an HDACI of structural formula (I) and an additional therapeutic agent or pharmaceutically acceptable salts or hydrates thereof. In one embodiment, a composition comprising an HDACI of structural formula (I) is administered concurrently with the administration of one or more additional therapeutic agent(s), which may be part of the same composition or in a different composition from that comprising the HDACI of structural formula (I). In another embodiment, an HDACI of structural formula (I) is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

In a preferred embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargramostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, the HDACIs of the present invention are used in methods of treating diseases, conditions, and injuries to the central nervous system, such as neurological diseases, neurodegenerative disorders, and traumatic brain injuries (TBIs). In preferred embodiments, a present HDACI is capable of crossing the blood brain barrier to inhibit HDAC in the brain of the individual.

It has been shown that HDAC6 inhibition protects against neuronal degeneration and stimulates neurite outgrowth in dorsal root ganglion neurons, therefore indicating methods of treating CNS diseases. Accordingly, compound 6 was examined in a model of oxidative stress induced by homocysteic acid (HCA). This model leads to depletion of glutathione, the major intracellular antioxidant. HDAC6 inhibition rescues neuronal death in this model, possibly by causing hyperacetylation of peroxiredoxins. Previous work reported that nonselective, hydroxamic acid HDACIs displayed considerable toxicity to the primary cortical neurons. (A. P. Kozikowski et al., *J. Med. Chem.* 2007, 50, 3054-61.)

Figure 1B:
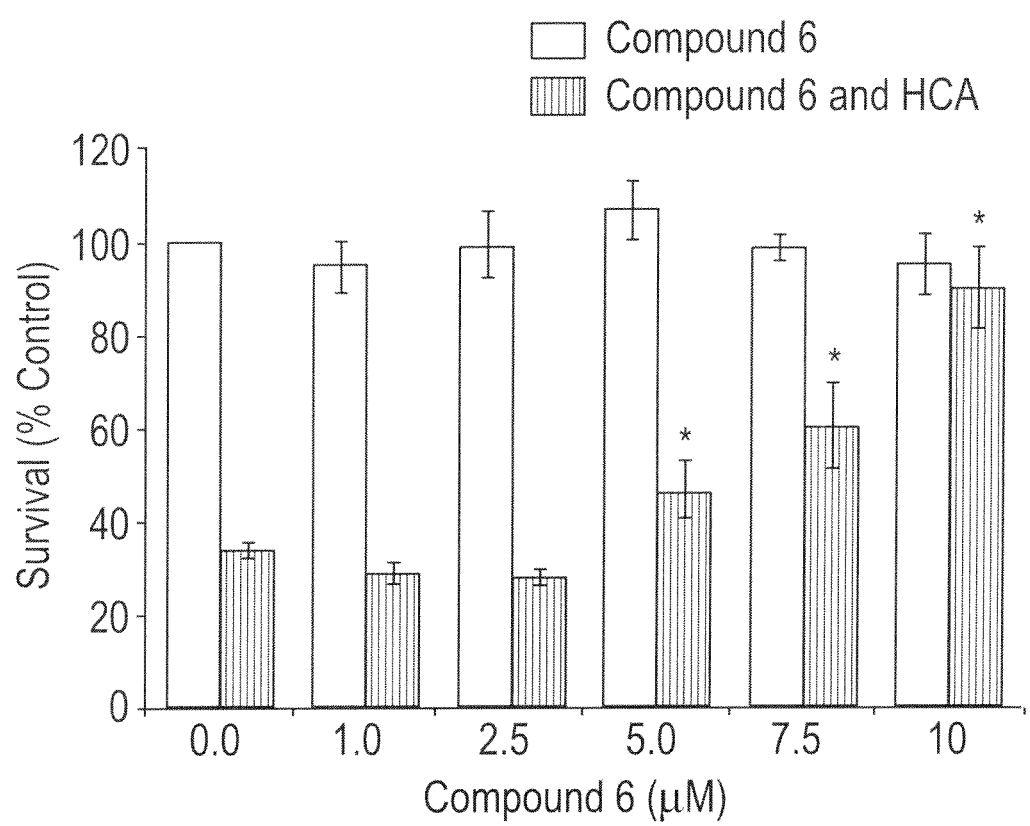

In the HCA-induced neurodegeneration assays, TSA was moderately neuroprotective at 0.5 µM, although protection declined at higher concentrations due to dose-dependant neurotoxicity (FIG. 1A). Compound 6 displayed dose-dependent protection against HCA-induced neuronal cell death starting at 5 µM with near complete protection at 10 µM (FIG. 1B). This compares well with published results showing that Tubacin induces α-tubulin acetylation at 5 µM and protects prostate cancer (LNCaP) cells from hydrogen peroxide-induced death at 8 µM via peroxiredoxin acetylation. (R. B. Parmigiani et al., *Proc. Natl. Acad. Sci. USA* 2008, 105, 9633-8.) Importantly, when tested alone at all of the concentrations shown, compound 6 exhibited no toxicity, indicating that neurotoxicity is likely a product of class I HDAC inhibition, and not a property inherent to hydroxamic acids. Compound 6 is the first neuroprotective hydroxamic acid-based HDACI that does not cause neuronal death when tested alone in the HCA model. These results demonstrate that HDAC6 inhibition provides a method for treating neurodegenerative conditions.

FIGS. 1A and 1B contain neuroprotection bar graphs of the HCA oxidative stress test assay. Neurons were treated with TSA (FIG. 1A) or Compound 6, alone or with the addition of HCA (homocysteic acid).

The data summarized in FIGS. 1A and 1B was obtained according to the following neuroprotective assay. Primary cortical neuron cultures were obtained from the cerebral cortex of fetal Sprague-Dawley rats (embryonic day 17). All experiments were initiated 24 hours after plating. Under these conditions, the cells are not susceptible to glutamate-mediated excitotoxicity. For cytotoxicity studies, cells were rinsed with warm PBS, then placed in minimum essential medium (Invitrogen) containing 5.5 g/liter glucose, 10% fetal calf serum, 2 mM L-glutamine, and 100 µM cystine. Oxidative stress was induced by the addition of the glutamate analog homocysteate (HCA; 5 mM) to the media. HCA was diluted from 100-fold concentrated solutions that were adjusted to pH 7.5. In combination with HCA, neurons were treated with either TSA or compound 6 at the indicated concentrations. Viability was assessed after 24 hours by the MTT assay (3-(4,5-dimethylthiazol-2-yl)-2,5-diphenyltetrazolium bromide) method.

Compound 6 also was found to ameliorate associative memory following Aβ elevation. In this test, mice were infused with Aβ42 via cannulas implanted into dorsal hippocampus 15 minutes prior to training. Compound 6 was dosed ip (25 mg/kg) 2 hours before training. Fear learning was assessed 24 hours later.

Figure 2:
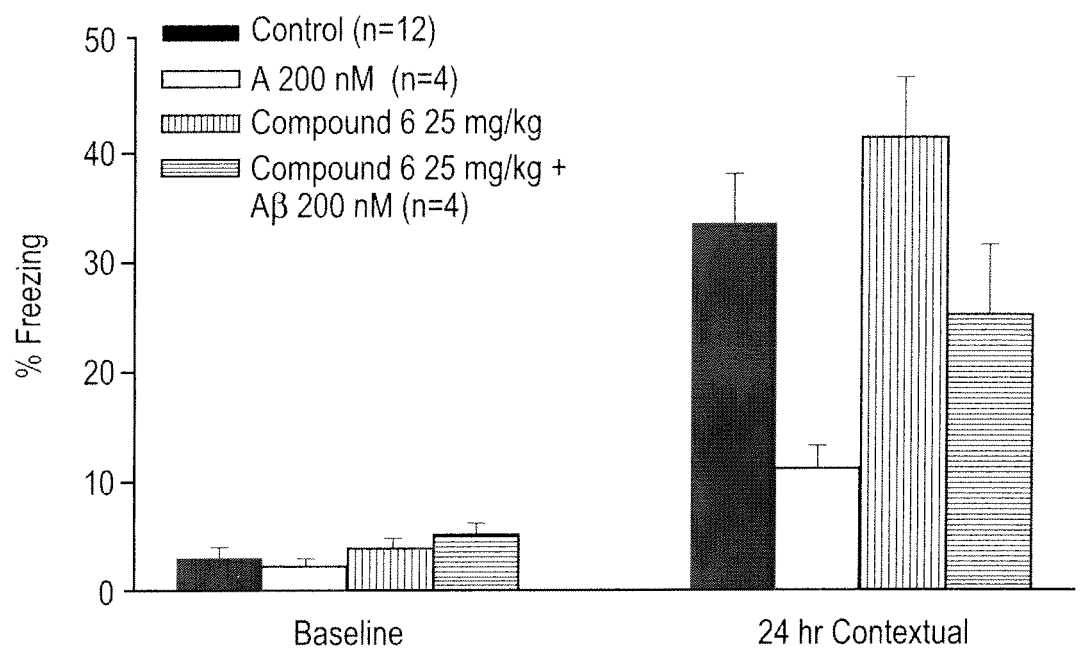
FIG. 2 contains bar graphs of % freezing response for mice treated with Aβ42, compound 6, or Aβ42 and compound 6 versus a control.

Contextual fear conditioning performed 24 hours after training showed a reduction of freezing in Aβ-infused mice compared to vehicle-infused mice (FIG. 2). Treatment with compound 6 ameliorates deficit in freezing responses in Aβ-infused mice, and has no effect in vehicle-infused mice (FIG. 2). Compound 6 alone did not affect the memory performance of the mice. In addition, treatment had no effects on motor, sensorial, or motivational skills assessed using the visible platform test in which compound 6 was injected twice a day for two days. During these experiments, no signs of overt toxicity, including changes in food and liquid intake, weight loss, or changes in locomotion and exploratory behavior, were observed.

These results demonstrate that the HDACIs of the present invention are beneficial against impairment of associative memory following Aβ elevation.

The HDACIs of structural formula (I) therefore are useful for treating a neurological disease by administration of amounts of an HDACI of structural formula (I) effective to treat the neurological disease or by administration of a pharmaceutical composition comprising amounts of an HDACI of structural formula (I) effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCA7), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, and multi infarct state.

In a preferred embodiment, the neurological disease treated is Huntington's disease, Parkinson's disease, Alzheimer's disease, spinal muscular atrophy, lupus, or schizophrenia.

A present HDACI also can be used with a second therapeutic agent in methods of treating conditions, diseases, and injuries to the CNS. Such second therapeutic agents are those drugs known in the art to treat a particular condition, diseases, or injury, for example, but not limited to, lithium in the treatment of mood disorders, estradiol benzoate, and nicotinamide in the treatment of Huntington's disease.

The present HDACIs also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis (MS), Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

The present HDACIs therefore also are useful in the treatment of inflammation and strokes, and in the treatment of autism. The present HDACIs further can be used to treat parasitic infections, (e.g., malaria, toxoplasmosis, trypanosomiasis, helminthiasis, protozoal infections (see Andrews et al. Int. J. Parasitol. 2000, 30(6), 761-768).

In certain embodiments, the compound of the invention can be used to treat malaria. A present HDACI can be co-administered with an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones, and iron chelating agents. The antimalarial compound can be, but is not limited to, quinine, quinidine, mefloquine, halfantrine, chloroquine, amodiaquine, proguanil, chloroproquanil, pyrimethamine, primaquine, 8-[(4-amino-1-methylbutyl)amino]-2,6-dimethoxy-4-methyl-5-[(3-trifluoromethyl)phenoxy]quinoline succinate (WR238, 605), tetracycline, doxycycline, clindamycin, azithromycin, fluoroquinolones, artemether, areether, artesunate, artelinic acid, atovaquone, and deferrioxamine. In a preferred embodiment, the antimalarial compound is chloroquine.

The present HDACIs also can be used as imaging agents. In particular, by providing a radiolabeled or fluorescently-labeled HDACI of structural formula (I), the labeled compound can image HDACs, tissues expressing HDACIs, and tumors. Labeled HDACIs of structural formula (I) also can image patients suffering from a cancer, or other HDAC-mediated diseases, e.g., stroke, by administration of an effective amount of the labeled compound or a composition containing the labeled compound. In preferred embodiments, the labeled HDACI is capable of emitting positron radiation and is suitable for use in positron emission tomography (PET). Typically, a labeled HDACI of structural formula (I) is used to identify areas of tissues or targets that express high concentrations of HDACs. The extent of accumulation of labeled HDACI can be quantified using known methods for quantifying radioactive emissions.

HDACIs of structural formula (I) useful in the imaging methods contain one or more radioisotopes capable of emitting one or more forms of radiation suitable for detection by any standard radiology equipment, such as PET, SPECT, gamma cameras, MRI, and similar apparatus. Preferred isotopes including tritium ($^3$H) and carbon ($^{11}$C). Substituted HDACIs of structural formula (I) also can contain isotopes of fluorine ($^{18}$F) and iodine ($^{123}$I) for imaging methods. Typically, a labeled HDACI of structural formula (I) contains an alkyl group having a $^{11}$C label, i.e., a $^{11}$C-methyl group, or an alkyl group substituted with $^{18}$F, $^{123}$I, $^{125}$I, $^{131}$I, or a combination thereof.

Fluorescently labeled HDACIs of structural formula (I) also can be used in the imaging method of the present invention. Such compounds have an FITC or carbocyamine moiety.

The labeled HDACIs and methods of use can be in vivo, and particularly on humans, and for in vitro applications, such as diagnostic and research applications, using body fluids and cell samples. The imaging methods using a labeled HDACI of structural formula (I) are discussed in WO 03/060523, designating the U.S. and incorporated in its entirety herein. Typically, the method comprises contacting cells or tissues with a radiolabeled compound of structural formula (I), and making a radiographic image, i.e., a sufficient amount to provide about 1 to about 30 mCi of the radiolabeled compound.

Preferred imaging methods include the use of labeled HDACIs of structural formula (I) which are capable of generating at least a 2:1 target to background ratio of radiation intensity, or more preferably about a 5:1, about 10:1, or about 15:1 ratio of radiation intensity between target and background.

In preferred methods, the labeled HDACIs of structural formula (I) are excreted from tissues of the body quickly to prevent prolonged exposure to the radiation of the radiolabeled compound administered to the individual. Typically, labeled HDACIs of structural formula I are eliminated from the body in less than about 24 hours. More preferably, labeled HDACIs are eliminated from the body in less than about 16 hours, 12 hours, 8 hours, 6 hours, 4 hours, 2 hours, 90 minutes, or 60 minutes. Typically, preferred labeled HDACIs are eliminated in about 60 to about 120 minutes.

The HDACIs of structural formula (I) also are useful in the treatment of autoimmune diseases and inflammations. Compounds of the present invention are particularly useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression. Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by sostimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (R. Tao et al., *Nat Med*, 13, 1299-1307, (2007). and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo studies are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with floxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

Compound 6 has been shown to enhance murine Treg suppression at a concentration of greater than 100 $\mu$M. Compound 6 also has been shown to prolong cardiac allograft survival in mice.

Compound 6 further demonstrates anti-arthritic efficacy in a collagen-induced arthritis model in DBA1/J mice. In this test, DBA1/J mice (male, 7-8 weeks) were used, with 8 animals per group. Systemic arthritis was induced with bovine collagen type II and CFA, plus an IFA booster injection on day 21. Both ENBREL® and compound 6 were dosed IP on day 28 for 2 consecutive weeks (compound 6 compound only). Compound 6 was dosed at 50 and 100 mg/kg. No loss of body weight was observed in either group.

Figure 3:
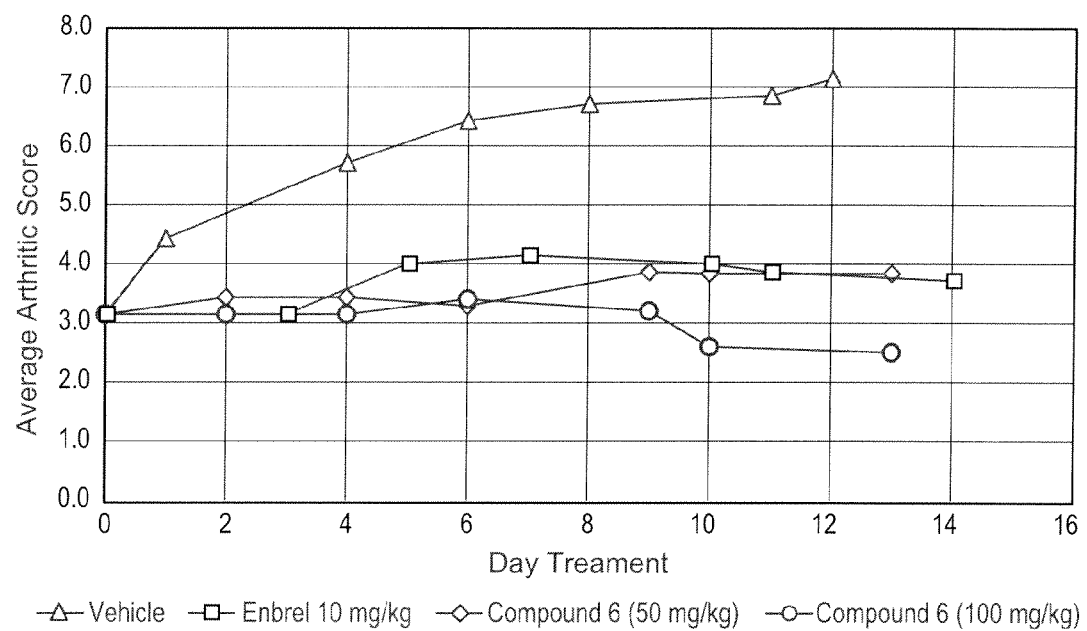
FIG. 3 contains plots of Average Arthritic Score vs. Day of Treatment for mice treated with vehicle, ENBREL® 10 mg/kg, compound 6 (50 mg/kg), or compound 6 (100 mg/kg).

The results are summarized in FIG. 3, containing graphs of Average Arthritic Score vs. Days of Treatment. Compound 6 performed as well as ENBREL at 50 mg/kg and outperformed ENBREL® at 100 mg/kg.

Therefore, despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

HDACIs of structural formula (I) are potent immunosuppressive agents that suppress humoral immunity and cell-mediated immune reactions, such as allograft rejection, delayed hypersensitivity, experimental allergic encephalomyelitis, Freund's adjuvant arthritis and graft versus host disease. HDACIs of the present invention are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of an HDACI of structural formula (I) can be used for immunosuppression including, for example, to prevent organ rejection or graft vs. host disease, and to treat diseases and conditions, in particular, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

An HDACI of structural formula (I) can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

In the present method, a therapeutically effective amount of one or more HDACI of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

An HDACI of structural formula (I) can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein an HDACI of structural formula (I) is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of an HDACI of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of an HDACI of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing an HDACI of structural formula (I), or a composition containing the same, can be from about 1 ng/kg to about 200 mg/kg, about 1 µg/kg to about 100 mg/kg, or about 1 mg/kg to about 50 mg/kg of body weight. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

An HDACI of structural formula (I) used in a method of the present invention typically is administered in an amount of about 0.005 to about 500 milligrams per dose, about 0.05 to about 250 milligrams per dose, or about 0.5 to about 100 milligrams per dose. For example, an HDACI of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of HDACIs of structural formula (I).

The term "carrier" refers to a diluent, adjuvant, or excipient, with which an HDACI of structural formula (I) is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when the HDACI of structural formula (I) is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of an HDACI of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of an HDACI of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of an HDACI of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. An HDACI of structural formula (I) can be infused with other fluids over a 10-30 minute span or over several hours.

HDACIs of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the HDACI of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

An HDACI of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of an HDACI of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

An HDACI of structural formula (I) also can be formulated in rectal compositions, such as suppositories or retention enemas, e.g., containing conventional suppository bases. In addition to the formulations described previously, the HDACI of structural formula (I) also can be formulated as a depot preparation. Such long-acting formulations can be administered by implantation (for example, subcutaneously or intramuscularly) or by intramuscular injection. Thus, for example, the HDACIs of structural formula (I) can be formulated with suitable polymeric or hydrophobic materials (for example, as an emulsion in an acceptable oil) or ion exchange resins.

In particular, the HDACIs of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The HDACIs of structural formula (I) also can be injected parenterally, for example, intravenously, intramuscularly, subcutaneously, or intracoronarily. For parenteral administration, the HDACIs are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising an HDACI of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, the compounds of structural formula (I) is a lyophilate. In this instance, the kit can further comprise an additional container which contains a solution useful for the reconstruction of the lyophilate.

Prior HDACIs possessed properties that hindered their development as therapeutic agents. In accordance with an important feature of the present invention, HDACIs of structural formula (I) were synthesized and evaluated as inhibitors for HDAC. For example, compounds of the present invention typically have a bonding affinity ($IC_{50}$) to HDAC6 of less than 100 μM, less than 25 μM, less than 10 μM, less than 1 μM, less than 0.5 μM, and less than 0.2 μM.

What is claimed:
1. A compound having a structure

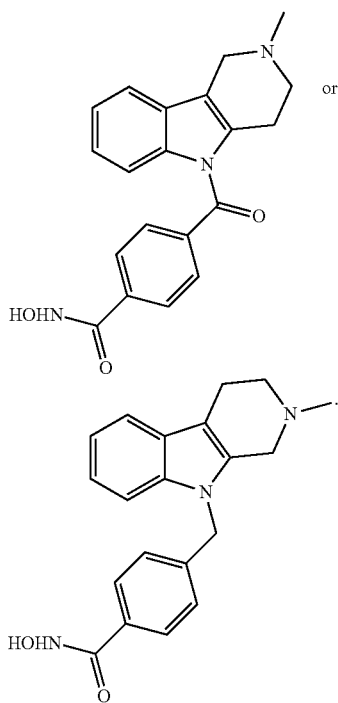

or

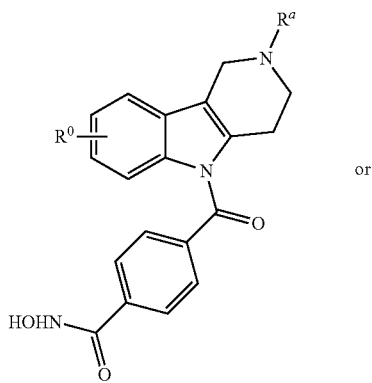

2. A compound having a structural formula

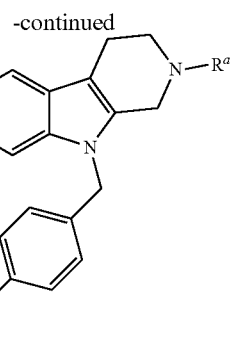

or -continued

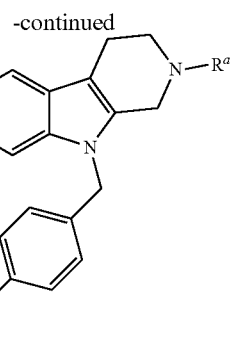

wherein $R^a$ is selected from the group consisting of hydrogen, $C_{1-3}$alkyl, —CH$_2$CH=CH$_2$, Boc, —C(=O)CH$_3$, —(CH$_2$)$_{0-3}$C(=O)NH$_2$, C(=O)CH(CH$_3$)NH$_2$, —CH$_2$C(=O)OH,

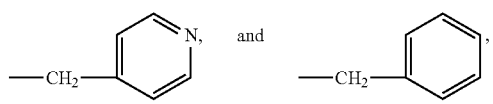

optionally substituted with —OCH$_3$;
$R^o$ is selected from the group consisting of hydrogen, $C_{1-4}$alkyl, —OCH$_3$, halo, and

or a pharmaceutically acceptable salt or prodrug thereof.

3. The compound of claim 2 wherein $R^a$ is selected from the group consisting of hydrogen, —CH$_3$, —CH$_2$CH$_3$, —CH(CH$_3$)$_2$, —C(=O)NH$_2$, —CH$_2$CH=CH$_2$, -Boc,

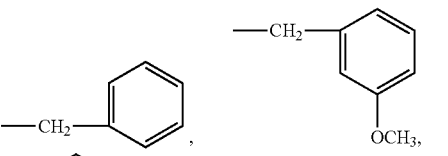

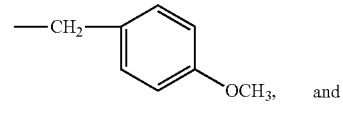

4. The compound of claim 2 wherein $R^o$ is selected from the group consisting of —CH$_3$, —C(CH$_3$)$_3$, —Cl, -Br, —OCH$_3$, and

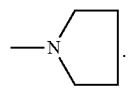

* * * * *